US011568980B2

(12) United States Patent
Chancellor et al.

(10) Patent No.: US 11,568,980 B2
(45) Date of Patent: *Jan. 31, 2023

(54) SYSTEMS AND METHODS FOR ASSISTING INDIVIDUALS IN A BEHAVIORAL-CHANGE PROGRAM

(71) Applicant: Carrot, Inc., Redwood City, CA (US)

(72) Inventors: Joe Chancellor, Fremont, CA (US); Laura Dotson, San Francisco, CA (US); Aneesh Joshi, Whitby (CA); Linda Bundick, Columbus, IN (US); David S. Utley, Redwood City, CA (US); Daniel Balbierz, Redwood City, CA (US); Rajiv Vaidyanathan, Belmont, CA (US); Allen Jameson, Sunnyvale, CA (US)

(73) Assignee: Pivot Health Technologies Inc., San Carlos, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/450,656

(22) Filed: Oct. 12, 2021

(65) Prior Publication Data

US 2022/0139525 A1 May 5, 2022

Related U.S. Application Data

(63) Continuation of application No. 17/138,491, filed on Dec. 30, 2020, now Pat. No. 11,257,583.
(Continued)

(51) Int. Cl.
*G08B 1/00* (2006.01)
*G16H 20/70* (2018.01)
(Continued)

(52) U.S. Cl.
CPC ............. *G16H 20/70* (2018.01); *G16H 10/60* (2018.01); *G16H 15/00* (2018.01); *G16H 80/00* (2018.01)

(58) Field of Classification Search
CPC ........ G16H 20/70; G16H 10/60; G16H 15/00; G16H 80/00
(Continued)

(56) References Cited

U.S. PATENT DOCUMENTS 3,953,566 A  4/1976 Gore
4,220,142 A  9/1980 Rosen et al.
(Continued)

FOREIGN PATENT DOCUMENTS

CN  107708584  2/2018
GB  2379509  3/2003
(Continued)

OTHER PUBLICATIONS

Deveci, S. E. et al. "The Measurement of Exhaled Carbon Monoxide in Healthy Smokers and Non-smokers," *Respiratory Medicine*, vol. 98, No. 6, pp. 551-556, Jun. 2004.
(Continued)

*Primary Examiner* — Zhen Y Wu
(74) *Attorney, Agent, or Firm* — Levine Bagade Han LLP

(57) ABSTRACT

Methods and systems of enhancing an electronic interaction between a behavioral-modification program and a user in the program by providing customized content specific to the user. The systems and methods allow for coach-counselor assistance to the individual-user or for automated content delivery.

20 Claims, 41 Drawing Sheets

Related U.S. Application Data

(60) Provisional application No. 62/955,214, filed on Dec. 30, 2019, provisional application No. 62/955,219, filed on Dec. 30, 2019.

(51) Int. Cl.
  *G16H 15/00* (2018.01)
  *G16H 10/60* (2018.01)
  *G16H 80/00* (2018.01)

(58) Field of Classification Search
  USPC .......................................................... 340/531
  See application file for complete search history.

(56) References Cited

U.S. PATENT DOCUMENTS

| | | |
|---|---|---|
| 4,246,913 A | 1/1981 | Ogden et al. |
| 4,277,452 A | 7/1981 | Kanehori et al. |
| 4,585,417 A | 4/1986 | Sozio et al. |
| 4,609,349 A | 9/1986 | Cain |
| 4,615,681 A | 10/1986 | Schwarz |
| 4,629,424 A | 12/1986 | Lauks et al. |
| 4,853,854 A | 8/1989 | Behar et al. |
| 4,896,143 A | 1/1990 | Dolnick et al. |
| 4,904,520 A | 2/1990 | Dumas et al. |
| 4,971,558 A | 11/1990 | Jacobi |
| 4,992,049 A | 2/1991 | Weissman |
| 4,996,161 A | 2/1991 | Conners et al. |
| 5,021,457 A | 6/1991 | Akin et al. |
| 5,035,860 A | 7/1991 | Kleingeld et al. |
| 5,063,164 A | 11/1991 | Goldstein |
| 5,188,109 A | 2/1993 | Saito |
| 5,284,163 A | 2/1994 | Knudsen et al. |
| 5,293,875 A | 3/1994 | Stone |
| 5,361,771 A | 11/1994 | Craine et al. |
| 5,565,152 A | 10/1996 | Od et al. |
| 5,596,994 A | 1/1997 | Bro |
| 5,618,493 A | 4/1997 | Goldstein et al. |
| 5,647,345 A | 7/1997 | Saul |
| 5,764,150 A | 6/1998 | Fleury et al. |
| 5,778,897 A | 7/1998 | Nordlicht |
| 5,826,577 A | 10/1998 | Perroz, Jr. et al. |
| 5,829,971 A | 11/1998 | Razdolsky et al. |
| 5,841,021 A | 11/1998 | De et al. |
| 5,908,301 A | 6/1999 | Lutz |
| 6,039,688 A | 3/2000 | Douglas et al. |
| 6,067,523 A | 5/2000 | Bair et al. |
| 6,164,278 A | 12/2000 | Nissani |
| 6,334,778 B1 | 1/2002 | Brown |
| 6,340,588 B1 | 1/2002 | Nova et al. |
| 6,397,093 B1 | 5/2002 | Aldrich |
| 6,544,199 B1 | 4/2003 | Morris |
| 6,599,253 B1 | 4/2003 | Smits et al. |
| 6,544,190 B1 | 7/2003 | Baum et al. |
| 6,602,892 B1 | 8/2003 | Sachs |
| 6,613,001 B1 | 9/2003 | Dworkin |
| 6,730,494 B1 | 5/2004 | Toranto et al. |
| 6,748,792 B1 | 6/2004 | Freund et al. |
| 6,858,182 B1 | 2/2005 | Ito et al. |
| 7,054,679 B2 | 5/2006 | Hirsh |
| 7,163,511 B2 | 1/2007 | Conn et al. |
| 7,408,640 B2 | 8/2008 | Cullum et al. |
| 7,421,882 B2 | 9/2008 | Leddy et al. |
| 7,451,852 B2 | 11/2008 | Stewart et al. |
| 7,525,093 B2 | 4/2009 | Stenberg |
| 7,610,919 B2 | 11/2009 | Utley et al. |
| 7,661,955 B2 | 2/2010 | Da Cruz |
| 7,716,383 B2 | 5/2010 | Lei et al. |
| 7,720,516 B2 | 5/2010 | Chin et al. |
| 7,797,982 B2 | 9/2010 | Burke et al. |
| 7,899,518 B2 | 3/2011 | Trepagnier et al. |
| 8,130,105 B2 | 3/2012 | Al-Ali et al. |
| 8,160,279 B2 | 4/2012 | Abolfathi |
| 8,190,223 B2 | 5/2012 | Al-Ali et al. |
| 8,211,035 B2 | 7/2012 | Melker et al. |
| 8,224,411 B2 | 7/2012 | Al-Ali et al. |
| 8,224,667 B1 | 7/2012 | Miller et al. |
| 8,235,921 B2 | 8/2012 | Rousso et al. |
| 8,249,311 B2 | 8/2012 | Endo et al. |
| 8,311,601 B2 | 11/2012 | Besko |
| 8,560,032 B2 | 10/2013 | Al-Ali et al. |
| 9,420,971 B2 | 8/2016 | Utley et al. |
| 9,675,275 B2 | 6/2017 | Utley et al. |
| 9,861,126 B2 | 1/2018 | Utley et al. |
| 10,206,572 B1 | 2/2019 | Utley et al. |
| 10,335,032 B2 | 7/2019 | Utley et al. |
| 10,499,819 B2 | 12/2019 | Wondka et al. |
| 10,674,761 B2 | 6/2020 | Utley et al. |
| 10,674,913 B2 | 6/2020 | Utley et al. |
| 10,861,595 B2 | 12/2020 | Satake et al. |
| 10,923,220 B2* | 2/2021 | Satake ................... G16H 10/20 |
| 10,936,962 B1* | 3/2021 | Neumann ............... G06N 20/00 |
| 11,257,583 B2* | 2/2022 | Chancellor ............ G16H 20/70 |
| 11,278,203 B2* | 3/2022 | Utley ................... A61B 5/4836 |
| 11,412,784 B2 | 8/2022 | Utley et al. |
| 2001/0027384 A1 | 10/2001 | Schulze et al. |
| 2001/0027794 A1 | 10/2001 | Brue |
| 2001/0037070 A1 | 11/2001 | Cranley et al. |
| 2002/0026937 A1 | 3/2002 | Mault |
| 2002/0061495 A1 | 5/2002 | Mault |
| 2002/0072959 A1 | 6/2002 | Clendonon |
| 2002/0146346 A1 | 10/2002 | Konecke |
| 2002/0177232 A1 | 11/2002 | Melker et al. |
| 2003/0003113 A1 | 1/2003 | Lewandowski |
| 2003/0004403 A1 | 1/2003 | Drinan et al. |
| 2003/0004426 A1 | 1/2003 | Melker et al. |
| 2003/0015019 A1 | 1/2003 | O'Brien |
| 2003/0050567 A1 | 3/2003 | Baghdassarian |
| 2003/0109795 A1 | 6/2003 | Webber |
| 2003/0149372 A1 | 8/2003 | Smith et al. |
| 2003/0211007 A1 | 11/2003 | Maus et al. |
| 2004/0006113 A1 | 1/2004 | Sachs |
| 2004/0031498 A1 | 2/2004 | Brue |
| 2004/0035183 A1 | 2/2004 | O'Brien et al. |
| 2004/0158194 A1 | 8/2004 | Wolff et al. |
| 2004/0210154 A1 | 10/2004 | Kline |
| 2004/0239510 A1 | 12/2004 | Karsten |
| 2005/0053523 A1 | 3/2005 | Brooke |
| 2005/0081601 A1 | 4/2005 | Lawson |
| 2005/0112148 A1 | 5/2005 | Dmitruk |
| 2005/0141346 A1 | 6/2005 | Rawls et al. |
| 2005/0163293 A1 | 7/2005 | Hawthorne et al. |
| 2005/0171816 A1 | 8/2005 | Meinert et al. |
| 2005/0177050 A1* | 8/2005 | Cohen ................... G16H 10/60 |
| | | 600/509 |
| 2005/0177056 A1 | 8/2005 | Giron et al. |
| 2005/0177615 A1 | 8/2005 | Hawthorne et al. |
| 2005/0263160 A1 | 12/2005 | Utley et al. |
| 2006/0144126 A1 | 7/2006 | O'Brien et al. |
| 2006/0167723 A1 | 7/2006 | Berg |
| 2006/0193749 A1 | 8/2006 | Ghazarian et al. |
| 2006/0220881 A1 | 10/2006 | Al-Ali et al. |
| 2006/0226992 A1 | 10/2006 | Al-Ali et al. |
| 2006/0229914 A1 | 10/2006 | Armstrong |
| 2006/0237253 A1 | 10/2006 | Mobley et al. |
| 2006/0238358 A1 | 10/2006 | Al-Ali et al. |
| 2007/0005988 A1 | 1/2007 | Zhang et al. |
| 2007/0093725 A1 | 4/2007 | Shaw |
| 2007/0100595 A1* | 5/2007 | Earles ................ G06Q 30/0207 |
| | | 703/13 |
| 2007/0164220 A1 | 7/2007 | Luk |
| 2007/0168501 A1* | 7/2007 | Cobb ..................... G06Q 30/02 |
| | | 709/224 |
| 2007/0209669 A1 | 9/2007 | Derchak |
| 2007/0271997 A1 | 11/2007 | O'Brien |
| 2007/0277823 A1 | 12/2007 | Al-Ali et al. |
| 2007/0277836 A1 | 12/2007 | Longley |
| 2007/0282226 A1 | 12/2007 | Longley |
| 2007/0282930 A1* | 12/2007 | Doss ..................... G09B 23/28 |
| | | 708/111 |
| 2008/0078232 A1 | 4/2008 | Burke et al. |
| 2008/0126277 A1 | 5/2008 | Williams et al. |
| 2008/0146890 A1 | 6/2008 | LeBoeuf et al. |
| 2008/0162352 A1 | 7/2008 | Gizewski |

(56) References Cited

U.S. PATENT DOCUMENTS

| | | |
|---|---|---|
| 2008/0199838 A1 | 8/2008 | Flanagan |
| 2008/0221418 A1 | 9/2008 | Al-Ali et al. |
| 2009/0069642 A1 | 3/2009 | Gao et al. |
| 2009/0164141 A1 | 6/2009 | Lee |
| 2009/0191523 A2 | 7/2009 | Flanagan |
| 2009/0216132 A1 | 8/2009 | Orbach |
| 2009/0253220 A1 | 10/2009 | Banerjee |
| 2009/0293589 A1 | 12/2009 | Freund et al. |
| 2009/0325639 A1 | 12/2009 | Koehn |
| 2010/0009324 A1 | 1/2010 | Owens et al. |
| 2010/0010321 A1 | 1/2010 | Foster |
| 2010/0010325 A1 | 1/2010 | Ridder et al. |
| 2010/0010433 A1 | 1/2010 | Krogh et al. |
| 2010/0012417 A1 | 1/2010 | Walter et al. |
| 2010/0081955 A1 | 4/2010 | Wood et al. |
| 2010/0116021 A1 | 5/2010 | O'Brien |
| 2010/0204600 A1 | 8/2010 | Crucilla |
| 2010/0209897 A1 | 8/2010 | Utley et al. |
| 2010/0222648 A1* | 9/2010 | Tan ................. G16H 40/67 702/85 |
| 2010/0234064 A1 | 9/2010 | Harris |
| 2010/0280821 A1* | 11/2010 | Tiitola ............... G06F 40/274 704/200 |
| 2010/0298683 A1 | 11/2010 | Cabrera et al. |
| 2011/0035158 A1 | 2/2011 | Banos et al. |
| 2011/0079073 A1 | 4/2011 | Keays |
| 2011/0125063 A1 | 5/2011 | Shalon et al. |
| 2011/0153223 A1 | 6/2011 | Gentala et al. |
| 2011/0218822 A1* | 9/2011 | Buisman ............ G16H 15/00 705/2 |
| 2011/0247638 A1 | 10/2011 | Ayala |
| 2011/0263947 A1 | 10/2011 | Utley et al. |
| 2011/0265552 A1 | 11/2011 | Stedman |
| 2011/0270052 A1 | 11/2011 | Jensen et al. |
| 2011/0270053 A1 | 11/2011 | Utley et al. |
| 2011/0295140 A1 | 12/2011 | Zaidi et al. |
| 2012/0022890 A1 | 1/2012 | Williams et al. |
| 2012/0059664 A1* | 3/2012 | Georgiev ............ A61B 5/021 705/2 |
| 2012/0068848 A1 | 3/2012 | Campbell et al. |
| 2012/0115115 A1 | 5/2012 | Rapoza |
| 2012/0130584 A1 | 5/2012 | Stedman |
| 2012/0161970 A1 | 6/2012 | Al-Ali et al. |
| 2012/0190955 A1 | 7/2012 | Rao et al. |
| 2012/0191052 A1 | 7/2012 | Rao |
| 2012/0232359 A1 | 9/2012 | Al-Ali et al. |
| 2012/0238834 A1 | 9/2012 | Hornick |
| 2012/0294876 A1 | 11/2012 | Zimmerman |
| 2013/0211291 A1 | 8/2013 | Tran |
| 2013/0233052 A1 | 9/2013 | Stedman |
| 2013/0253849 A1 | 9/2013 | Gentala et al. |
| 2013/0304581 A1 | 11/2013 | Soroca et al. |
| 2013/0316926 A1 | 11/2013 | Caffrey |
| 2013/0317384 A1* | 11/2013 | Le .................. G16H 20/70 600/545 |
| 2014/0033796 A1 | 2/2014 | Stedman |
| 2014/0051043 A1 | 2/2014 | Mosby |
| 2014/0081667 A1* | 3/2014 | Joao ................ G16H 40/63 705/3 |
| 2014/0142965 A1* | 5/2014 | Houston ............ G16H 40/67 705/2 |
| 2014/0228699 A1 | 8/2014 | Causevic et al. |
| 2014/0257127 A1 | 9/2014 | Smith et al. |
| 2014/0358018 A1 | 12/2014 | Neagle, III |
| 2015/0024355 A1* | 1/2015 | Ghofrani ............. A24F 47/00 434/236 |
| 2015/0025407 A1 | 1/2015 | Eichler et al. |
| 2015/0032019 A1 | 1/2015 | Acker et al. |
| 2015/0064672 A1 | 3/2015 | Bars |
| 2015/0065825 A1* | 3/2015 | Utley ................ G16Z 99/00 131/270 |
| 2015/0201865 A1 | 7/2015 | Forzani et al. |
| 2016/0029693 A1* | 2/2016 | Klein ............... G16H 20/70 434/236 |
| 2016/0151603 A1 | 6/2016 | Shouldice et al. |
| 2016/0192880 A9 | 7/2016 | Utley et al. |
| 2016/0219931 A1* | 8/2016 | Doshi ................ A24F 47/00 |
| 2016/0224752 A1* | 8/2016 | Van Wyck ........... H04L 65/611 |
| 2016/0246936 A1* | 8/2016 | Kahn ................ G16H 40/63 |
| 2016/0324469 A1 | 11/2016 | Utley et al. |
| 2017/0055572 A1 | 3/2017 | Utley et al. |
| 2017/0055573 A1 | 3/2017 | Utley et al. |
| 2017/0319105 A1 | 11/2017 | Utley et al. |
| 2017/0323065 A1* | 11/2017 | Proctor Beauchamp ................ A61B 5/165 |
| 2018/0108347 A1* | 4/2018 | Ogata ................ G06Q 50/10 |
| 2018/0116560 A1* | 5/2018 | Quinn ............... A61B 5/02055 |
| 2018/0129535 A1* | 5/2018 | Carteri ............... H04L 67/535 |
| 2018/0301214 A1* | 10/2018 | Satake .............. G06Q 30/0281 |
| 2019/0104938 A1 | 4/2019 | Utley et al. |
| 2019/0113501 A1 | 4/2019 | Jameson et al. |
| 2019/0150831 A1 | 5/2019 | Payton et al. |
| 2019/0239564 A1 | 8/2019 | Utley et al. |
| 2019/0244015 A1* | 8/2019 | Lee ................. H04N 7/141 |
| 2019/0261855 A1 | 8/2019 | Utley et al. |
| 2020/0288785 A1 | 9/2020 | Utley et al. |
| 2020/0288979 A1 | 9/2020 | Utley et al. |
| 2020/0305729 A1 | 10/2020 | Wondka et al. |
| 2020/0320363 A1* | 10/2020 | Neumann ............ G06N 20/20 |
| 2020/0342352 A1* | 10/2020 | Neumann ............ G16B 20/00 |
| 2020/0342353 A1* | 10/2020 | Neumann ............ G16H 20/60 |
| 2020/0380458 A1* | 12/2020 | Neumann ............ G16H 20/60 |
| 2021/0004377 A1* | 1/2021 | Neumann ............ G06F 16/252 |
| 2021/0004691 A1* | 1/2021 | Neumann ............ G16H 20/60 |
| 2021/0004715 A1* | 1/2021 | Neumann ............ G16H 50/70 |
| 2021/0005316 A1* | 1/2021 | Neumann ............ G16H 50/70 |
| 2021/0057066 A1 | 2/2021 | Satake et al. |
| 2021/0196147 A1 | 7/2021 | Jameson et al. |
| 2021/0202066 A1 | 7/2021 | Chancellor et al. |
| 2021/0407638 A1* | 12/2021 | Neumann ............ G16H 50/20 |
| 2022/0139525 A1* | 5/2022 | Chancellor ........... G16H 15/00 340/531 |
| 2022/0233075 A1 | 7/2022 | Utley et al. |

FOREIGN PATENT DOCUMENTS

| | | |
|---|---|---|
| JP | 2005-070953 | 3/2005 |
| JP | 2018-503733 | 2/2018 |
| JP | 2018-517913 | 7/2018 |
| WO | WO 1994/000831 | 1/1994 |
| WO | WO 2005/117621 | 12/2005 |
| WO | WO 2006/118654 | 11/2006 |
| WO | WO 2016/164484 | 10/2016 |
| WO | WO 2019/074942 | 4/2019 |
| WO | WO 2021/138193 | 7/2021 |
| WO | WO 2021/138195 | 7/2021 |
| WO | WO 2021/138464 | 7/2021 |

OTHER PUBLICATIONS

Exhaled Breath Analysis: from Occupation to Respiratory Medicine, 2005.

Harsanyi, G. "Chemical Sensors for Biomedical Applications," Biomedical Sensors, Chapter 7, pp. 323-326, Nov. 1, 2010, Momentum Press, LLC, New York, NY.

Henningfield, J.E. et al., "Expired air carbon monoxide accumulation and elimination as a function of number of cigarettes smoked," Addictive Behaviors, vol. 5, No. 3, pp. 265-272, Jan. 1, 1980.

Jarvis, M. J. et al. "Comparison of Tests Used to Distinguish Smokers from Nonsmokers," American Journal of Public Health, vol. 77, No. 11, Nov. 1987.

McMillan, A.S. et al., "Reflex inhibition in single motor units of the human lateral ptergoid muscle," Experimental Brain Research, 76: 97-102, 1989, Department of Oral Biology, University of British Columbia.

Navy Cyanide Test Kit (NACTEK), http://www.nrl.navy.mil/research/nrl-review/2004/chemical-biochemical-researchl deschamps/, accessed Oct. 26, 2010.

Piasecki, T. et al. "Self-monitored motives for smoking among college students," Psychology of Addictive Behaviors, vol. 21, No. 3, pp. 328-337, Oct. 2007.

(56) References Cited

OTHER PUBLICATIONS

Smokerlyzer Justification Guide, 2010.
Sung, M. et al., "Wearable feedback systems for rehabilitation," Journal of NeuroEngineering and Rehabilitation, 2:17, pp. 1-12, Jun. 2005.
Varshney, U. "Wireless Health Monitoring: Requirements and Examples," Pervasive Healthcare Computing: EMR/EHR, Chapter 5, pp. 89-118, Apr. 21, 2009, Spring Science+Business LLC.
Wu, W.H. et al., "MEDIC: Medical embedded device for individualized care," *Artificial Intelligence in Medicine*,42(2):137-152, Feb. 2008.

* cited by examiner

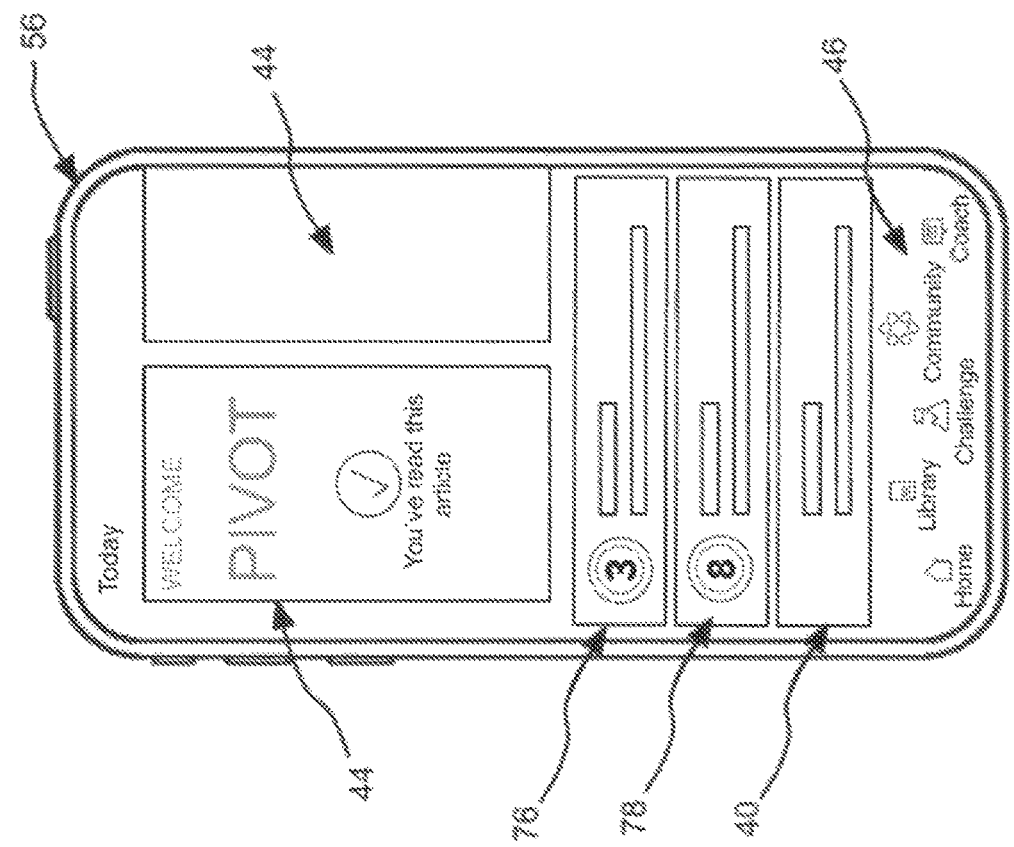
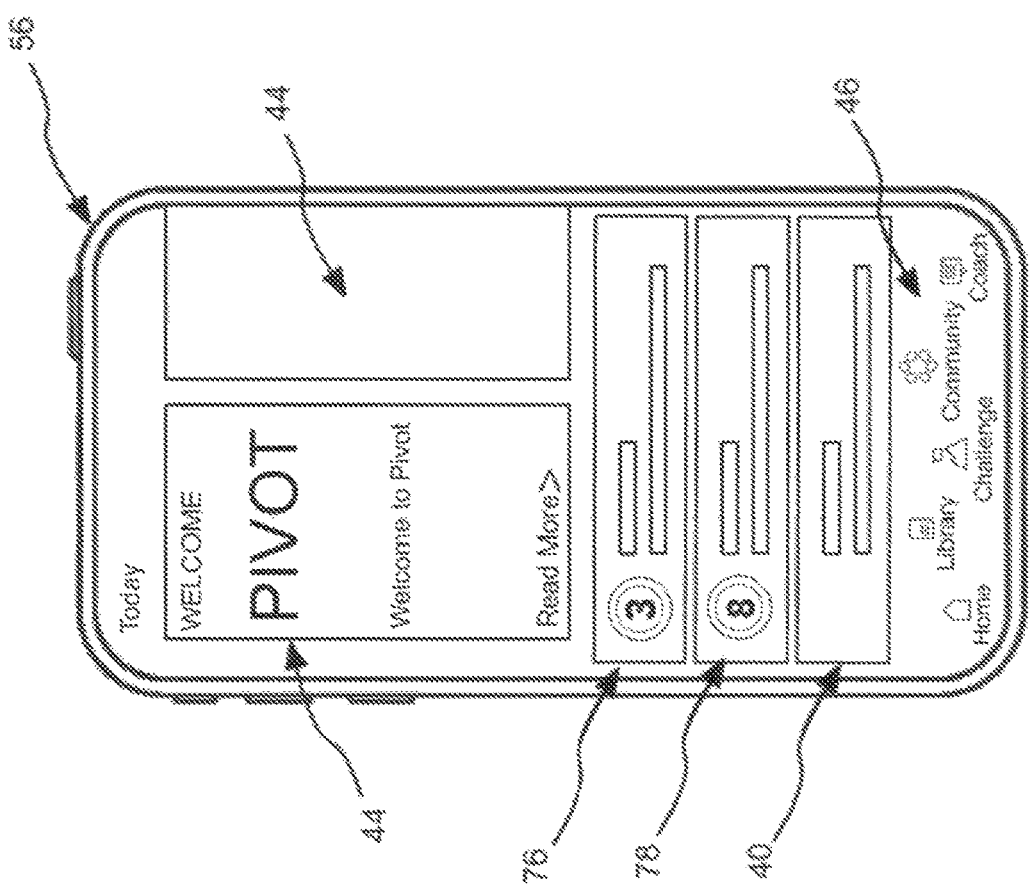
FIG. 7A
FIG. 7B

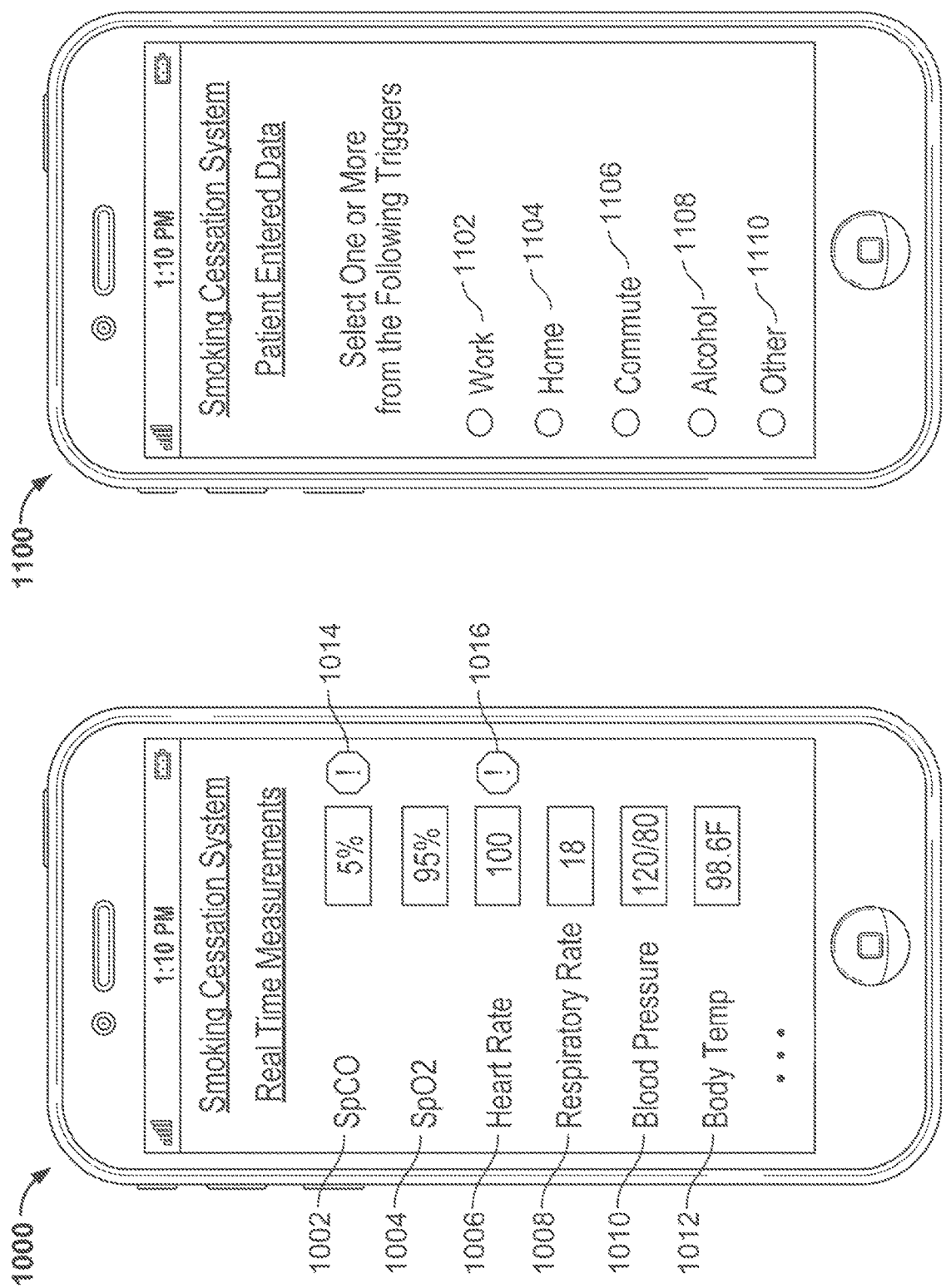

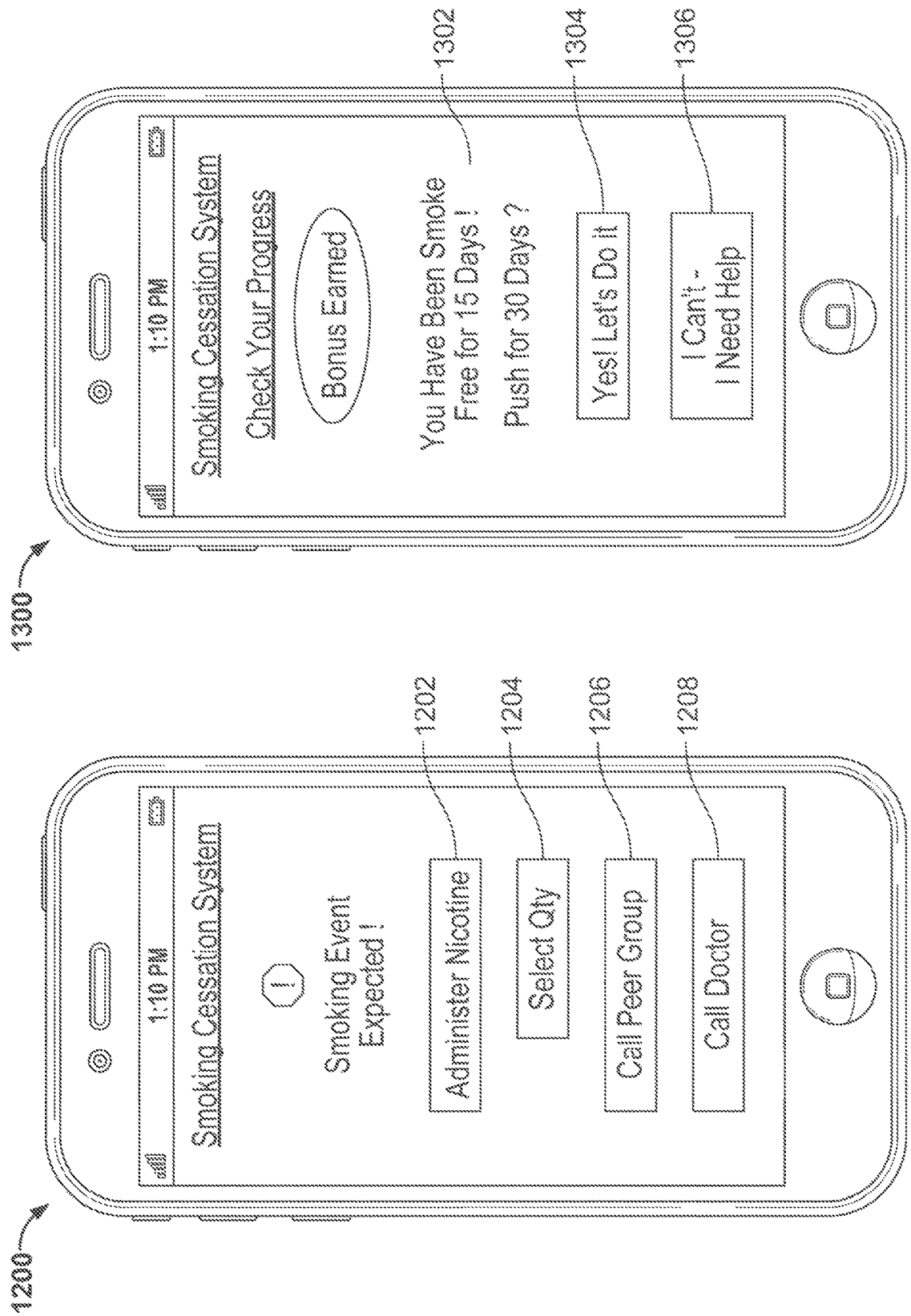

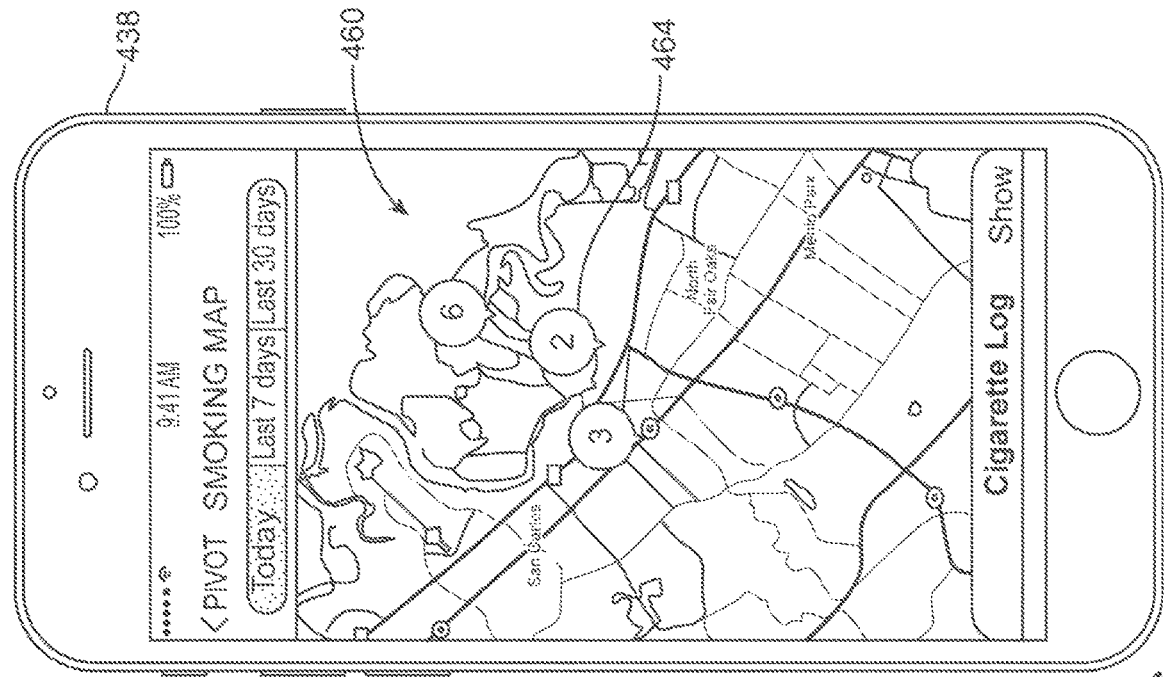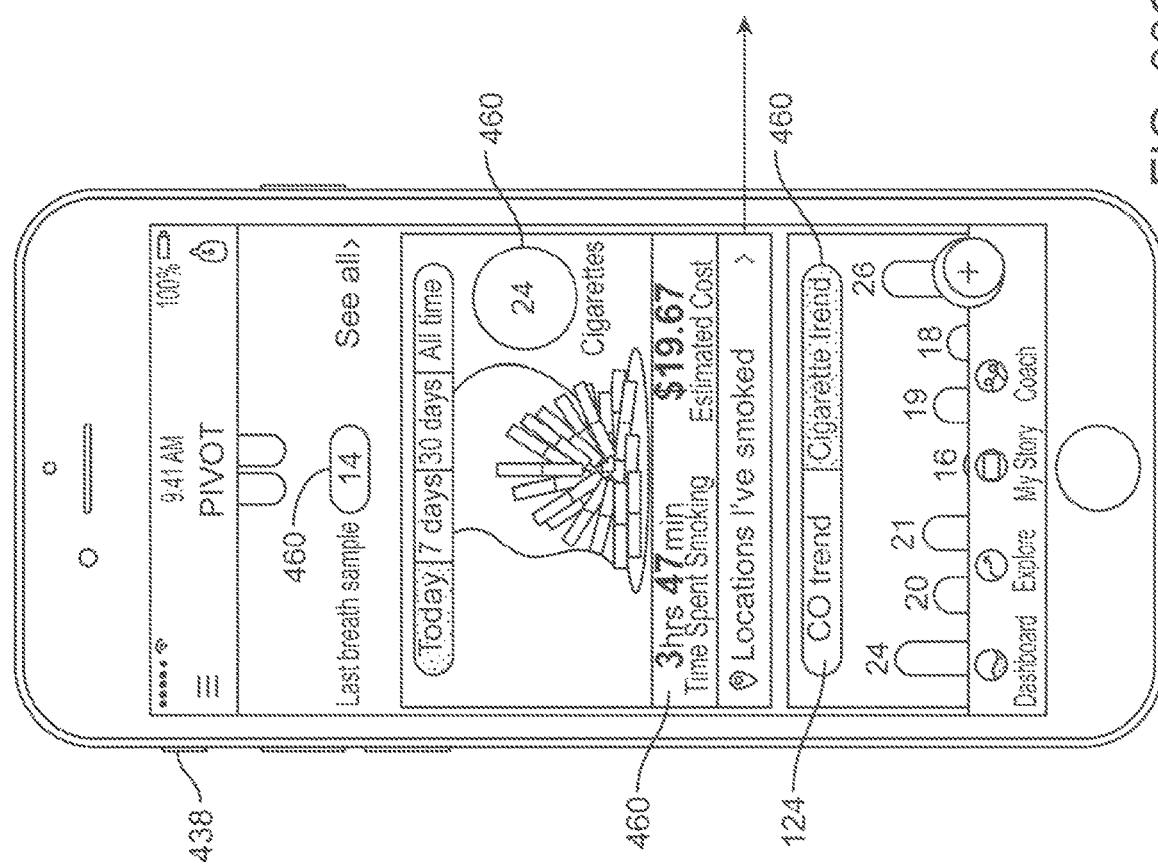
FIG. 33C

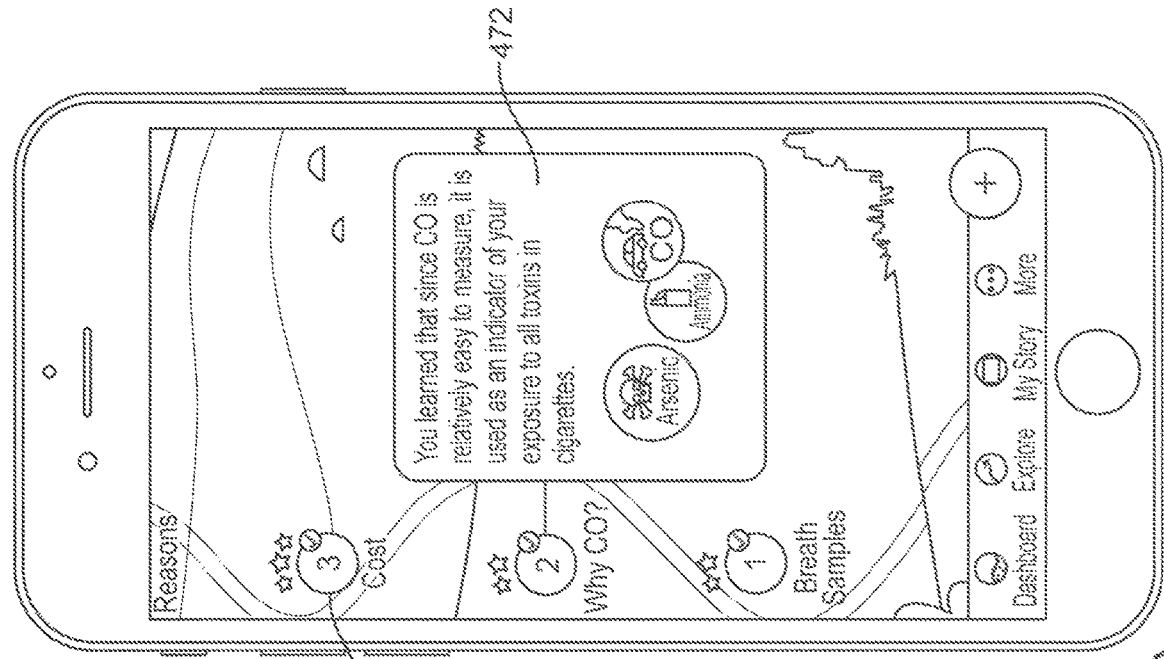
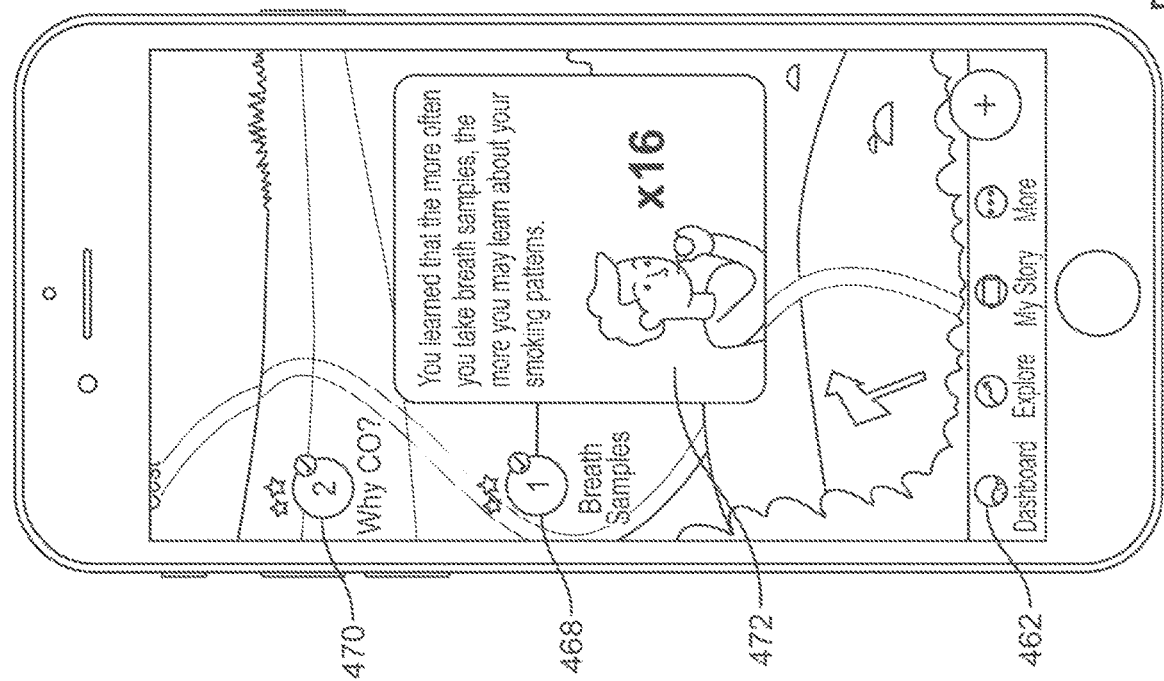
FIG. 33D

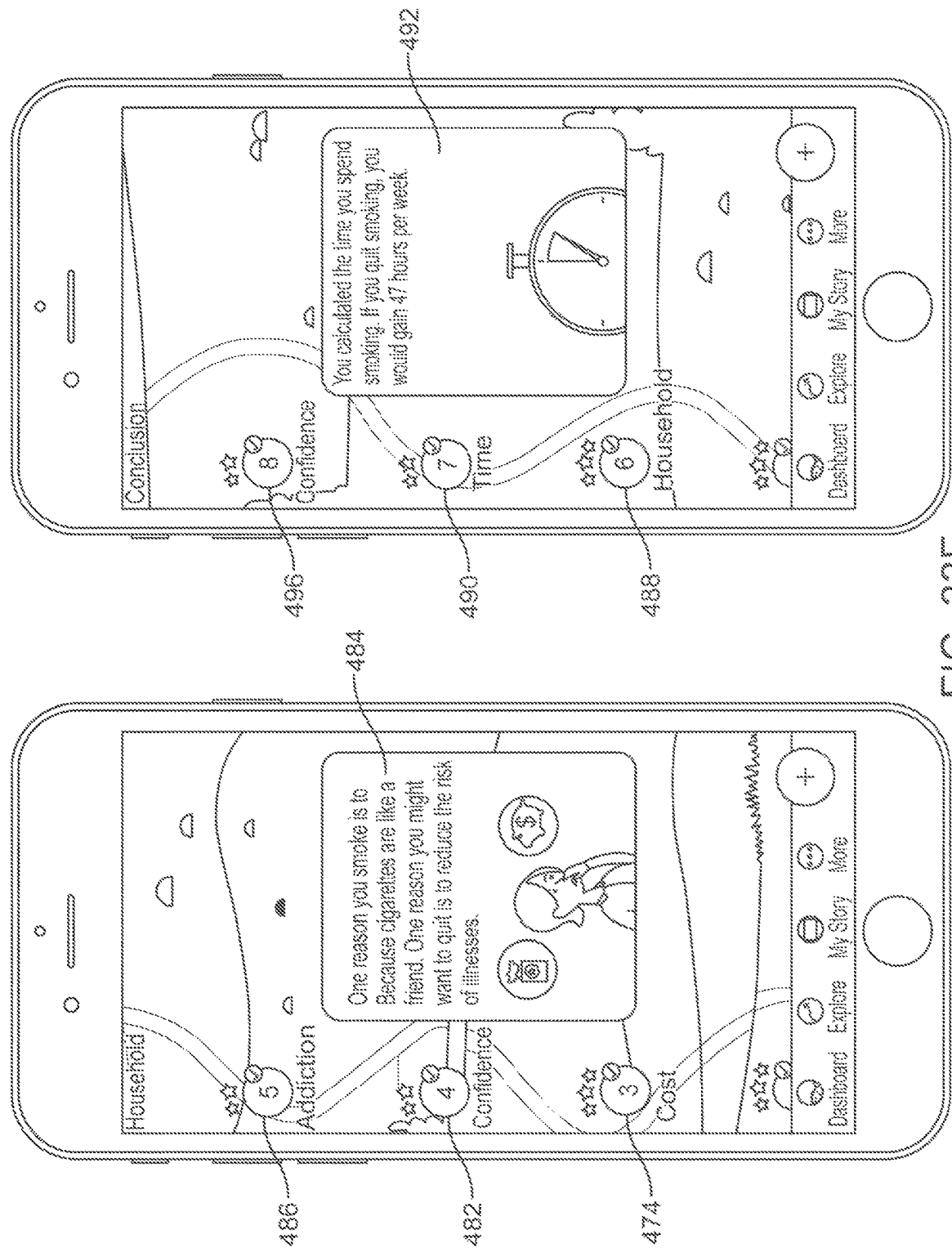

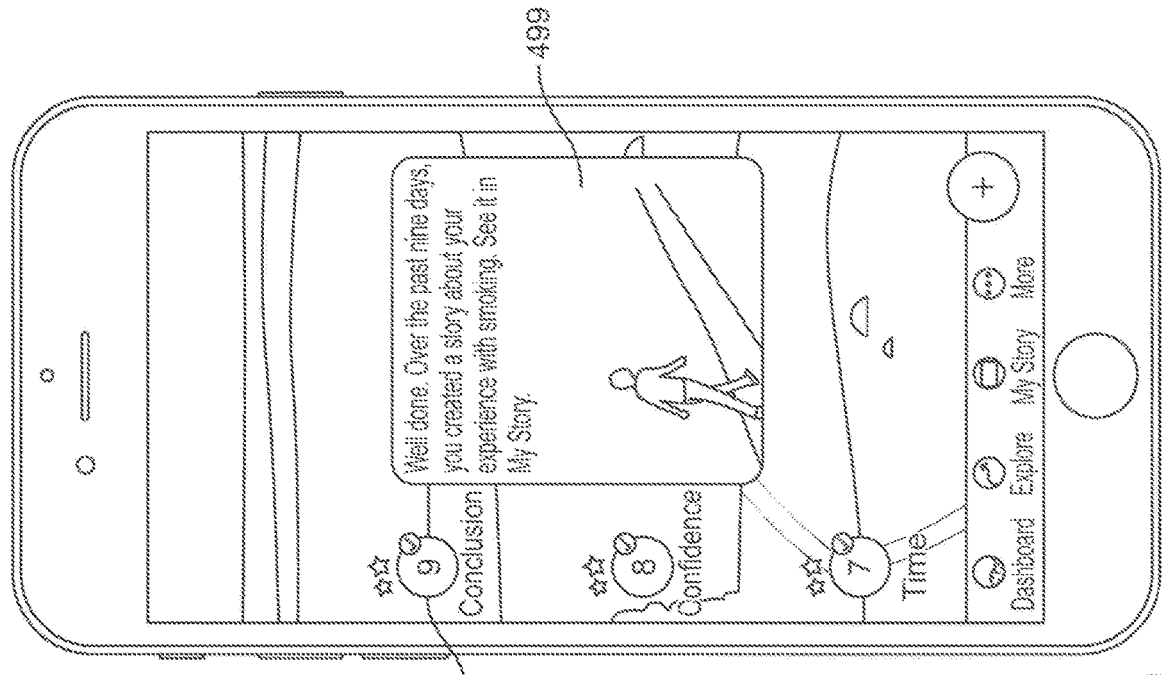
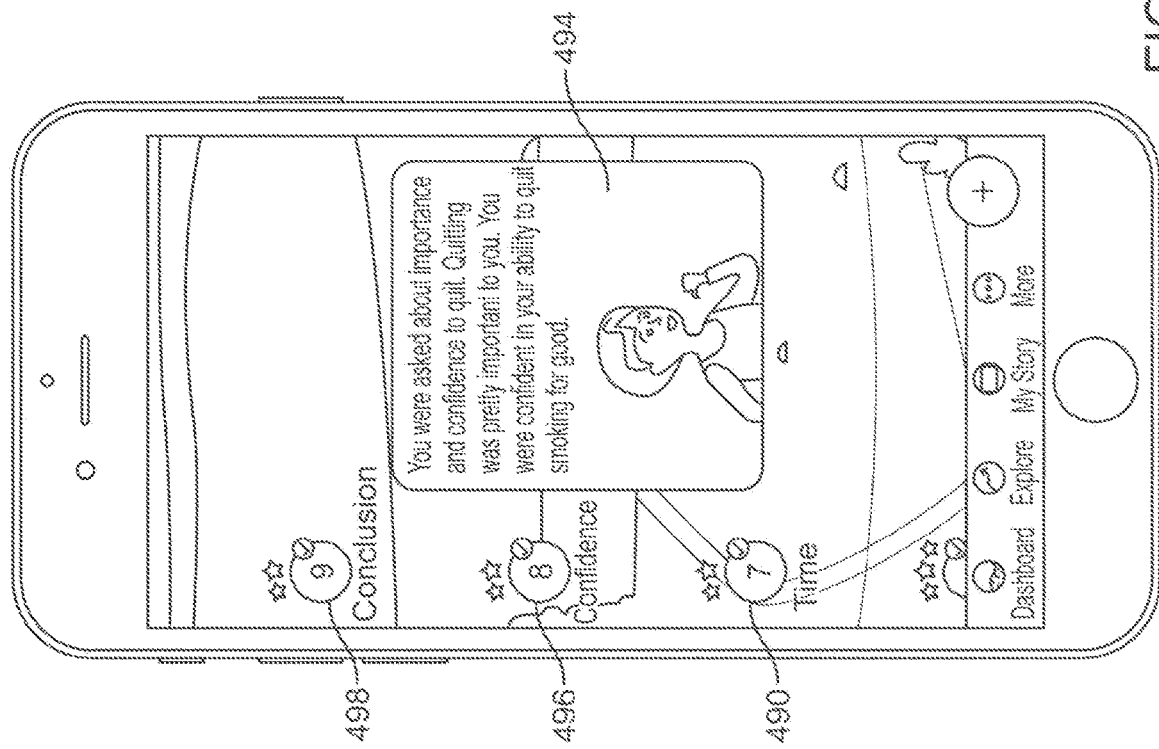
FIG. 33H

SYSTEMS AND METHODS FOR ASSISTING INDIVIDUALS IN A BEHAVIORAL-CHANGE PROGRAM

RELATED APPLICATION

This application is a continuation of U.S. patent application Ser. No. 17/138,491 filed Dec. 30, 2020, which claims benefit of priority to U.S. provisional application No. 62/955,214 filed Dec. 30, 2019; and 62/955,219 filed Dec. 30, 2019, and is related to International Patent Application No. PCT/US2020/067530, filed Dec. 30, 2020, the entirety of each of which are incorporated by reference.

FIELD OF THE INVENTION

The present disclosure relates to methods and systems of enhancing an electronic interaction between a behavioral-modification program and a user in the program by providing customized content specific to the user. The systems and methods allow for coach-counselor assistance to the individual-user or for automated content delivery.

BACKGROUND

Behavioral modification programs include those programs that attempt to assist an individual enrolled in or following the program (e.g., an individual-user) to lessen or cease undesirable behaviors in an attempt to improve physical and/or mental health. Many behavior modification programs attempt to change behavior or reduce undesired behaviors by means of techniques that include negative and positive reinforcement, imposing limitations, goal setting, and conditioning of the individual-user.

Because the success rate of behavioral modification programs is ultimately dependent on the actions of the individual-user in the program, providing support for those individual-users as they participate in the program is extremely important. Therefore, effective coaching can often improve success rates of such behavioral-modification programs.

In many cases, unhealthy behaviors are learned over significant time periods. Therefore, an individual who is attempting to unlearn such behaviors or who is attempting to alter future behaviors can face different levels of difficulty that vary depending on many factors specific to that individual-user. Therefore, any coach who attempts to assist that individual-user will be more effective if the coach can employ coaching techniques that incorporate information specific to that individual-user, whether that information is the individual's background or the individual-user's activity/behavior in the program. For example, an individual-user who is in an early stage of a behavioral-modification program can require a different type of coaching support than an individual-user who has completed a behavioral-modification program but remains engaged for continued compliance with the modified behavior. Moreover, coaching support for an individual-user that is strictly following the program will vary from the coaching support needed by another user that fails to remain in compliance with the program.

There remains a need to provide improved and effective coaching support for individual users of any behavioral modification programs. While the present disclosure discusses a smoking cessation program, the present disclosure can benefit any number of behavior modification programs, including but not limited to those programs that assist individuals with vaping cessation, nicotine addiction, weight loss, medication compliance, addiction, handling depression, increasing physical and/or mental activity, etc.

SUMMARY OF THE INVENTION

The system and methods described herein allow for assisting an individual in a behavioral-modification program through personalized coaching and personalized program feedback both of which are unique to either the individual user or the activity of the individual user in the program. In one example, the behavioral-modification program is a smoking cessation program. However, additional variations of the methods and systems described herein can be applied to any number of behavioral modification programs. Yet additional variations of the methods and systems disclosed herein include behavioral-modification programs that use biological feedback/measurements from the individual user.

The present disclosure includes methods of enhancing an electronic interaction between a coach-counselor assisting an individual-user participating in a behavioral-modification program. For example, such a method can include providing electronic access to a database of information during the electronic interaction between the coach-counselor and the individual-user, where the database of information includes a plurality of user-specific input data specific to the individual-user, where at least a portion of the plurality of user-specific input data is previously collected; electronically displaying a background data to the coach-counselor during the electronic interaction, where the background data includes a historical information regarding an activity of the individual-user in the behavioral-modification program, to permit the coach-counselor a review the historical information regarding the individual-user during the electronic interaction; electronically supplying the coach-counselor with at least one prompt of a communication topic from a database of generic information applicable to the behavioral-modification program, where the at least one prompt improves efficiency and accuracy of an interaction between the coach-counselor and the individual-user to provides a coaching topic for the coach-counselor to assist the individual-user in the behavioral-modification program; and electronically transmitting the at least one prompt to the individual-user as a coach-message.

Variations of the methods can include user-specific data that includes at least one of a subset of individual-user psychographic information, a subset of individual-user personal information, a subset of individual-user biological input data, and/or a combination thereof. In additional variations, the user-specific data includes a subset of individual-user biological input data with at least one of a subset of individual-user psychographic information and a subset of individual-user personal information, any additional information and/or a combination thereof.

Variations of the methods and systems described herein can include methods where electronically transmitting the at least one prompt occurs automatically without input from the coach-counselor. Alternatively, or in combination, electronically transmitting the at least one prompt requires an input from the coach-counselor.

Variations of the methods and systems can further require establishing an electronic reporting interface for the coach-counselor, where the electronic reporting interface allows the coach-counselor to electronically access a database of batch data that includes information from a plurality of users who participated in the behavioral-modification program.

The database of information can further include a behavior summary of the individual-user, where the behavior summary comprises an association of the biological input data from the individual-user with at least one of a plurality of behavioral data supplied by the individual-user where the behavioral data is non-biologic.

The database of information can be updated automatically by monitoring the user's activities and/or a coach-counselor can update the database of information about the individual-user.

In an additional variation, the subset of individual-user personal information in the database of information includes information from the group consisting of background, traits, demographics, and previous notes about the individual-user. Variations of the method can include a subset of individual-user psychographic information that includes milestones and targets of the user.

In variations of the method and systems displaying the data includes displaying a conversation history between the individual-user and the coach-counselor.

The prompts can be reusable prompts that are applicable to multiple alternate users. Additionally, or alternatively, the at least one prompt can comprise a partially written statement, wherein the coach-counselor must complete the partially written statement prior to sending the statement to the individual-user.

Variations of the methods include the coach-counselor to select at least one prompt, and wherein the at least one prompt comprises encoded variables that are pre-filled when the at least one prompt is selected by the coach-counselor.

The methods and systems described herein can include checks, such as where the prompt includes placeholders and the method further comprising preventing electronically transmitting the at least one prompt until coach-counselor replaces the placeholders with text.

Another variation of the method includes tagging the coach-message to assign a relevant category. The relevant category can include a trigger or a behavior.

In some variations, coach-message is added to the database of information about the user and can be made either private or public.

Additional variations of the method include enabling the coach-counselor to select data from the database of information comprises enabling the coach-counselor to search by content of the at least one prompt.

The prompts discussed herein can be altered to maintain stylistic similarity to the coach-counselor.

In additional variations, the method can further include selecting an automated message based on an inquiry from the individual-user and automatically transmitting the automated message to the individual-user.

The behavior modification programs disclosed herein can include preventing a behavior selected from the group consisting of smoking cigarettes, vaping, consuming alcohol, use of tobacco, use of narcotics.

The present disclosure also includes methods of providing customized content to an individual-user participating in a behavioral-modification program. An example of such a method includes providing a database of information comprised of a plurality of user-specific data specific to the individual-user, where at least a portion of the plurality of user-specific input data is previously collected; electronically monitoring an activity of the individual-user; using the activity to customize program-related content comprising an electronic media content from a database of generic information applicable to the behavioral-modification program; electronically transmitting the program-related content to the individual-user as an electronic message; and monitoring the individual-user's electronic interaction with the program-related content.

Again, variations of the methods can include user-specific data that includes at least one of a subset of individual-user psychographic information, a subset of individual-user personal information, a subset of individual-user biological input data, and/or a combination thereof. In additional variations, the user-specific data includes a subset of individual-user biological input data with at least one of a subset of individual-user psychographic information and a subset of individual-user personal information, any additional information and/or a combination thereof.

Variations of the method include an electronic message that further includes at least one data item from one of the subsets of individual-user psychographic information, the subset of individual-user personal information, or a subset of individual-user biological input data.

Electronically transmitting the program-related content to the individual user can occur automatically or can require an input from the individual user. In additional variations, the database of information further includes a behavior summary of the individual, where the behavior summary comprises an association of the biological input data from the individual with at least one of a plurality of behavioral data supplied by the individual where the behavioral data is non-biologic.

The subset of individual-user personal information in the database of information can include information from the group consisting of background, traits, demographics, and previous notes about the individual-user. The subset of individual-user psychographic information in the database of information can include milestones and targets.

The methods can further include adding the program-related content to the database of information about the user. In additional variations, enabling the coach-counselor to select data from the database of information comprises enabling the coach-counselor to search by content of the at least one prompt.

This application is related to the following commonly assigned patents and applications. Such patents include U.S. Pat. No. 10,306,922 issued on Jun. 4, 201; U.S. Pat. No. 9,861,126 issued on Jan. 9, 2018; U.S. Pat. No. 10,674,761 issued on Jun. 9, 2020; U.S. Pat. No. 10,206,572 issued on Feb. 19, 2019; U.S. Pat. No. 10,335,032 issued on Jul. 2, 2019; U.S. Pat. No. 10,674,913 issued on Jun. 9, 2020, and U.S. Pat. No. 10,306,922 issued on Jun. 4, 2019. Such applications include: Ser. No. 16/889,617 published as US20200288785 on Sep. 17, 2020; Ser. No. 15/782,718 published as US20190113501 on Apr. 18, 2019; and Ser. No. 16/890,253 published as US20200288979 on Sep. 17, 2020. The entirety of each of the above patents and applications is incorporated by reference.

BRIEF DESCRIPTION OF THE DRAWINGS

FIGS. 7A and 7B also illustrate informational data cards, which are selected to provide personalized information specific to the user.

FIG. 18 depicts an illustrative smart phone app screen showing measurements such as SpCO, SpO2, heart rate, respiratory rate, blood pressure, and body temperature in accordance with some embodiments of the disclosure.

FIG. 19 depicts an illustrative smart phone app screen for receiving patient entered data in accordance with some embodiments of the disclosure.

FIG. 20 depicts an illustrative smart phone app screen implementing a smoking prevention protocol in accordance with some embodiments of the disclosure.

FIG. 21 depicts an illustrative smart phone app screen for presenting the quit process as a game for the patient in accordance with some embodiments of the disclosure.

FIGS. 33A-33H illustrate another variation of the systems and methods described above used to implement a treatment plan for identifying a smoking behavior of an individual for ultimately assisting the individual with smoking cessation and maintaining the individual's status as a non-smoker.

DETAILED DESCRIPTION OF THE INVENTION

The present disclosure includes methods for enhanced coaching of an individual-user that is participating in a behavioral-modification program. The coaching can occur using an actual coach, who is an individual that is trained to assist the user during the program. Alternatively, or in combination, coaching can include automated electronic communication either pushed or requested by the individual, where the automated electronic communication can provide repeated interaction with the individual-user to maintain engagement with the program. As noted herein, the coaching includes customized information as well as generic information. For example, customized information is information that is intended to specifically apply to an individual user based on any number of criteria unique to that user. While generic information can comprise information that applies to one or more users regardless of their specific situation.

In a first variation, the methods and systems for enhanced coaching of an individual are discussed specific to a smoking cessation program. However, the methods and systems can apply to any behavioral-modification program intended to increase a health of the individual and/or a well-being of the user.

Figure 1:
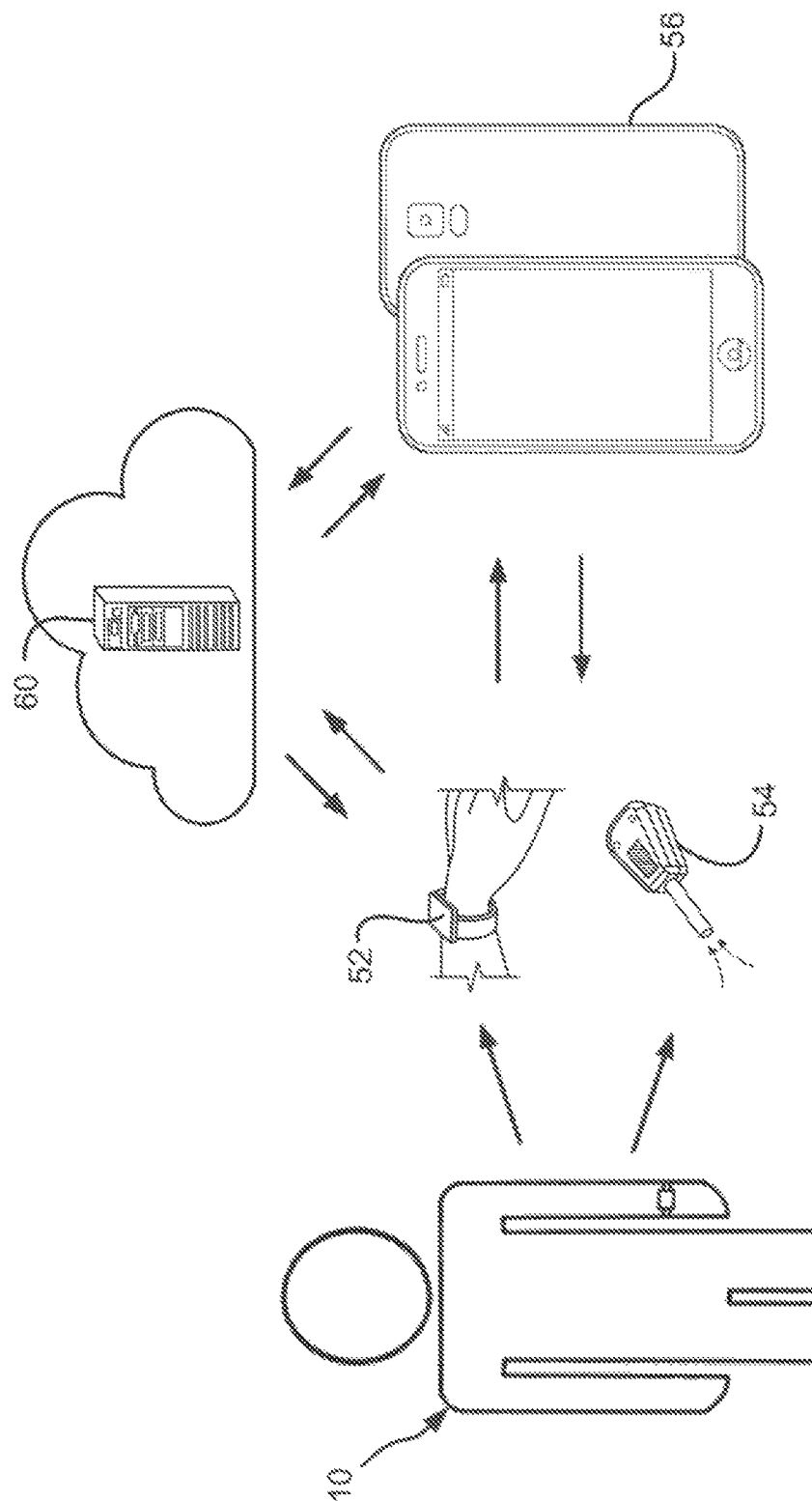
FIG. 1 depicts an individual-user employing an electronic personal device that is configured to provide biological data/measurements from the individual.

The behavioral-modification programs described herein rely on electronic communication to facilitate exchange of information between an individual-user 10 and the behavioral modification program (e.g., the program's computer/database systems and/or a live coach.) For example, FIG. 1 represents an illustration of an individual-user 10 employing an electronic personal device that is configured to provide biological data/measurements from the individual. While the method and systems include any personal electronic device capable of providing biological data/measurements, for purposes of illustration, FIG. 1 shows a smart watch 52 or breath sensor 54 that can be used to communicate biological data to a cloud server 60 either directly or through any intermediary device such as a smart-phone 56 or other personal computing device. In the variation discussed below, which provides a smoking cessation program as the behavioral-modification program, the user 10 employs a portable device 56 that obtains a plurality of samples of exhaled air from the individual with sensors that measure an amount of carbon monoxide within the sample of exhaled air (also referred to as exhaled carbon monoxide or ECO). The biological input data can comprise data measured by a device (e.g., exhaled breath via device 54). Alternatively, or in combination, the biological data can comprise data that is entered manually by the user 10 as will be discussed below.

Figure 2A:
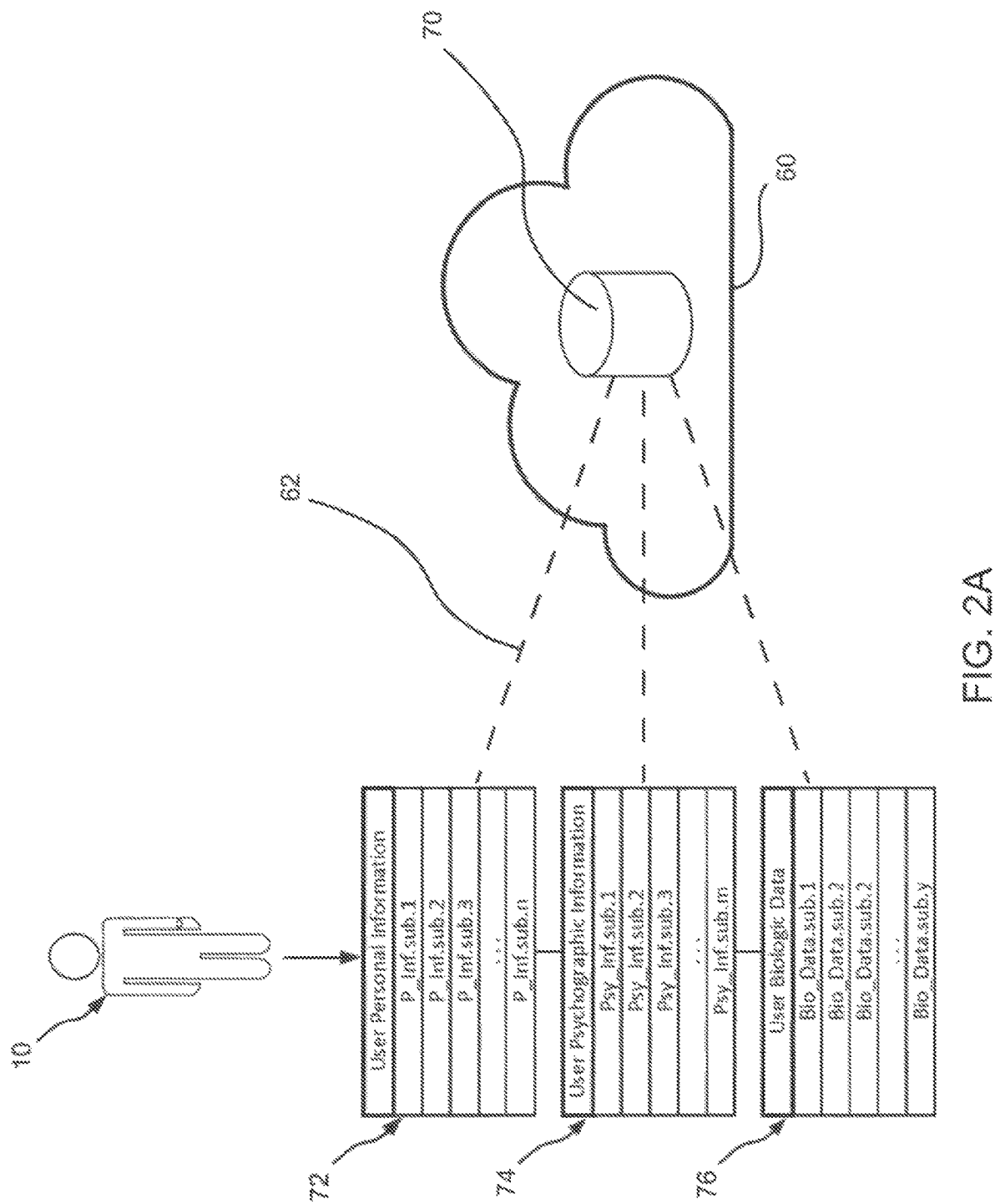
FIG. 2A illustrates the methods and systems for enhanced coaching of an individual require building and/or compiling one or more databases that include information specific to the user.

In a first variation, as conceptually illustrated in FIG. 2A, the methods and systems for enhanced coaching of an individual requires building and/or compiling one or more databases 70 that includes information specific to the user 10. This data can include, but is not limited to, data subsets (e.g., 72, 74, 76) that builds one or more databases 70. In some variations, submission of biologic data 76 will not occur until a user is engaged with the program.

The transmission 62 or entering of the data 72, 74, 76, into the one or more databases 70 can occur via any number of methods. For example, the data 72, 74, 76 can be compiled prior to or during the initial stages of a behavioral-modification program by one or more individuals associated with the program. Alternatively, or in combination, the user 10 can some or all of the data 72, 74, 76 using an electronic interface. The user-specific database 70 (which may include one or more databases) can be compiled and/or updated over any timeframe. However, the behavioral-modification program can establish a minimal level of information required to start or enroll the individual in the program. While FIG. 2 illustrates data transmission 62 to a cloud or cloud server 60, variations of the method and systems within this disclosure can include local storage of the database.

Figure 2B:
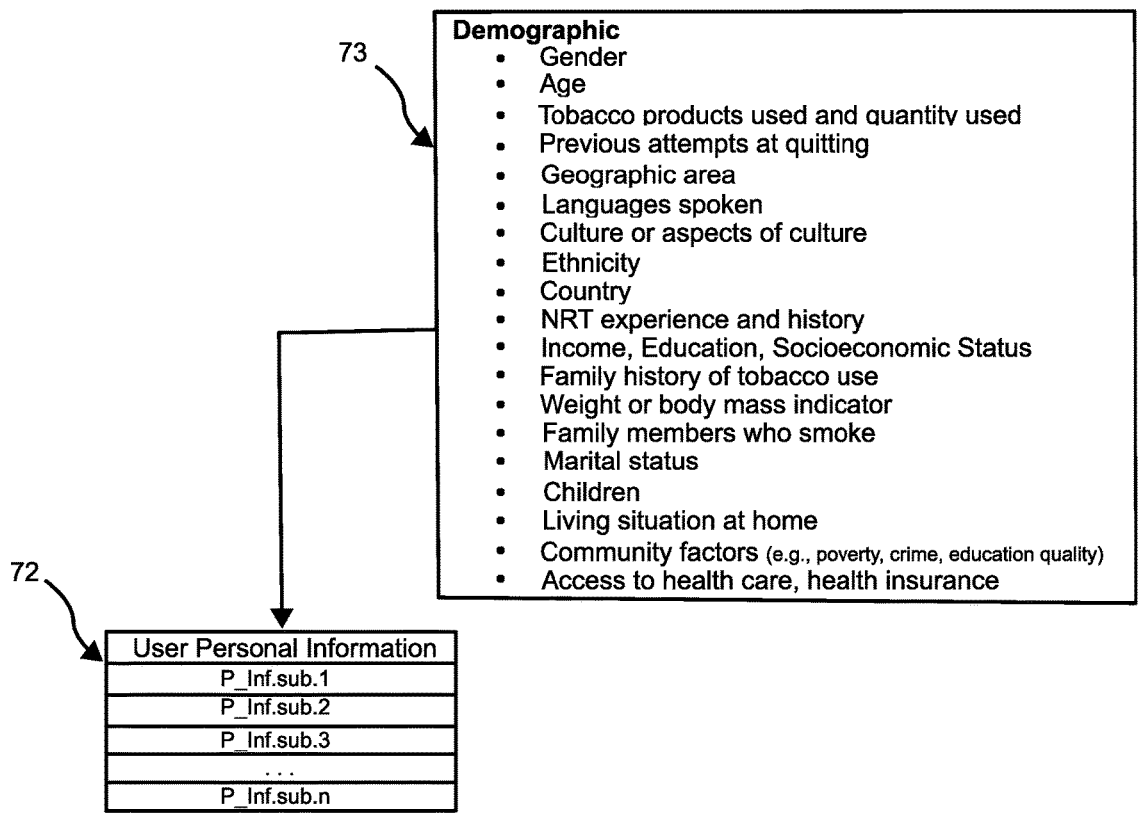
FIGS. 2B and 2C illustrate non-exhaustive lists of inputs that drive data subsets 72, 74 building one or more databases of information specific to the individual-user.
Figure 2C:
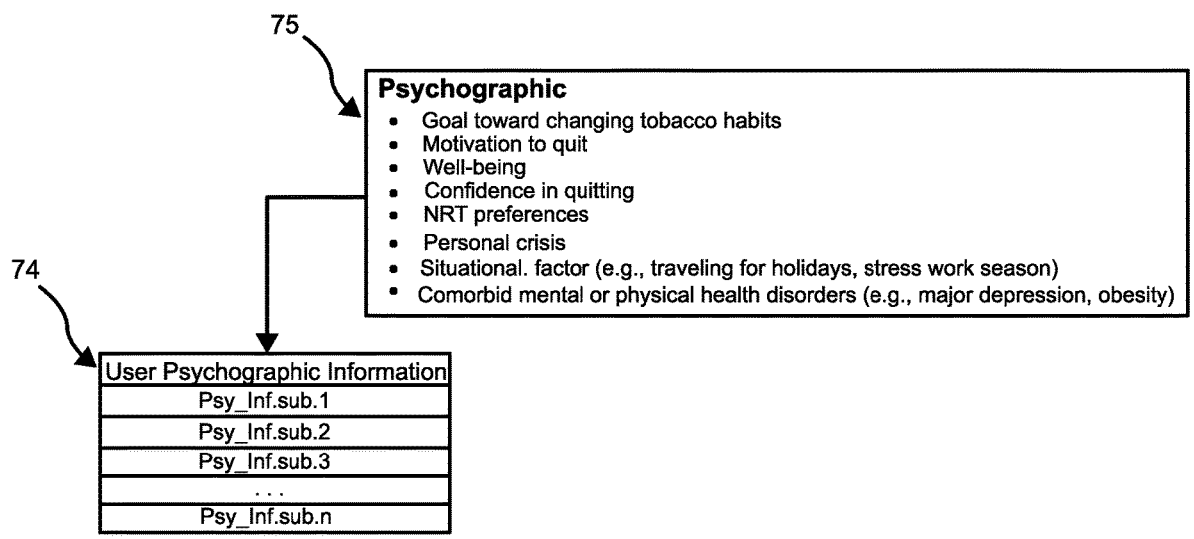

FIGS. 2B and 2C illustrate non-exhaustive lists of inputs 73, 75 that drive the data subsets 72, 74 for building one or more databases of information specific to the individual-user. As shown, in FIG. 2B user personal information 72 can comprise information, in this example, demographic information. Typically, such user personal information 72 comprises information specific to a history or identity of the individual user. Such informational inputs include, but are not limited to: gender, age, tobacco products used and quantity used, previous attempts at quitting, geographic area, languages spoken, culture or aspects of culture, ethnicity, country, nicotine replacement therapy experience and history, income, education, socioeconomic status, family history of tobacco usage, weight or body mass indicator, family members who smoke, marital status, children, living situation at home, community factors (e.g., poverty, crime, education quality), access to health care, and health insurance.

FIG. 2C shows an example of a number of inputs 75 that can be used to collect a specific subset of data comprising psychographic information of the individual user. The psychographic inputs 75 allow for building a database of psychographic information 74 allowing for the study and classification of the individual-user according to his/her attitudes, aspirations, and other psychological criteria, in relation to the behavioral-modification program. Again, why the psychographic inputs will vary depending upon the specific behavior-modification program, in a smoking cessation program, such psychographic inputs 75 can include, but are not limited to, goal toward changing tobacco habits; motivation to quit; well-being; confidence in quitting; nicotine-replacement-therapy preferences; personal crisis; situational factor (e.g., traveling for holidays, stressful work season); and comorbid mental or physical health disorders (e.g., major depression, obesity).

Figure 3A:
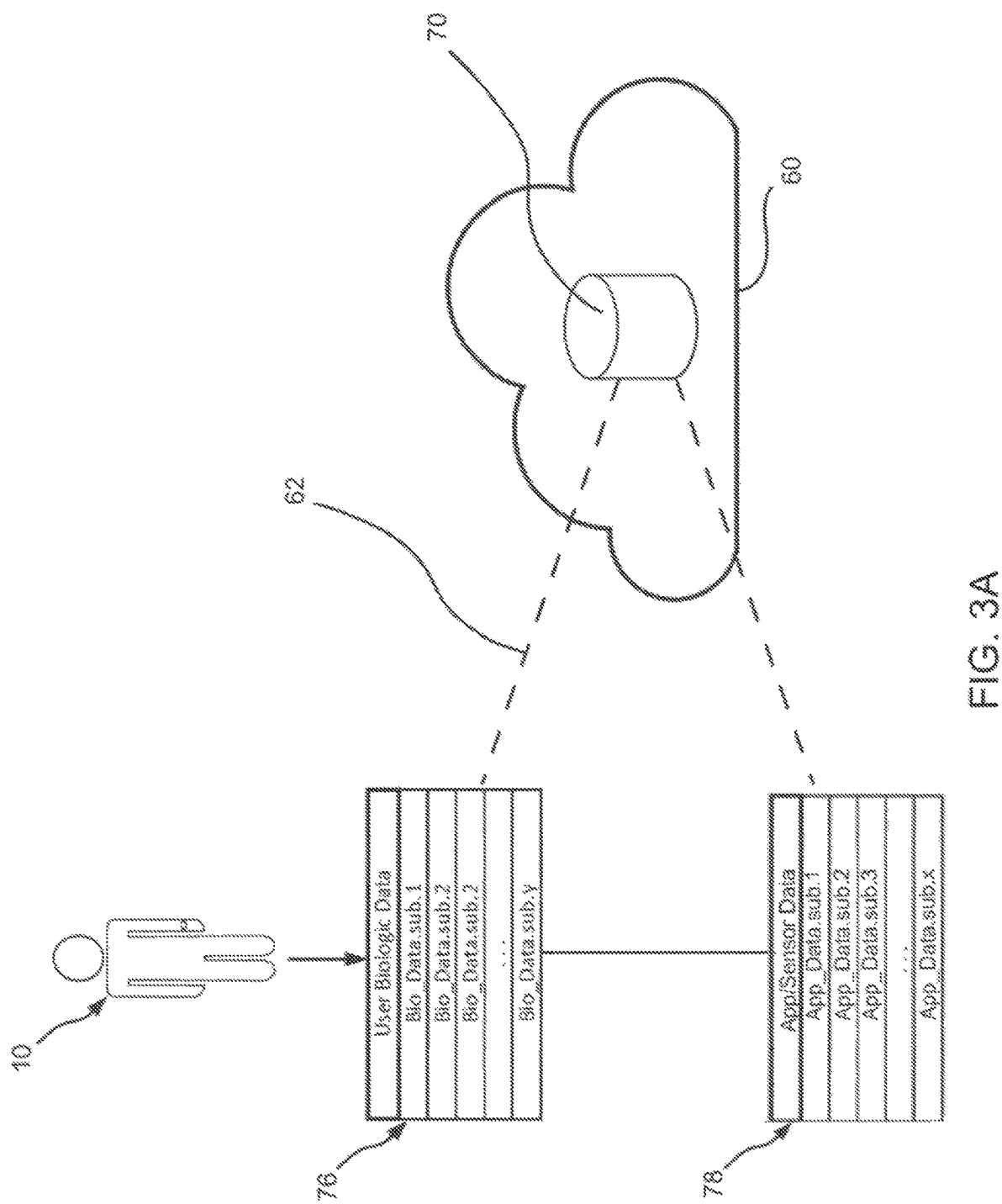
FIG. 3A represents compiling one or more databases using additional subsets of biologic data as well as application, apps, and/or sensor data.

FIG. 3A represent a condition where the one or more databases are compiled using additional subsets of biologic data 76 as well as application, apps, and/or sensor data 78. As noted above, the use of additional biologic data 76 and app/sensor data 78 often occurs during participating of the user 10 in the behavior-modification program and after the database is compiled as illustrated in FIG. 2A. However, the methods and systems described herein can include any sequence of compiling the database(s).

Figure 3B:
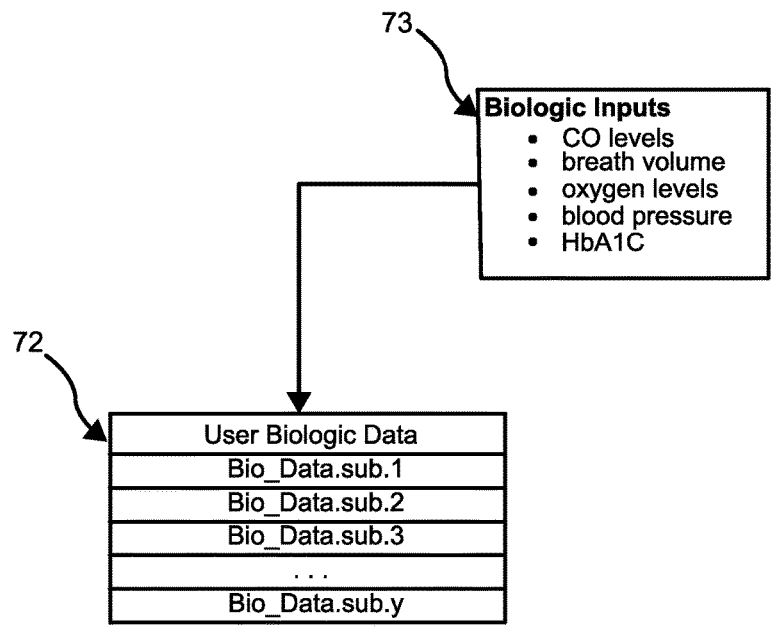
FIGS. 3B and 3C represent various inputs used to produce biologic and app/sensor data subsets.
Figure 3C:
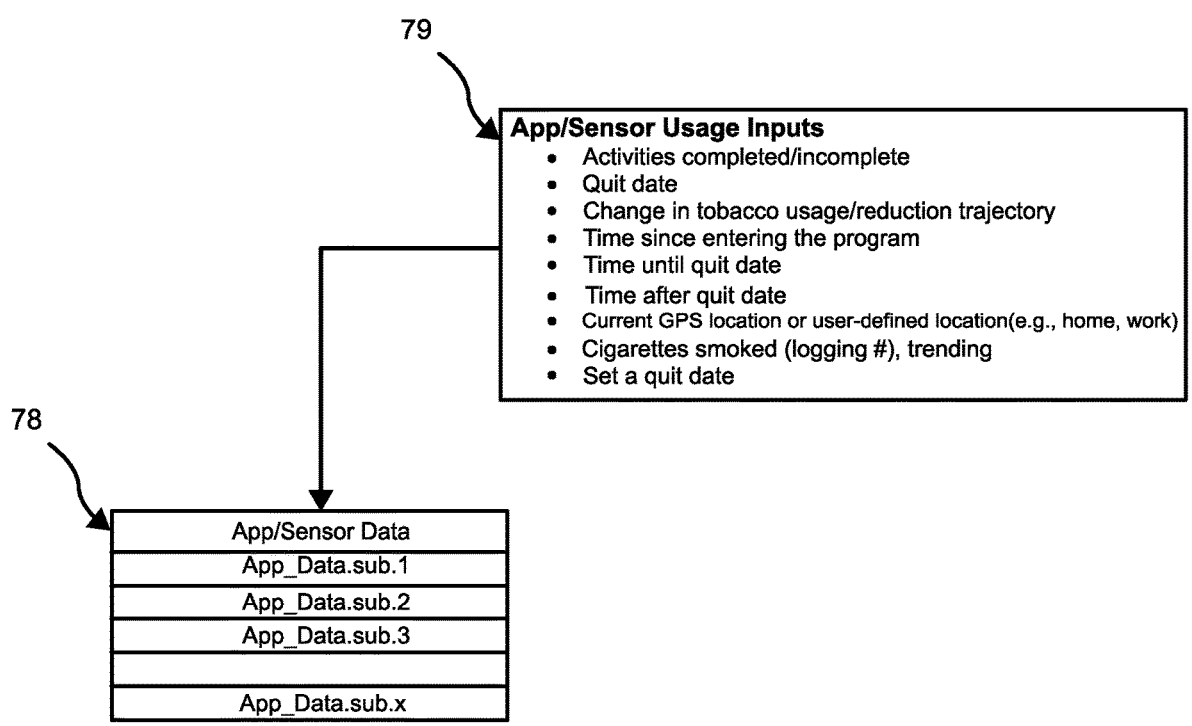

FIGS. 3B and 3C represent various inputs 77, 79 used to produce biologic 76 and app/sensor 78 data subsets. The biologic inputs 77 can be any input related to the user. Typically, the biologic data is entered using a personal device (e.g., 52 and/or 54 as shown in FIG. 1). However, the biologic data 76 can be produced or measured in any manner required by the particular data that are useful to the behavior-modification program. Examples of biologic inputs 77 for use in a smoking-cessation behavioral modification program, include but are not limited to: carbon monoxide (CO) levels; breath volume; oxygen levels; blood pressure; and hemoglobin A1c measurements. It is noted that the application data 78 can include data that is actively submitted by the user or data that is passively recorded by the system (e.g., duration in the program, time between participation in the program, etc.)

Figure 4:
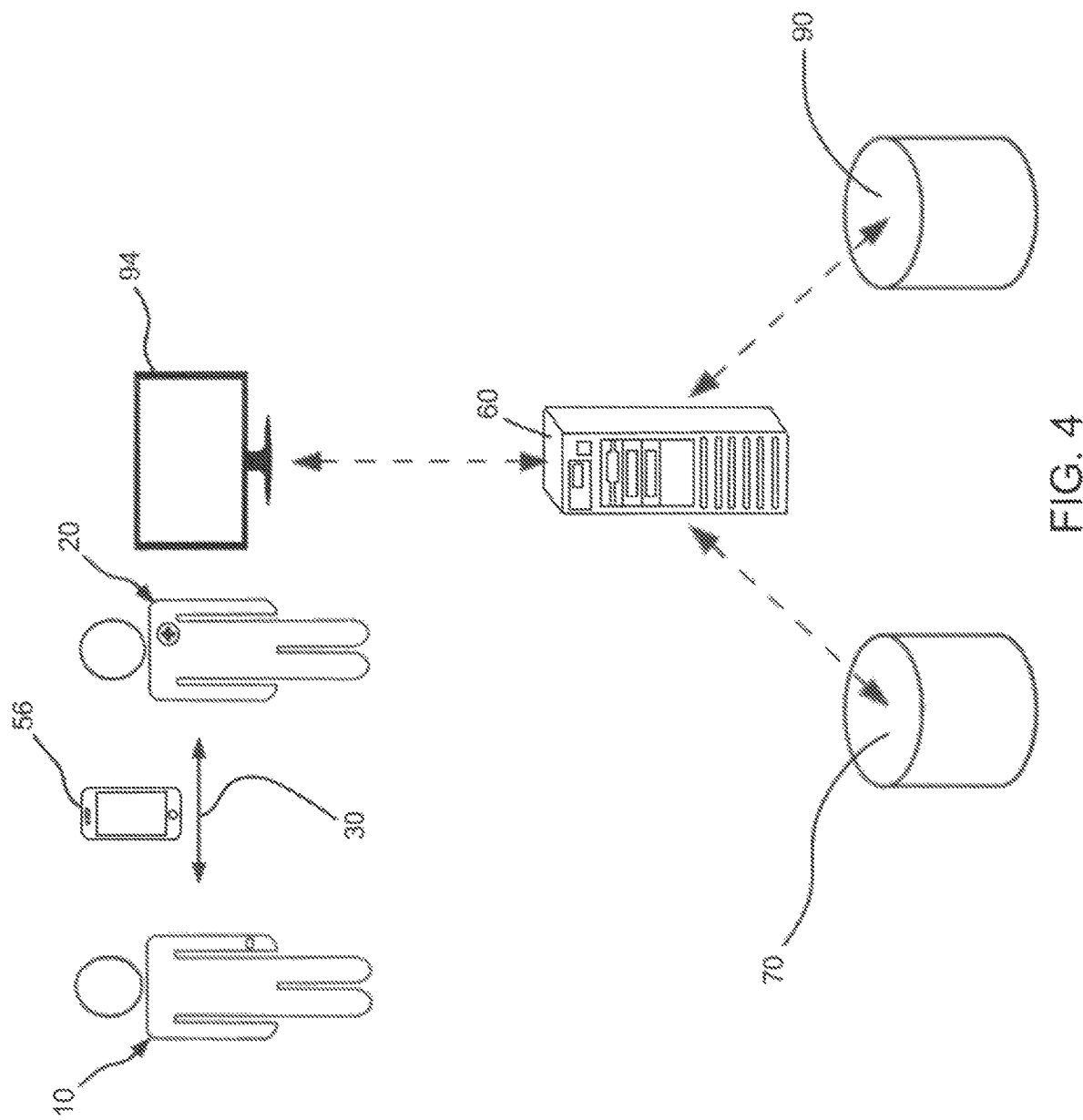
FIG. 4 illustrates a conceptual electronic interaction between a counselor-coach attending to an individual user that is participating a behavior-modification program.

FIG. 4 illustrates a conceptual electronic interaction 30 between a counselor-coach 20 attending to an individual user 10 that is participating a behavior-modification program. As illustrated, the electronic interaction 30 can occur via one or more electronic devices 56. While the present methods and systems also contemplates in-person or real-time voice or messaging communication, electronic interactions 30 allow for an on-demand system of coaching. The coach-counselor 20 will access via an electronic device 94 to a server/system 60 that improves and enhances the interaction with the user 10. The server/system 60 is able to draw from one or more databases 70 that contain user-specific data as discussed above. This configuration permits the coach-counselor 20 to access a wide variety of data that will be helpful to the coach-counselor 20 to provide meaningful support to the individual-user 10. For example, the server/system 60 can display a plurality of user-specific data specific to the individual-user received from a database 70, where the user-specific data includes any of a subset of individual-user psychographic information, a subset of individual-user personal information, or a subset of individual-user biological input data. The system 60 can also provide the coach-counselor 20 with any background data comprising a historical information regarding the individual-user's activity in the behavioral-modification program, to permit the coach-counselor a review the historical information regarding the individual-user during the electronic interaction. Typically, such background data includes the app/sensor usage inputs 79 (shown in FIG. 3C). However, background data can also include information from a previous session between the coach-counselor 20 and user 10. The ability to provide a wide variety of data specific to the user allows for any number of coach-counselors 20 to have familiarity with the user 10.

Another feature of the system 60 is the ability to draw information from one or more databases 90 that contain information that is specific to the behavioral-modification program. For example, the system 60 can electronically supply the coach-counselor 20 with at least one prompt of a communication topic from the database 90, where the prompt or communication topic is generic information applicable to the behavioral-modification program. where the at least one prompt improves efficiency and accuracy of an interaction between the coach-counselor and the individual-user. The coach-counselor 20 will have the ability to electronically transmit 30 a message comprising one or more prompts to the individual-user 10. In additional variations, the coach-counselor 20 will have the option of customizing the prompts prior to discussing or sending to the user 10.

Figure 5A:
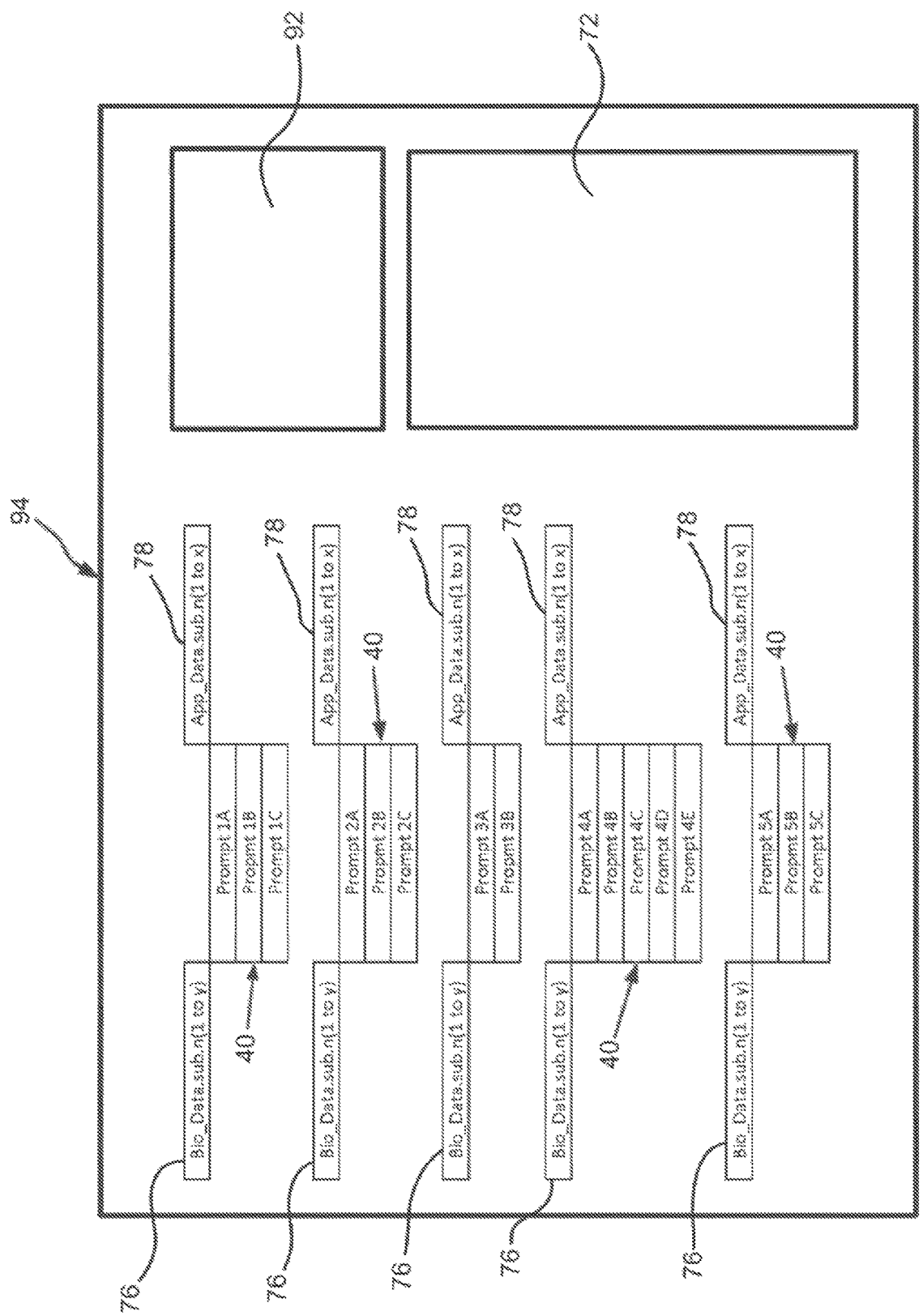
FIG. 5A illustrates one example of a display, such as via an electronic display, of information provided to a coach-counselor to enhance an interaction when assisting an individual-user during a behavioral-modification program.

FIG. 5A illustrates one example of a display, such as via an electronic display 94, of information provided to a coach-counselor to enhance an interaction when assisting an individual-user during a behavioral-modification program. FIG. 5 is intended to show a variation of the information that can be relayed to a coach-counselor. However, any variation of data subsets can be provided as needed depending on the behavioral-modification program.

FIG. 5A illustrates a display 94 providing a plurality of biologic data in association with behavioral input of the individual, typically comprising application, apps, and/or sensor data 78 as previously discussed. The system submits one or more prompts 40 based on a comparison of the biological data and the behavioral data 78. FIG. 5 shows biological data 76 comprising $Bio\_Data.sub.n(1\ to\ y)$, which means that the displayed biologic data 76 can comprise any information that is in the database discussed above. Likewise, the display can show the same or a variety of different biological data 76. The methods and systems described herein compare various biological data 76 to behavioral data 78 to generate prompts 40 for use by the coach-counselor in assisting the specific user. As noted above, the behavioral data 78 can include background or other data specific to the individual such as a historical information regarding the individual-user's activity in the behavioral-modification program. The prompts 40 can be drawn from information in one or more databases (90 in FIG. 4) that is specific to the behavioral-modification program. Such information can be generic information applicable to the behavioral-modification program. The goal of the prompts is to improve efficiency and accuracy of an interaction between the coach-counselor and the individual-user and to provides a coaching topic for the coach-counselor to assist the individual-user in the behavioral-modification program.

FIG. 5A also shows the display providing additional information such as information 90 that is generic to the individual but related to the program as well as personal information 72 regarding the user. Additional variations of the systems and methods described herein can include display of any relevant information to the coach-counselor and/or user. Such information includes but is not limited to information related to the user, related to the program, or unrelated to either the user and/or the program.

Figure 5B:
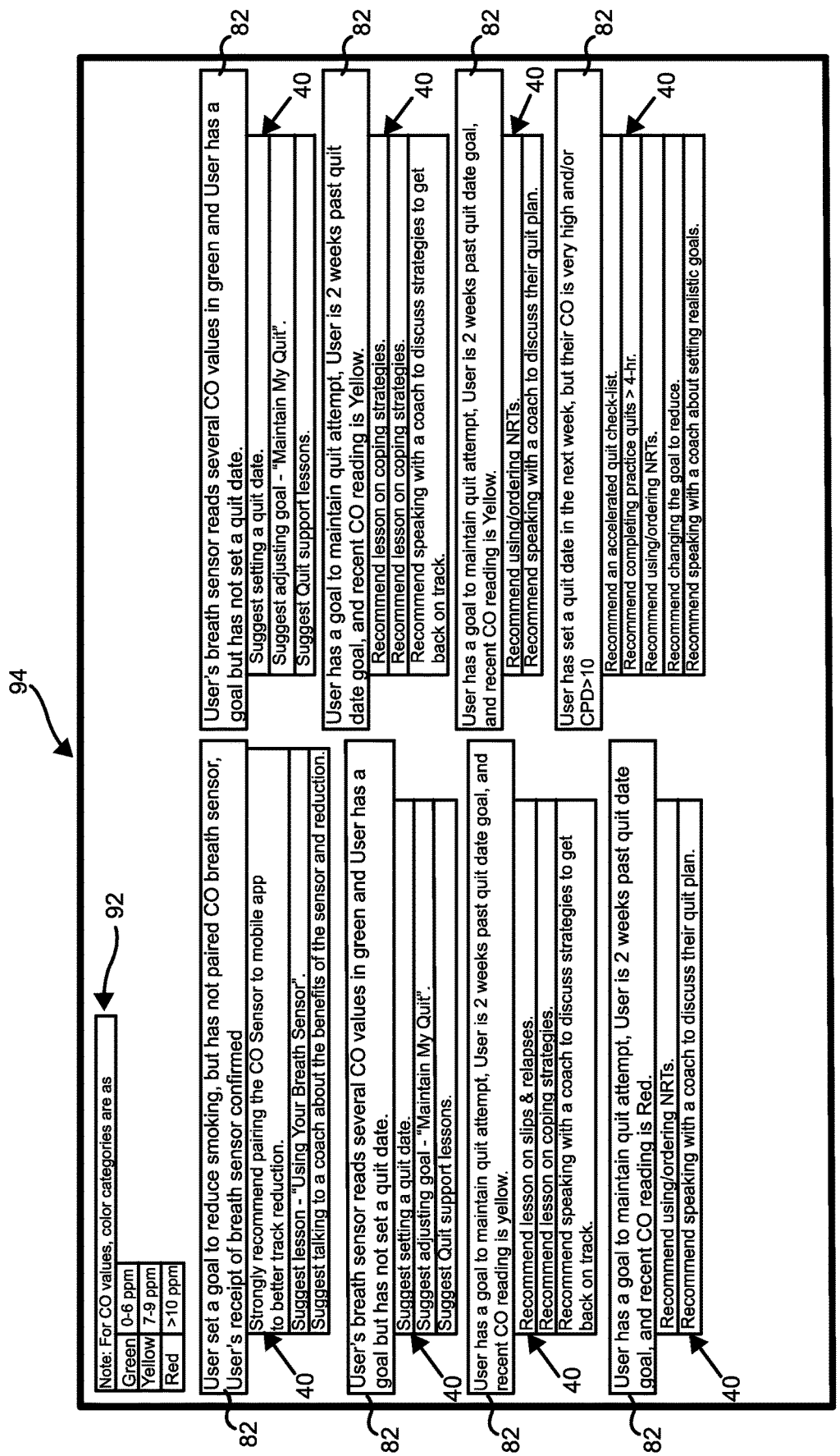
FIGS. 5B and 5C illustrate one variation of a display in accordance with the display discussed in FIG. 5A where a coach-counselor has access to information intended to improve an interaction with a user.
Figure 5C:
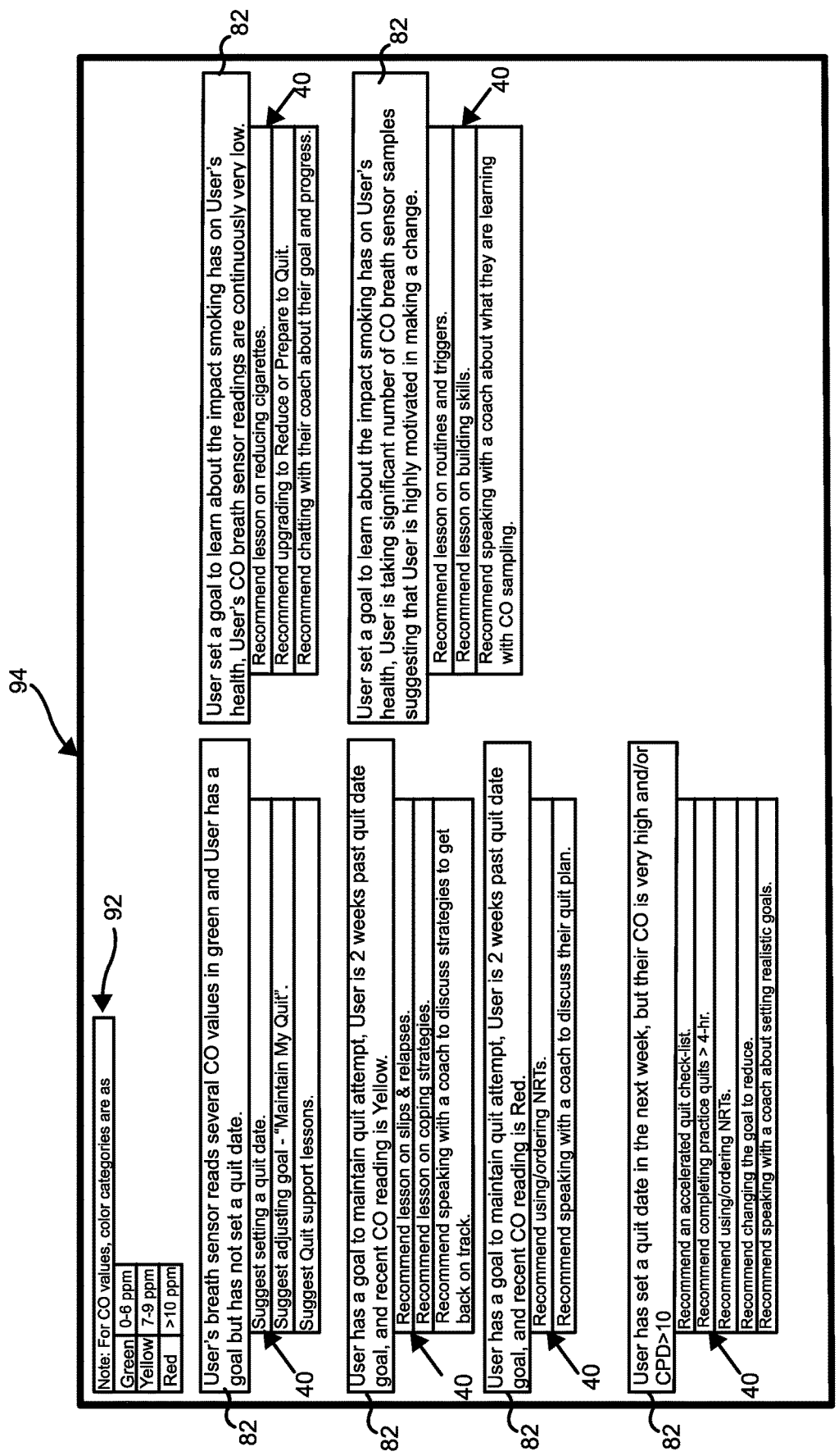

FIGS. 5B and 5C illustrate one variation of a display 94 in accordance with the display discussed in FIG. 5A where a coach-counselor has access to information intended to improve an interaction with a user. As noted herein, the display 94 can include information that is specific to the individual user. In the illustrated examples, the display includes a combination 82 of biologic data with application, apps, and/or sensor data along with prompts 40 associated with the specific combination of information 82. In the first example on the left, the combination 82 information informs the coach that the user already a goal to reduce smoking but has yet to pair a CO breath sensor for submission of information, the information also indicates that the user received the breath sensor. Again, such information can be a combination of previously submitted data from a database specific to the user (e.g., database 70 discussed above). This combination data comprises a background data of historical information regarding the individual-user's activity in the behavioral-modification program. As shown, the system also provides various prompts 40 to the coach-counselor that are related to the associated subset of combination data 82. In the example, prompts to the coach-counselor include: "Strongly recommend [to the user] pairing the CO sensor to mobile app to better track reduction"; "Suggest lesson [to the user]—'Using Your Breath Sensor'" [media content provided in the smoking-cessation program]; and "Suggest [to the user] talking to a coach about the benefits of the sensor and reduction." As noted above, the prompts 40 are a communication topic from a database of generic information applicable to the smoking cessation program. In some cases, the prompt is a combination of the generic information with specific patient information. Regardless, the prompts are custom created discussion topics based on the activities of the specific user. Such custom created discussion prompts improve efficiency and accuracy of an interaction between the coach-counselor and the individual-user to provides a coaching topic for the coach-counselor to assist the individual-user in the behavioral-modification program.

Figure 6:
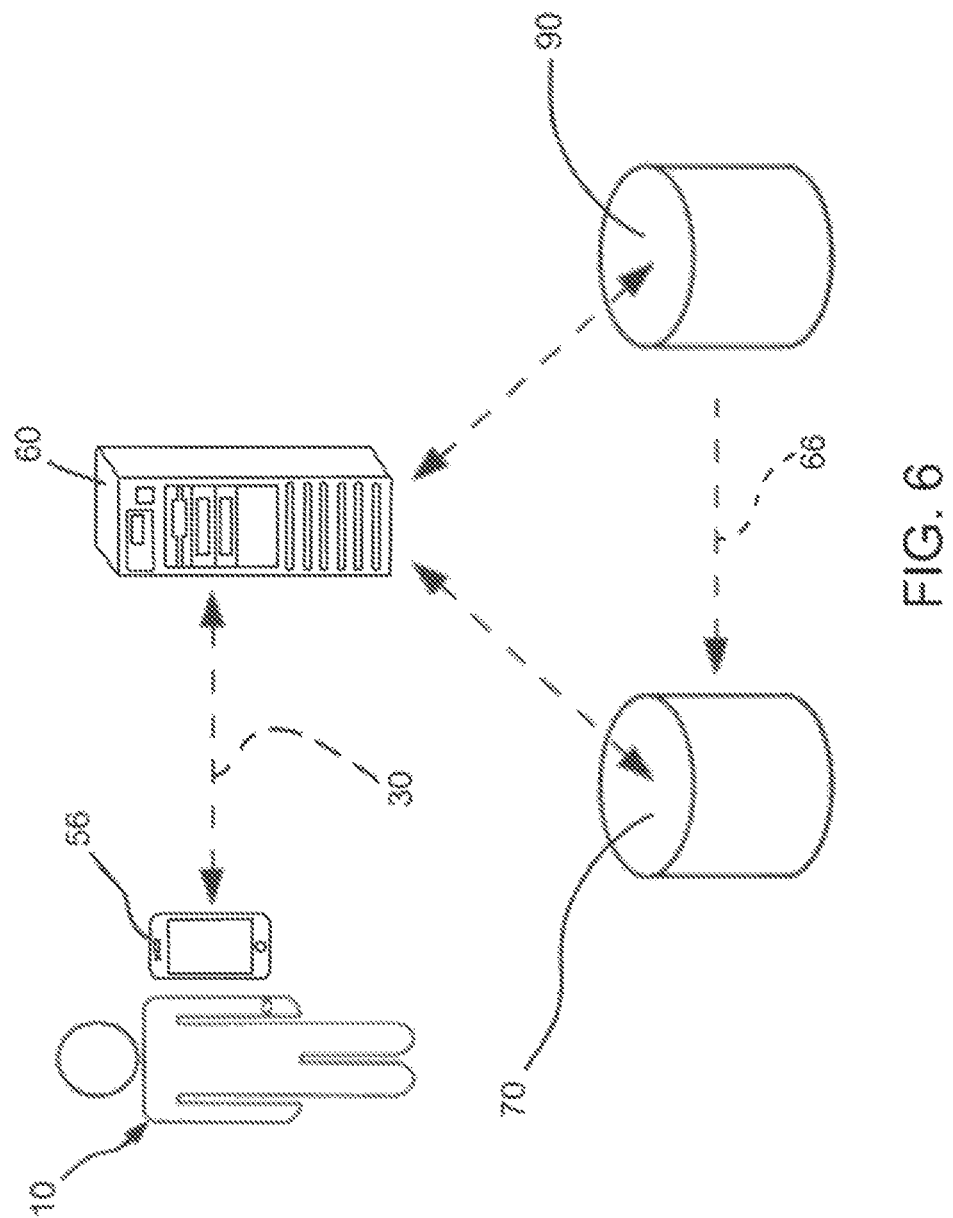
FIG. 6 is a conceptual illustration of an embodiment of a system/method for enhancing a direct electronic interaction between one or more systems/servers of a behavioral-modification program and an individual-user.

FIG. 6 is another conceptual illustration of an embodiment of a system/method for enhancing a direct electronic interaction 30 between one or more systems/servers 60 of a behavioral-modification program and an individual-user 10. In this variation, the system/server 60 can provide feedback or personalized recommendations to the user 10 with or without a coach-counselor. The direct interaction between the user 10 and the behavioral-modification program can provide real-time personalized advice to a user 10 while providing the user with a sense of progress, completion, and encouragement. The direct-interaction system described by FIG. 6 can incorporate additional information in place of or in addition to coaching from a coach-counselor. This additional information can be customized to the individual based on the individual's interaction with the program (e.g., see app data subset 78 discussed above in FIGS. 2A to 3C.) Additionally, the information can comprise generic information regarding the behavior-modification program. For purposes of clarity, the information provided to the individual through the direct electronic interaction 30 can be referred to as program-related content. As discussed herein, the program-related content can be personalized to an individual user's goals; feature availability of the program; the individual's prior history in and/or before participation in the program; and can be customized to include the user's personal information (e.g., the user's name, the coach's name, selected goals, etc.) Because the program-related content is provided via an electronic communication, the system can track the user's activity using the program-related content to determine whether the user's activity was started, is in progress as well as the extent of the progress, or completed without requiring the user to affirmatively report progress.

Program-related content can include any change to informational-content, including but not limited to, URL links, informational cards (e.g., electronic "cards" discussed below, lessons, videos, challenges, activities, media content, tasks. The program-related content can include content that is meant to be reviewed (passive content) or information that requires an activity or action by the user (action). For example, some program-related content can require a call-to-action, which includes a graphical element that prompts the user to perform some targeted action such as engaging in a challenge related to behavior modification, an activity related to the program (e.g., contacting a family member), or a request to obtain biological data (e.g., use the breath sensor).

In another variation of the system and method includes customizing/personalizing a card with data specific to the user. In such a case, the card is generic, but has electronic placeholders that are filled with user-specific data when sent to the user. For example, a card can generically include users of "Your top 3 reasons for the cigarettes you logged over the past 48 hours" or "Your highest/lowest CO readings over the last 48 hours." Each user then receives a customized card comprising the generic information with user-specific information incorporated into the generic message on the card.

As noted above, and as conveyed in FIG. 6, the system 60 can monitor the user's 10 activity through the electronic interaction 30. The system can then use algorithms to draw from information in one or more databases 90 that is generic to the program. The system then selects informational cards having content that applies to the user 10. As such, the informational cards can be directly conveyed to the user's electronic device 56, or the informational cards can be compiled/added 66 to one or more the user's personal database 70. In some variations, the informational cards will remain on the generic database 90 but the system uses user-specific information stored on their personal database 70 to pull the relevant generic information from the database 90.

FIGS. 7A and 7B illustrate an interface of an electronic device 56 to demonstrate an example of a user's direct interaction with the system/method of a smoking cessation behavioral-modification program. As shown, the interface 56 can include any number of data subsets discussed above, including but not limited to previously the subsets of data disclosed herein. For example, FIGS. 7A and 7B show submitted biologic data 76, application 78, as well as a prompt 40 discussed above. In the illustrated variation, biologic data 76 shows a measured exhaled CO reading (shown as "3") submitted from the user using a breath sensor. The application data shows an application entry of the number of cigarettes smoked over a period of time (shown as "8"). The display can include any relevant text as needed as well as a control panel 46 to interact with the system and/or coach.

FIGS. 7A and 7B also illustrate informational data cards 44, which are selected to provide personalized information specific to the user. In the illustrated example, FIG. 7A illustrates an information data card 44 specific to someone just entering the smoking cessation behavioral modification program (called "PIVOT"). As shown in FIG. 7B, once the user engages the informational card 40, which can simply provide information or require interaction from the user, the system marks the informational card 44 as completed. However, variations of the system allow for the individual to revisit any informational card 44 at a later point. As noted herein, informational data cards are one example of program-related content (as discussed above) that is electronically transmitted to the user 10

Figure 8:
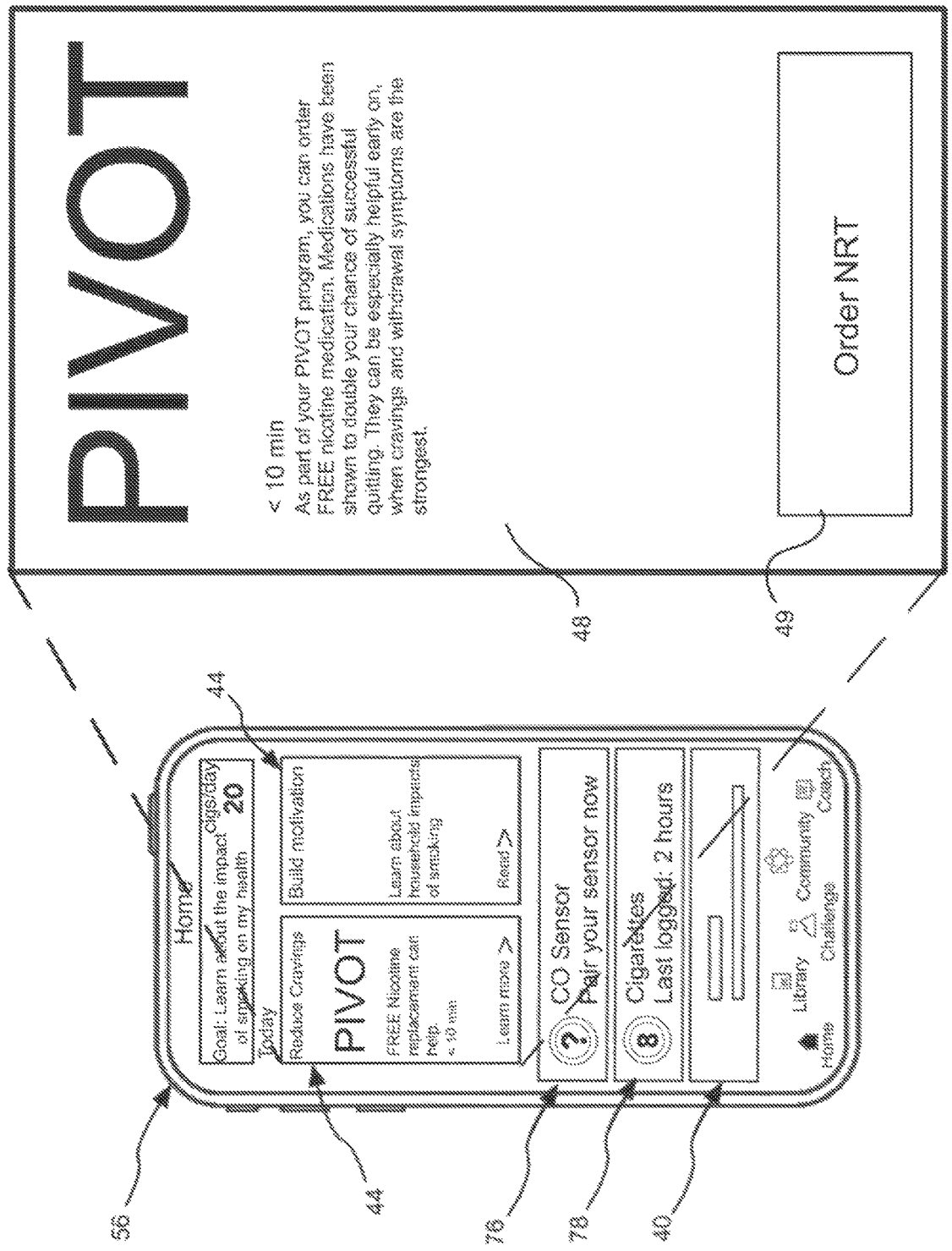
FIG. 8 illustrates an electronic interface having different informational cards 44 that display information selected and customized for the user based on any subset of data as discussed above.

FIG. 8 illustrates an electronic interface having different informational cards 44 that display information selected and customized for the user based on any subset of data as discussed above. FIG. 8 also illustrates that the informational cards 44 can include content 48 that is relevant to the behavioral modification program. As noted above, the content can be generic to the program but selected based on specific criteria regarding the user. Alternatively, or in combination, the content 48 can be customized for the user. In the example shown, the data card 48 provides media content to explain the benefit of ordering nicotine replacement medication along with facts regarding the medication. The content 48 further allows the user to interact with one or more buttons 49, which in the illustrated example allows the user to order the medication.

The systems and methods described herein also allow for supporting users in a very user-centric manner. For example, the systems and methods can allow for preserving the user's autonomy by monitoring and identifying any card that a user ignores or does not act on. To preserve the user's autonomy, the system and methods can delay for a specified period of time prompting the user with the same or similar card. Such a feature allows for an "automatic snooze" of information that the user viewed but did not act upon. The period for the delay of time can be selected by the user and/or selected by the system configuration.

In another variation, the systems and method can include a card "expiration" function where the system stops prompting the user with a card (and/or similar cards) if the user viewed it but did not act on it for a number of times. In one example, the system stops prompting the user with a card after 3 impressions (where the system sees the user as receiving the card but failing to act on it 3 times).

The systems and method can further include a card chaining function where the system prompts card "A" any specified number of times and then expires card "A" in favor of card "B", where card "A" and "B" can have related information or mutually exclusive information. The system can prompt card "B" any specified number of times and then expire card "B" in favor of card "A" or another card "C". This sequence can be repeated such that the chaining of cards can be as long or as short as desired. Such an approach maintains the coaching/counseling novel as opposed to simply repeating the same information.

Variations of the system and methods described herein can select content based on user-specific information. In such a case, the counselor-coaching prompts and/or the cards can be tailored to that information. For example, some users may desire to quit on a specific day while other users desire a normal quit plan (i.e., quitting over a longer duration of time). In such a case, the system/method can assign users to either a "fast quit" plan or a "normal quit" plan. As an example, those users that are identified as "fast quit" users will receive coach-counseled prompts and/or cards of a highly prioritized list of essential steps in the behavior-modification program. In contrast, those users identified as "normal quit" users will get customized content that allows for a longer time in the plan sequence.

Additional examples of customized feedback include prompting the user in layers. For example, the information prompted in the current week takes priority, if the user completes the interaction with cards/coaching for that week, then the previous week's information that was incomplete can be prompted by the coach/system. Cards/coaching can also prompt the user to keep goals and usage current. For example, the present system prompts the user (via coaching and/or cards) for a weekly update of cigarettes-per-day to ensure the user's goal is current at least every 2 weeks. In those cases where a user is very engaged/successful in the program, the system can provide customized program-related content (e.g., coaching and or other information) that recommend setting aggressive behavioral goals. For example, if a user reduces smoking by 50%, the system can then prompt the user to go ahead and quit. In another variation, a user that completes all lessons and is still active might be prompted by the system if they want to make a change, such as reducing how much they smoke or quitting entirely.

Figure 9:
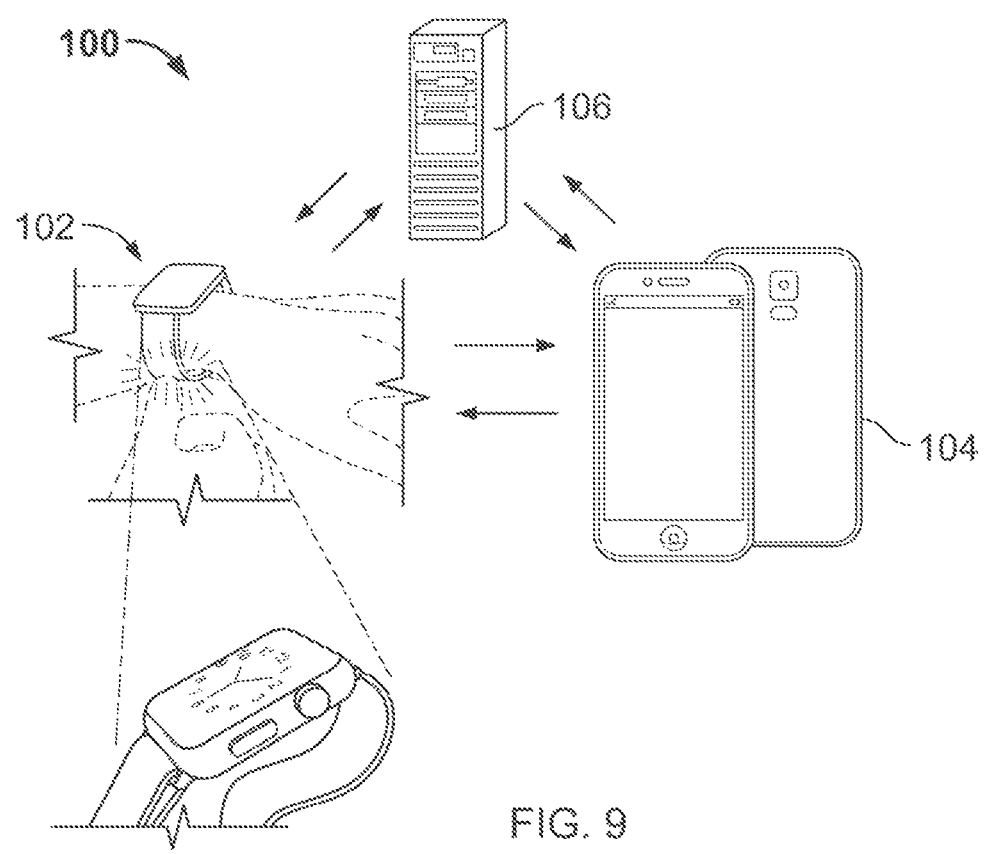
FIG. 9 depicts an illustrative system including a wearable device, a mobile device, and a remote server in communication with the wearable device and the mobile device in accordance with some embodiments of the disclosure.

In some embodiments, the systems and methods described herein provide for a system comprising one or more mobile devices and a server in communication with the mobile devices. FIG. 9 shows an exemplary embodiment 100 for such a system including device 102, device 104, and server 106 in communication with devices 102 and 104. Device 102 assists in detecting a patient's smoking behavior. Device 102 includes a processor, a memory, and a communications link for sending and receiving data from device 104 and/or server 106. Device 102 includes one or more sensors to measure the patient's smoking behavior based on measuring one or more of the patient's CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. For example, device 102 may include PPG-based sensors for measuring CO, eCO, SpCO and SpO2, electrocardiography-based sensors for measuring heart rate and blood pressure, acoustic signal processing-based sensors for measuring respiratory rate, wearable temperature sensors for measuring body temperature, electrodermal activity-based sensors for measuring skin conductance, electroencephalogram, implantable sensors placed in the skin, fat or muscle that measure CO and other variables, intra-oral CO sensors, ambient CO sensors, and other suitable sensors. These sensors may have a variety of locations on or in the body for optimal monitoring.

Device 102 may be carryable or wearable. For example, device 102 may be wearable in a manner similar to a wristwatch. In another example, device 102 may be carryable or wearable and attached to the fingertip, ear lobe, ear pinna, toe, chest, ankle, arm, a fold of skin, or another suitable body part. Device 102 may attach to the suitable body part via clips, bands, straps, adhesively applied sensor pads, or another suitable medium. For example, device 102 may be attached to a fingertip via a finger clip. In another example, device 102 may be attached to the ear lobe or ear pinna via an ear clip. In yet another example, device 102 may be attached to the toe via a toe clip. In yet another example, device 102 may be attached to the chest via a chest strap. In yet another example, device 102 may be attached to the ankle via an ankle band. In yet another example, device 102 may be attached to the arm via bicep or tricep straps. In yet another example, device 102 may be attached to a fold of skin via sensor pads.

Device 102 may prompt the patient for a sample or the device, if worn, may take a sample without needing patient volition. The sampling may be sporadic, continuous, near continuous, periodic, or based on any other suitable interval. In some embodiments, the sampling is continuously performed as often as the sensor is capable of making the measurement. In some embodiments, the sampling is performed continuously after a set time interval, such as five or fifteen minutes or another suitable time interval.

In some embodiments, device 102 includes one or more sensors to monitor SpCO using a transcutaneous method such as PPG. The transcutaneous monitoring may employ transmissive or reflectance methods. Device 104 may be a smart phone or another suitable mobile device. Device 104 includes a processor, a memory, and a communications link for sending and receiving data from device 102 and/or server 106. Device 104 may receive data from device 102. Device 104 may include an accelerometer, a global positioning system-based sensor, a gyroscopic sensor, and other suitable sensors for tracking the described parameters. Device 104 may measure certain parameters, including but not limited to, movement, location, time of day, patient entered data, and other suitable parameters The patient entered data received by device 104 may include stressors, life events, geographic location, daily events, administrations of nicotine patches or other formulas, administrations of other drugs for smoking cessation, and other suitable patient entered data. For example, some of the patient entered data may include information regarding phone calls, athletics, work, sport, stress, sex, drinking, smoking, and other suitable patient entered data. Patient use of their smart phone for texting, calling, surfing, playing games, and other suitable use may also be correlated with smoking behavior, and these correlations leveraged for predicting behavior and changing behavior. Device 104 or server 106 (subsequent to receiving the data) may compile the data, analyze the data for trends, and correlate the data either real time or after a specified period of time is complete. Server 106 includes a processor, a memory, and a communications link for sending and receiving data from device 102 and/or device 104. Server 106 may be located remote to devices 102 and 104 at, e.g., a healthcare provider site, or another suitable location.

Figure 10:
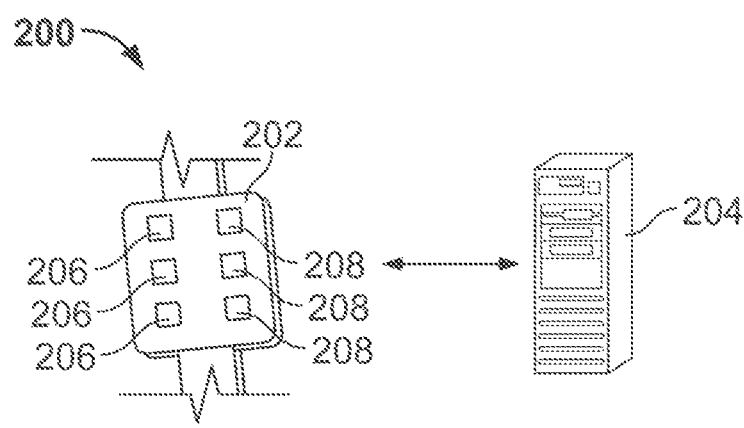
FIG. 10 depicts another illustrative system including a wearable device and a remote server in communication with the wearable device in accordance with some embodiments of the disclosure.

FIG. 10 shows an exemplary embodiment 200 for a system including device 202 and server 204 in communication with device 202. Device 202 assists in detecting a patient's smoking behavior. Device 202 includes a processor, a memory, and a communications link for sending and receiving data from server 204. Device 202 may be carryable or wearable. For example, device 202 may be wearable in a manner similar to a wristwatch. Device 202 includes one or more sensors 206 to measure the patient's smoking behavior based on measuring one or more of the patient's CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters.

Device 202 may include one or more sensors 208 to measure certain parameters, including but not limited to, movement, location, time of day, patient entered data, and other suitable parameters. The patient entered data may include stressors, life events, location, daily events, administrations of nicotine patches or other formulas, administrations of other drugs for smoking cessation, and other suitable patient entered data. The patient entered data may be received in response to a prompt to the patient on, e.g., a mobile device such as device 104, or entered without prompting on the patient's volition. For example, some of the patient entered data may include information regarding phone calls, athletics, work, sport, stress, sex, drinking, smoking, and other suitable patient entered data. Device 202 or server 204 (subsequent to receiving the data) may compile the data, analyze the data for trends, and correlate the data either real time or after a specified period of time is complete. Server 204 includes a processor, a memory, and a communications link for sending and receiving data from device 202. Server 204 may be located remote to device 202 at, e.g., a healthcare provider site, or another suitable location.

In some embodiments, device 102 or 202 includes a detector unit and a communications unit. Device 102 or 202 may include a user interface as appropriate for its specific functions. The user interface may receive input via a touch screen, keyboard, or another suitable input mechanism. The detector unit includes at least one test element that is capable of detecting a substance using an input of a biological parameter from the patient that is indicative of smoking behavior. The detector unit analyzes the biological input from the patient, such as expired gas from the lungs, saliva, or wavelengths of light directed through or reflected by tissue. In some embodiments, the detector unit monitors patient SpCO using PPG. The detector unit may optionally measure a number of other variables including, but not limited to, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. For breath-based sensors, patient input may include blowing into a tube as part of the detector unit. For saliva or other body fluid-based sensors, patient input may include placement of a fluid sample in a test chamber provided in the detector unit.

For light-based sensors such as PPG, patient input may include placement of an emitter-detector on a finger or other area of exposed skin. The detector unit logs the date and time of day, quantifies the presence of the targeted substance, and stores the data for future analysis and/or sends the data to another location for analysis, e.g., device 104 or server 106. The communications unit includes appropriate circuitry for establishing a communications link with another device, e.g., device 104, via a wired or wireless connection. The wireless connection may be established using WI-FI, BLUETOOTH, radio frequency, or another suitable protocol.

Figure 11:
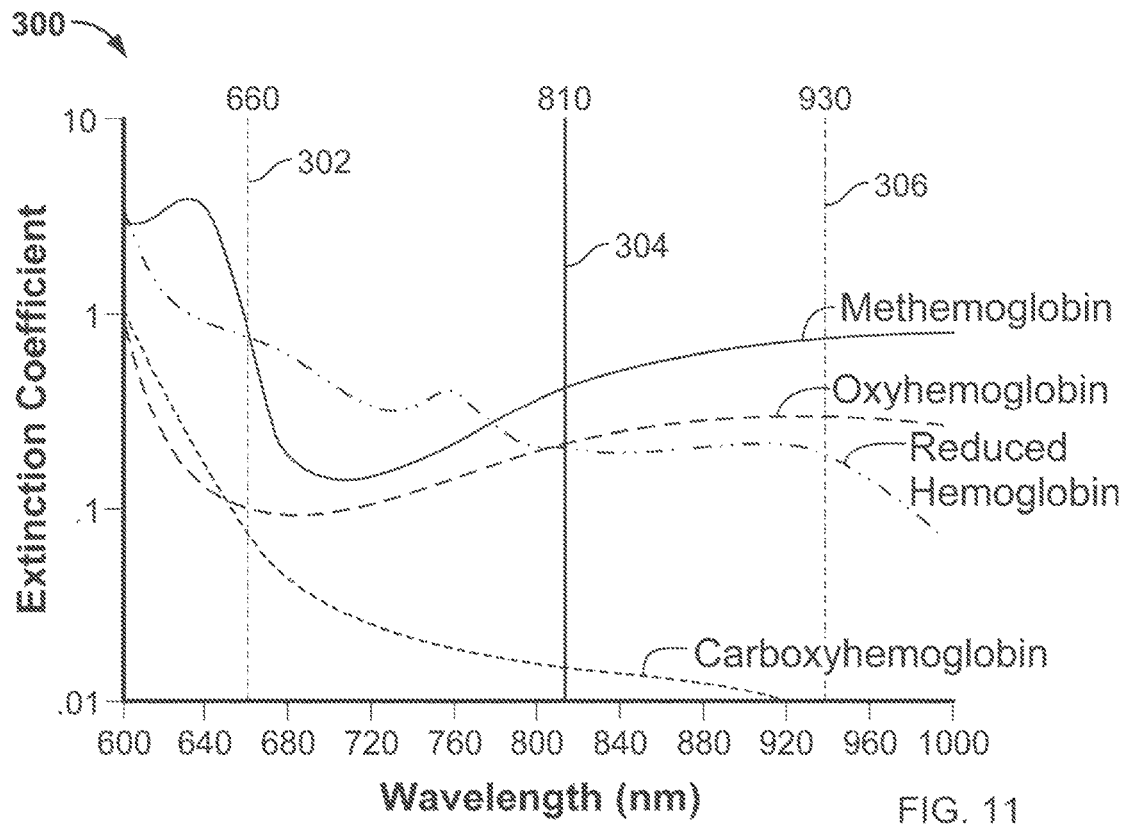
FIG. 11 depicts illustrative light absorption curves for various types of hemoglobin, allowing for measurement of the levels of carboxyhemoglobin (SpCO) and oxyhemoglobin (SpO2) using a photoplethysmography (PPG) sensor in accordance with some embodiments of the disclosure.

FIG. 11 depicts an illustrative embodiment 300 of suitable wavelengths for analyzing SpO2 and SpCO using a light-based sensor. SpCO for a patient may be measured by intermittently testing the patient's exhaled breath with a suitable sensor. In another example, SpCO for the patient may be measured using a transcutaneous method such as photoplethysmography (PPG). SpCO is detected by passing light through patient tissue, e.g., ear lobe, ear pinna, fingertip, toe, a fold of skin, or another suitable body part, and analyzing attenuation of various wavelengths. SpO2 is typically measured using two wavelengths, e.g., 302 (660 nm) and 306 (940 nm). SpCO may be measured using three wavelengths, e.g., 302 (660 nm), 304 (810 nm), and 306 (940 nm), or up to seven or more wavelengths, e.g., ranging from 500-1000 nm. Such a PPG sensor may be implemented via finger clips, bands, adhesively applied sensor pads, or another suitable medium. The PPG sensor may be transmissive, such as used in many pulse oximeters. In transmissive PPG sensors, two or more waveforms of light are transmitted through patient tissue, e.g., a finger, and a sensor/receiver on the other side of the target analyzes the received waveforms to determine SpCO. Alternatively, the PPG sensor may be reflective. In reflectance PPG sensors, light is shined against the target, e.g., a finger, and the receiver/sensor picks up reflected light to determine the measurement of SpCO. More details are provided below.

Transcutaneous or transmucosal sensors are capable of non-invasively determining blood CO level and other parameters based on analysis of the attenuation of light signals passing through tissue. Transmissive sensors are typically put against a thin body part, such as the ear lobe, ear pinna, fingertip, toe, a fold of skin, or another suitable body part. Light is shined from one side of the tissue and detected on the other side. The light diodes on one side are tuned to a specific set of wavelengths. The receiver or detector on the other side detects which waveforms are transmitted and how much they are attenuated. This information is used to determine the percentage binding of O2 and/or CO to hemoglobin molecules, i.e., SpO2 and/or SpCO.

Reflectance sensors may be used on a thicker body part, such as the wrist. The light that is shined at the surface is not measured at the other side but instead at the same side in the form of light reflected from the surface. The wavelengths and attenuation of the reflected light is used to determine SpO2 and/or SpCO. In some embodiments, issues due to motion of the patient wrist are corrected using an accelerometer. For example, the information from the accelerometer is used to correct errors in the SpO2 and SpCO values due to motion. Examples of such sensors are disclosed in U.S. Pat. No. 8,224,411, entitled "Noninvasive Multi-Parameter Patient Monitor." Another example of a suitable sensor is disclosed in U.S. Pat. No. 8,311,601, entitled "Reflectance and/or Transmissive Pulse Oximeter". These two U.S. patents are incorporated by reference herein in their entireties, including all materials incorporated by reference therein.

In some embodiments, device 102 or 202 is configured to recognize a unique characteristic of the patient, such as a fingerprint, retinal scan, voice label or other biometric identifier, in order to prevent having a surrogate respond to the signaling and test prompts to defeat the system. For this purpose, a patient identification sub-unit may be included in device 102 or 202. Persons of ordinary skill in the art may configure the identification sub-unit as needed to include one or more of a fingerprint scanner, retinal scanner, voice analyzer, or face recognition as are known in the art. Examples of suitable identification sub-units are disclosed, for example in U.S. Pat. No. 7,716,383, entitled "Flash-interfaced Fingerprint Sensor," and U.S. Patent Application Publication No. 2007/0005988, entitled "Multimodal Authentication," each of which is incorporated by reference herein in their entirety.

The identification sub-unit may include a built in still or video camera for recording a picture or video of the patient automatically as the biological input is provided to the test element. Regardless of the type of identification protocol used, device 102 or 202 may associate the identification with the specific biological input, for example by time reference, and may store that information along with other information regarding that specific biological input for later analysis.

A patient may also attempt to defeat the detector by blowing into the detector with a pump, bladder, billows, or other device, for example, when testing exhaled breath. In the embodiment of saliva testing, a patient may attempt to substitute a clean liquid such as water. For light-based sensors, the patient may ask a friend to stand in for him or her. Means to defeat these attempts may be incorporated into the system. For example, device 102 or 202 may incorporate the capability of discerning between real and simulated breath delivery. This functionality may be incorporated by configuring the detector unit to sense oxygen and carbon dioxide, as well as the target substance (e.g., carbon monoxide). In this manner, the detector unit can confirm that the gas being analyzed is coming from expired breath having lower oxygen and higher carbon dioxide than ambient air. In another example, the detector unit may be configured to detect enzymes naturally occurring in saliva so as to distinguish between saliva and other liquids. In yet another example, light-based sensors may be used to measure blood chemistry parameters other than CO level and thus results may be compared to known samples representing the patient's blood chemistry.

In some embodiments, device 104 (e.g., a smart phone) receives measurements from device 102 (e.g., a wearable device) in real time, near real time, or periodically according to a suitable interval. Device 104 may provide a user interface for prompting a patient for certain inputs. Device 104 may provide a user interface for displaying certain outputs of the collected data. Device 104 may permit the patient to input information that the patient believes relevant to his or her condition without prompting or in response to prompting. Such information may include information about the patient's state of mind such as feeling stressed or anxious. Such unprompted information may be correlated to a biological input based on a predetermined algorithm, such as being associated with the biological input that is closest in time to the unprompted input or associated with the first biological input occurring after the unprompted input. Server 106 (e.g., a healthcare database server) may receive such data from one or both of devices 102 and 104. In some embodiments, the data may be stored on a combination of one or more of devices 102, 104, and 106. The data may be reported to various stakeholders, such as the patient, patient's doctor, peer groups, family, counselors, employer, and other suitable stakeholders.

Figure 15:
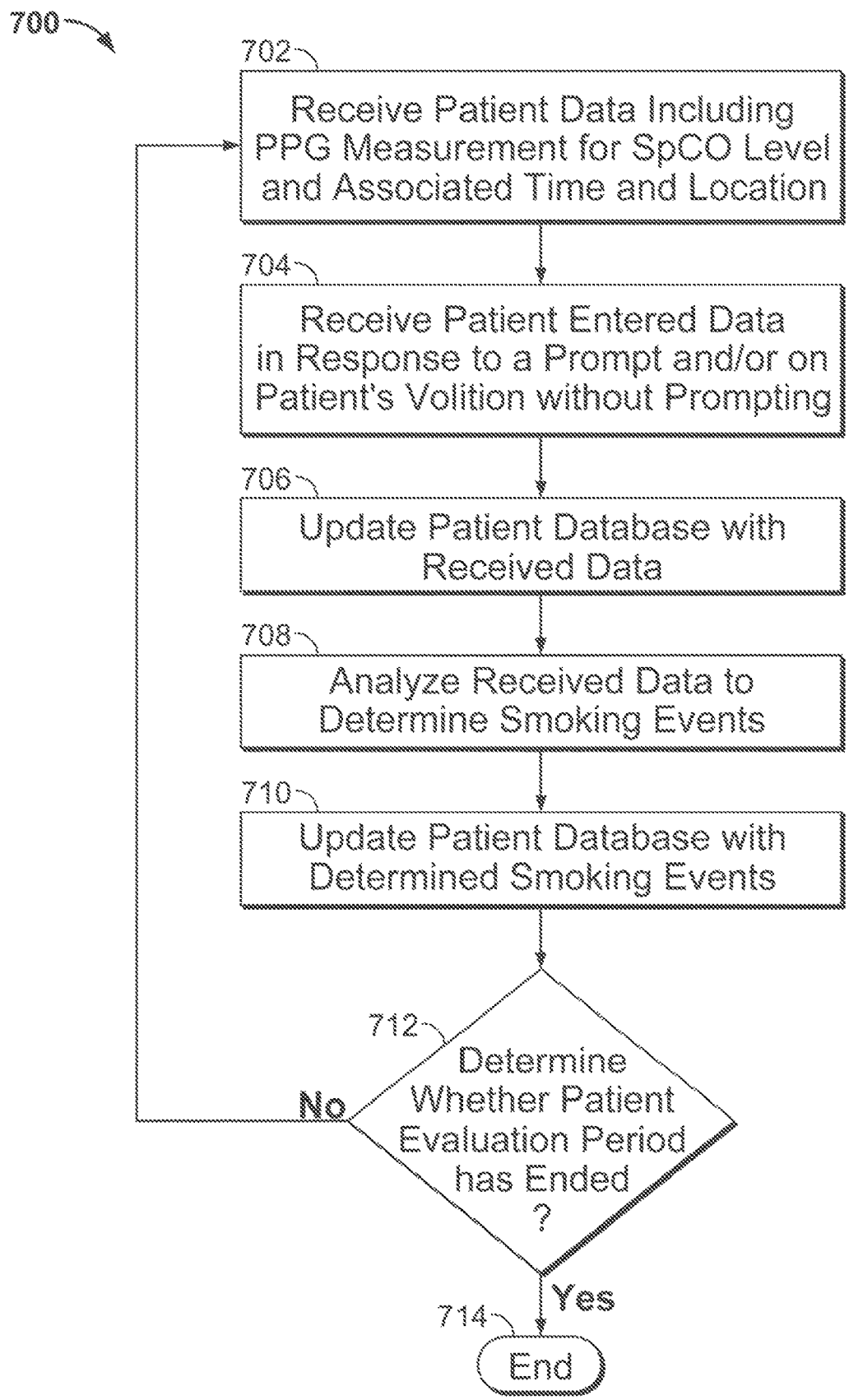
FIG. 15 depicts an illustrative flow diagram for detecting smoking behavior of a patient in accordance with some embodiments of the disclosure.

In some embodiments, a wearable device, e.g., device 102 or 202, may be applied to patients during, e.g., their usual annual visits, to detect smoking behavior and then refer the smokers to quit programs. The patient is provided with a wearable device to wear as an outpatient for a period of time, e.g., one day, one week, or another suitable period of time. Longer wear times may provide more sensitivity in detection of smoking behavior and more accuracy in quantifying the variables related to smoking behavior. FIG. 15 below provides an illustrative flow diagram for detecting smoking behavior and will be described in more detail below.

In some embodiments, employers ask employees to voluntarily wear the wearable device for a period of time, such as one day, one week, or another suitable period of time. The incentive program may be similar to programs for biometric screening for obesity, hyperlipidemia, diabetes, hypertension, and other suitable health conditions. In some embodiments, health care insurance companies ask their subscribers to wear the wearable device for a suitable period of time to detect smoking behavior. Based on the smoking behavior being quantified, these patients may be referred to a smoking cessation program as described in the present disclosure.

Figure 12:
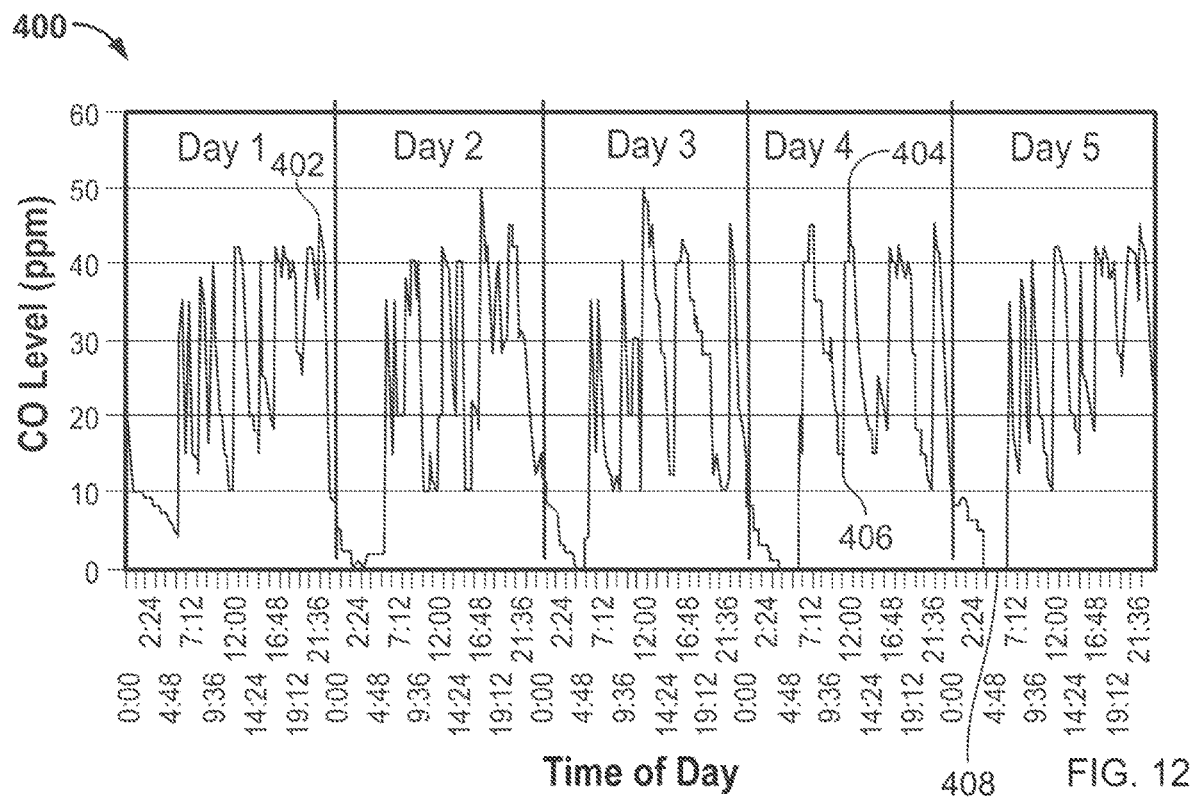
FIG. 12 depicts a chart for a patient's varying levels of SpCO for a typical five-day monitoring period prior to commencing a smoking cessation program in accordance with some embodiments of the disclosure.

When wearing the wearable device for a suitable period of time, e.g., five days, a number of parameters may be measured real-time or near real time. These parameters may include, but are not limited to, CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. FIG. 12 shows illustrative chart 400 for a patient's varying levels of SpCO for a typical five-day monitoring period. Data points 402 and 404 indicate high level of CO which in turn likely indicates high smoking events. Data points 406 and 408 indicate low level of CO likely because the patient was asleep or otherwise occupied. One or more algorithms may be applied to the granular data points on the curve to detect a smoking event with adequate sensitivity and specificity. For example, the algorithms may analyze one or more of shape of the SpCO curve, start point, upstroke, slope, peak, delta, downslope, upslope, time of change, area under curve, and other suitable factors, to detect the smoking event.

Data from the wearable device may be sent to a smart phone, e.g., device 104, or a cloud server, e.g., server 106 or 204, either in real time, at the end of each day, or according to another suitable time interval. The smart phone may measure parameters, including but not limited to, movement, location, time of day, patient entered data, and other suitable parameters. The patient entered data may include stressors, life events, location, daily events, administrations of nicotine patches or other formulas, administrations of other drugs for smoking cessation, and other suitable patient entered data. For example, some of the patient entered data may include information regarding phone calls, athletics, work, sport, stress, sex, drinking, smoking, and other suitable patient entered data. The received data may be compiled, analyzed for trends, and correlated either real time or after the period of time is complete.

Figures 13, 14:
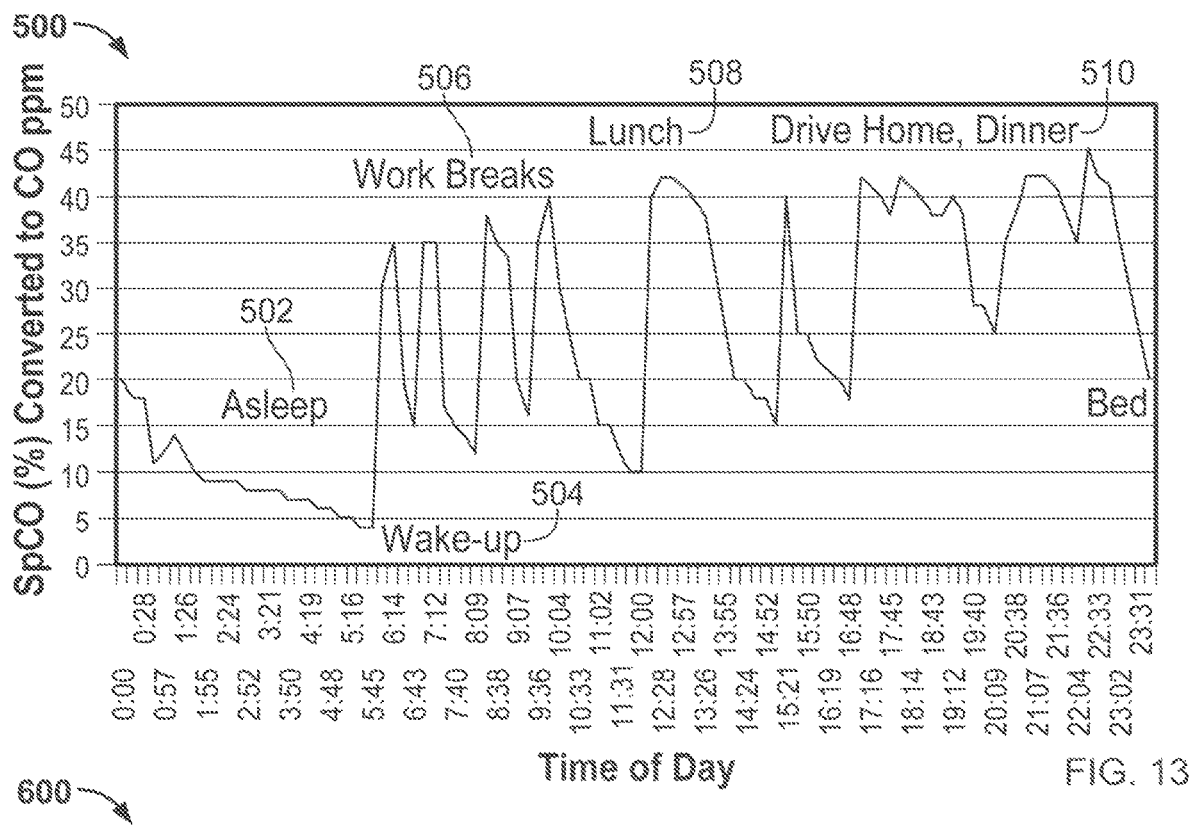
FIG. 13 depicts a trend of SpCO levels and smoking triggers for a patient over a typical day prior to commencing a smoking cessation program in accordance with some embodiments of the disclosure.
FIG. 14 depicts a data structure for storing SpCO levels and smoking triggers for a patient over a typical day in accordance with some embodiments of the disclosure.

From the parameters measured above, information regarding smoking may be derived via a processor located in, e.g., device 102, 104, or 202, or server 106 or 204. For example, the processor may analyze the information to determine CO trends, averages, peaks, and associations, other vital sign trends during day, and how do those vitals change before, during and after smoking. FIG. 13 shows an illustrative diagram 500 for the analyzed information. The patient may arrive at FIG. 13 by zooming in on a given day in FIG. 12. Data point 502 indicates the SpCO level when the patient is asleep. Data point 504 shows that when the patient wakes up, the SpCO level is the lowest. Data points 506, 508, and 510 indicate high SpCO levels are associated with triggers such as work breaks, lunch, and commute. The processor may analyze the SpCO trends in FIG. 13 to determine parameters such as total number of cigarettes smoked, average number of cigarettes smoked per day, maximum number of cigarettes smoked per day, intensity of each cigarette smoked, quantity of each cigarette smoked, what that patient's smoking event looks like on the curve to be used later for quit program, time of day, day of week, associated stressors, geography, location, and movement. For example, the total number of peaks in a given day may indicate the number of cigarettes smoked, while the gradient of each peak may indicate the intensity of each cigarette smoked.

FIG. 14 depicts an illustrative data structure for storing patient data. In this embodiment, data structure 600 illustrates patient data 602 associated with data points in FIG. 13, e.g., data point 508. Patient data 602 includes identifying information for the patient such as patient name 604 and patient age 606. Patient data 602 includes curve data 608 corresponding to the curve in FIG. 13. For example, curve data 608 includes curve identifier 610 corresponding to data point 508. The data corresponding to data point 508 may be collected by device 102, 104, or 202, and/or server 106 or 204 or a combination thereof. Data associated with curve identifier 610 includes day, time, and location information 612. The data includes patient vital signs such as CO and O2 levels 614. The data includes patient entered data such as trigger 616. The patient entered data may be entered in response to a prompt to the patient on, e.g., device 104, or entered without prompting on the patient's volition. Curve data 608 includes curve identifier 618 for additional data points in FIG. 13. Data structure 600 may be adapted as appropriate for storing patient data.

FIG. 15 depicts an illustrative flow diagram 700 for detecting smoking behavior of a patient over a suitable evaluation period. When the patient wears the wearable device for a suitable period of time, e.g., five days, a number of parameters may be measured in real-time, near real time, at the end of each day, or according to another suitable time interval. These parameters may include, but are not limited to, CO, eCO, SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. The wearable device or another suitable device may measure parameters, including but not limited to, movement, location, time of day, and other suitable parameters.

At step 702, a processor in a smart phone, e.g., device 104, or a cloud server, e.g., server 106 or 204, receives the described patient data. At step 704, the processor receives patient entered data in response to a prompt displayed to the patient on, e.g., a smart phone, and/or patient data entered without a prompt on the patient's volition. The patient entered data may include stressors, life events, location, daily events, administrations of nicotine patches or other formulas, administrations of other drugs for smoking cessation, and other suitable patient entered data. At step 706, the processor sends instructions to update a patient database with the received data. For example, the processor may transmit the patient data to a healthcare provider server or a cloud server that hosts the patient database.

At step 708, the processor analyzes the patient data to determine smoking events. The processor may compile the data, analyze the data for trends, and correlate the data either real time or after the evaluation period is complete. For example, the processor may analyze the information to determine CO trends, averages, peaks, shape of curve, and associations, other vital sign trends during day, and how those vitals change before during and after smoking. The processor may analyze the SpCO trends to determine parameters such as total number of cigarettes smoked, average number of cigarettes smoked per day, maximum number of cigarettes smoked per day, intensity of each cigarette smoked, time of day, day of week, associated stressors, geography, location, and movement. For example, the total number of peaks in a given day may indicate the number of cigarettes smoked, while the gradient of each peak may indicate the intensity of each cigarette smoked.

At step 710, the processor transmits the determined smoking events and related analysis to the patient database for storage. At step 712, the processor determines whether the evaluation period has ended. For example, the evaluation period may be five days or another suitable time period. If the evaluation period has not ended, the processor returns to step 702 to receive additional patient data, analyze the data, and update the patient database accordingly.

If the evaluation period has ended, at step 714, the processor ends the data collection and analysis. For example, the processor may evaluate all collected data at the end of the evaluation period to prepare a report as described with respect to FIG. 16 below.

It is contemplated that the steps or descriptions of FIG. 15 may be used with any other embodiment of this disclosure. In addition, the steps and descriptions described in relation to FIG. 15 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 9 (e.g., device 102, 104, or 106) or FIG. 10 (e.g., device 202 or 204) could be used to perform one or more of the steps in FIG. 15.

Figure 16:
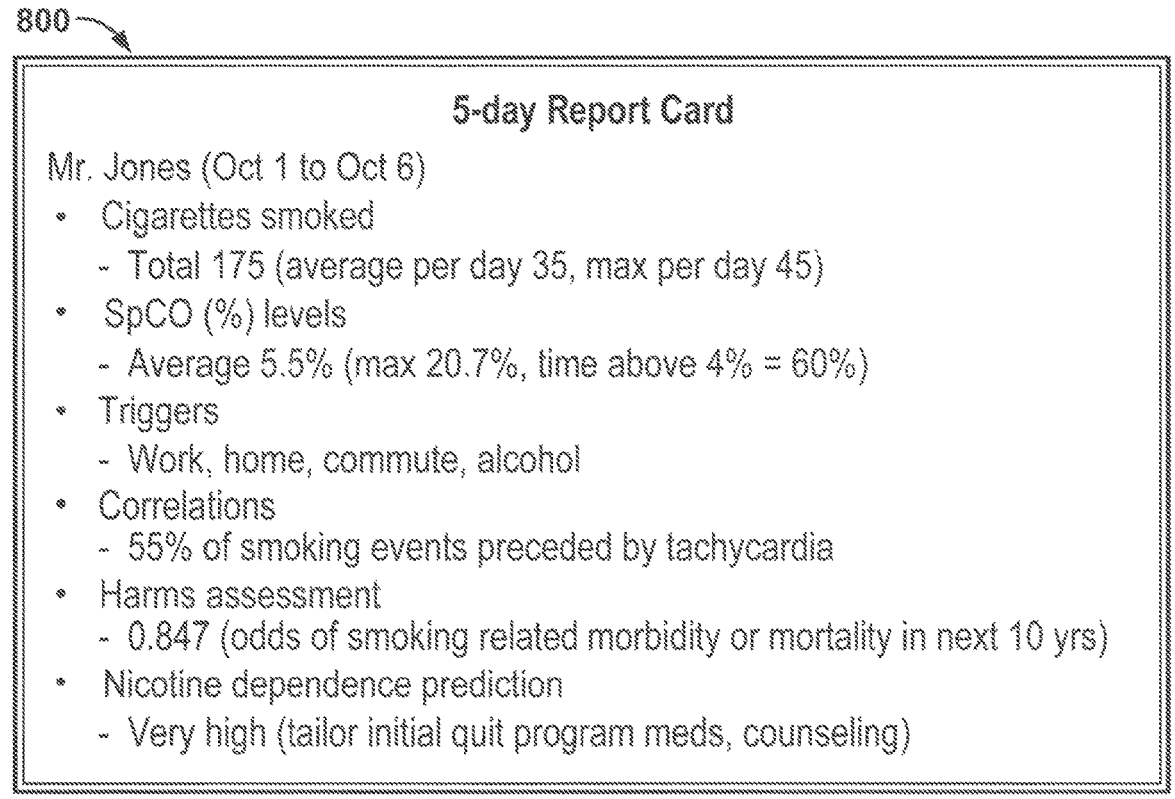
FIG. 16 depicts a sample report after a five-day evaluation for a patient in accordance with some embodiments of the disclosure.

In some embodiments, the systems and methods described herein provide for initiating and setting up a quit program for a patient. After the patient has completed a five-day evaluation while wearing the wearable device, e.g., device 102 or 202, the full dataset is compiled and analyzed by the system and delivered to the patient or a doctor for the quit program. FIG. 16 shows an illustrative embodiment 800 of a sample report from the analysis. For example, the report indicates that, from October 1 to October 6, Mr. Jones smoked a total of 175 cigarettes with an average number of 35 cigarettes smoked per day, and a maximum number of 45 cigarettes smoked in one day. Mr. Jones' CO level averaged at 5.5% with a maximum of 20.7% and stayed above 4% for 60% of duration of the five-day evaluation period. Mr. Jones' triggers included work, home stressors, and commute. The report recommends a high dose and frequency nicotine level prediction for commencing nicotine replacement therapy in view of Mr. Jones' smoking habits.

In some embodiments, the patient works with their doctor or counselor to begin the process to enter the quit program. In some embodiments, the system sets up a quit program automatically based on the data from the evaluation period. The sample report in FIG. 16 is one example of measuring SpCO and producing a report on CO exposure, associated stressors, and predicting a starting nicotine dose requirement. For example, a high volume and intensity smoker may be more nicotine dependent at quit program entry, which the processor can estimate based on five-day behavior, and the quit program would start the patient on a higher nicotine replacement therapy dose. This may avoid many patients failing early in a quit program due to withdrawal symptoms. Based on the report data, including average and maximum number of cigarettes smoked, SpCO levels, triggers, the processor may determine the dosage for nicotine for administration to the patient. For example, the processor may determine a high dosage of nicotine for patients that on average smoke more than a threshold number of cigarettes per day. As the report data is updated, the processor may update the dosage for nicotine as well.

The collected data may impact the quit program initiation and set-up for the patient immediately before they enter the program by assisting in drug selection and dosing. For example, indication of higher smoking may prompt starting on higher nicotine replacement therapy dose or multiple drugs (e.g., adding medication used to treat nicotine addiction, such as varenicline). The collected data may impact the quit program initiation and set-up by determining frequency, type, and duration of counseling required for the patient. The data may lead to stratification of smoker needs. For example, highest risk smokers with highest use may get more interventions while lower risk smokers may get fewer interventions. For example, interventions may include a text message, a phone call, a social networking message, or another suitable event, from the patient's spouse, friend, doctor, or another suitable stakeholder, at certain times of days when the patient is likely to smoke.

Figure 22:
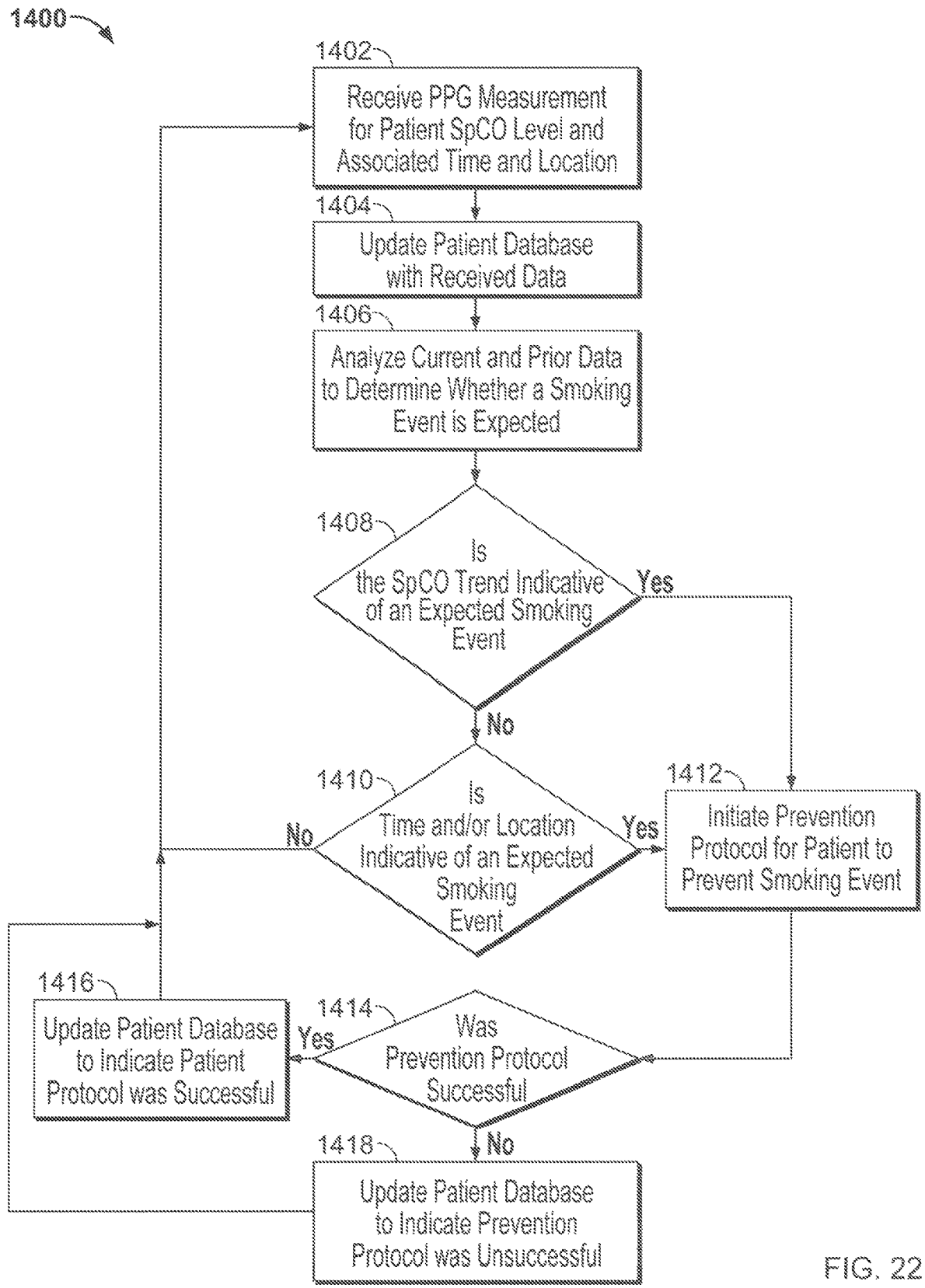
FIG. 22 depicts an illustrative flow diagram for predicting and preventing an expected smoking event in accordance with some embodiments of the disclosure.
Figure 23:
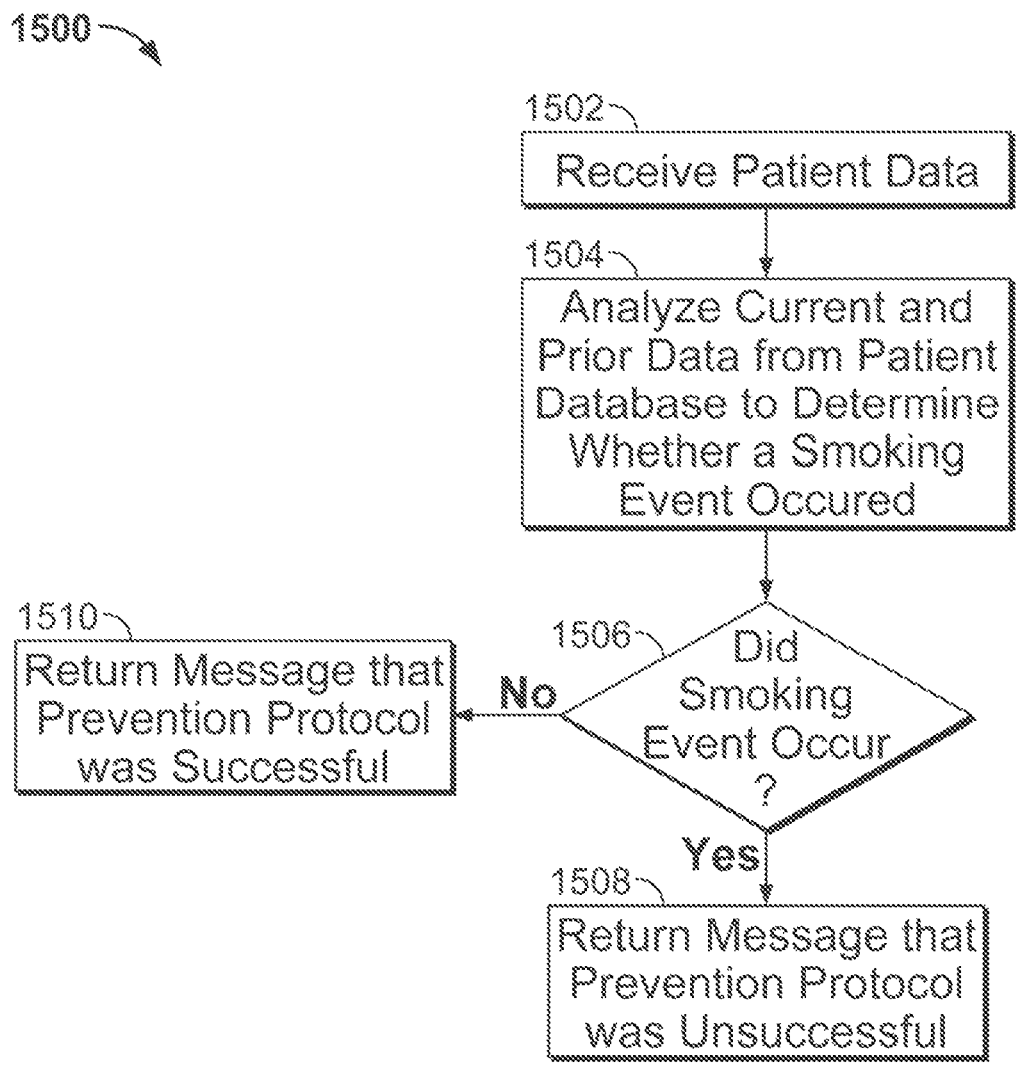
FIG. 23 depicts an illustrative flow diagram for step 1414 in FIG. 22 for determining whether a prevention protocol was successful in accordance with some embodiments of the disclosure.

The collected data may impact the quit program initiation and set-up by correlating smoking behavior with all variables above such as stressors prompting smoking, time of day, and other suitable variables used for counseling the patient up front to be aware of these triggers. Counseling interventions may target these stressors and there may be interventions aimed at those times of day for the patient, such as a text message or call at those times of days. The collected data may impact the quit program initiation and set-up by assigning peer groups based on smoking behavior. The collected data may be used to predict and/or avert a smoking event. For example, if tachycardia or heart rate variability or a suitable set of variables precedes most smoking events, this will sound an alarm and the patient may administer a dose of drug or can receive a call from a peer group, doctor, or counselor. FIG. 20 shows an illustrative embodiment of preempting a smoking event and will be discussed in more detail below. FIGS. 22 and 23 show illustrative flow diagrams for predicting and preventing an expected smoking event and will be discussed in more detail below.

In some embodiments, the systems and methods described herein provide for maintaining participation in the quit program for the patient. Once in the quit program, the patient may continue to wear the wearable device, e.g., device 102 or 202, for monitoring. The system may employ analytic tools such as setting an SpCO baseline and tracking progress against this baseline. The trend may drop to zero and stay there (indicating no more smoking). The trend may drop slowly with peaks and valleys (indicating reduction in smoking). The trend may drop to zero then spike for a recurrence (indicating a relapse).

The system may employ patient engagement strategies by providing small infrequent rewards for group or individual progress to engage the patient. The system may provide employer rewards, payers, spouse, or peer groups to engage the patient. The system may present the process for the patient as a game and improve visibility of progress. FIG. 21 provides an illustrative embodiment of such a user interface and will be discussed in more detail below. In some embodiments, the system may transmit the data in real time to a health care provider for remote monitoring and allowing the provider to efficiently monitor and adjust patient care without having to have them in the office every day. For example, the provider may send instructions to the system to adjust medication type and dose, alter intensity of counseling, call and text for positively encouraging progress, or trigger an intervention if the patient is failing to refrain from smoking. This may supplant staffed quit phone lines which are expensive and may efficiently automate the process. The system may employ increased intensity and frequency to improve outcomes in patients. The system may encourage the patient via support from spouse, employer, health care provider, peers, friends, and other suitable parties via scheduled phone calls, text messages, or other suitable communications.

Figure 17:
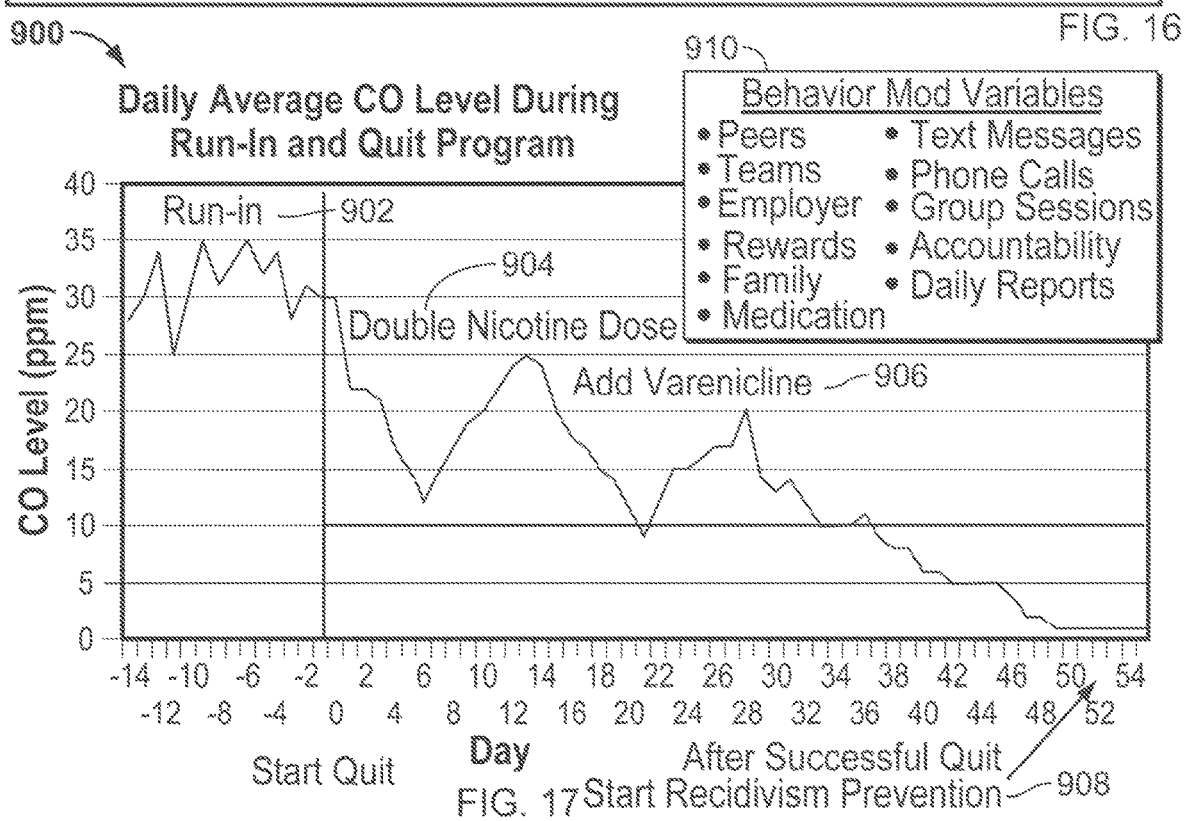
FIG. 17 depicts an illustrative chart of patient SpCO levels during run-in and quit program in accordance with some embodiments of the disclosure.

FIG. 17 shows an illustrative graph 900 for tracking the average daily SpCO trend for a patient running up to and then entering a quit program. The average trend is tracked for each day as it improves. The doctor or counselor may zoom in on a particular day (present or past) to see the granular detail and associations of CO with other parameters measured and associated stressors 910. Visibility of the trend of CO over time in the quit program may prevent patient dropouts, prevent smoking relapse, titrate drugs and counseling, and improve outcomes. For example, data point 902 indicates CO level before the patient entered the quit program. Data points 904 and 906 indicate CO levels as nicotine replacement therapy and varenicline therapy is administered during the quit program. Data point 908 indicates the patient has successfully quit smoking. At this point, the system may recommend the patient enter into a recidivism prevention program to prevent relapse.

In some embodiments, the systems and methods described herein provide for a follow up program after a patient successfully quits smoking. After a successful quit, verified by the system, the patient wears the wearable device, e.g., device 102 or 202, for an extended period of time, e.g., a few months to two years, as an early detection system for relapse. The system may collect data and employ counseling strategies as described above for the quit program.

In some embodiments, a patient receives a wearable device, e.g., device 102 or 202, and an app for their smartphone, e.g., device 104, that allows them to assess health remotely and privately by tracking several different parameters. The patient may submit breath samples or put their finger in or on a sensor on the wearable device several times per day as required. They may wear the wearable device to get more frequent or even continuous measurements. At the end of a test period, e.g., five to seven days or another suitable time period, the processor in the smart phone may calculate their CO exposure and related parameters. FIG. 18 shows an exemplary app screen 1000 showing measurements such as SpCO 1002, SpO2 1004, heart rate 1006, respiratory rate 1008, blood pressure 1010, and body temperature 1012. Warning indicators 1014 and 1016 may be provided for atypical measurements, possibly indicating effects of smoking on the body. The system may prompt the patient with alerts when warning indicators 1014 or 1016 are activated.

The system may recommend the patient enter a smoking cessation program and provide options for such programs. The patient may agree to enter a quit program on seeing such objective evidence of smoking. The system may share this data with the patient's spouse, their doctor, or another suitable stakeholder involved in the patient's quit program. For example, the system may share the data with an application a stakeholder's mobile device or send a message including the data via email, phone, social networking, or another suitable medium. Triggers to get a patient to join the quit program may include spousal suggestion, employer incentive, peer pressure, personal choice, an illness, or another suitable trigger. The patient may initiate the quit program on their own or bring the data to a doctor to receive assistance in joining a quit program.

While the patient is initiated in the quit program, the wearable device, e.g., device 102 or 202, may continue to monitor the patient's health parameters, such as heart rate, movement, location that precede the smoking behavior, and transmit the data to the patient and/or his doctor to improve therapy. The smart phone app on, e.g., device 104, may receive patient entered data including, but not limited to, stressors, life events, location, daily events, administrations of nicotine patches or other formulas, administrations of other drugs for smoking cessation, and other suitable patient entered data.

FIG. 19 shows an illustrative embodiment of an app screen 1100 for receiving patient entered data. App screen 1100 may be displayed when the smart phone app receives an indication of a smoking event, e.g., due to a spike in the CO level for the patient. App screen 1100 prompts the user to enter a trigger for the smoking event. For example, the patient may select from one of options 1102, 1104, 1106, and 1108 as triggering a smoking event or select option 1110 and provide further information regarding the trigger. Other triggers for a smoking event may include phone calls, athletics, sport, stress, sex, and other suitable patient entered data. The patient may voluntarily invoke app screen 1100 as well to enter trigger information for a smoking event. In some embodiments, app screen 1100 for receiving patient data is displayed to the patient during the five-day evaluation period to collect information regarding smoking behavior before the patient enters the quit program.

In some embodiments, the collected data is used by the smart phone app to avert a smoking event. The processor running the app or a processor in another device, such as device 102 or 202 or server 106 or 204, may analyze the information regarding what happens to heart rate and other vital signs in the period leading up to a smoking event. The processor may correlate changes in heart rate, such as tachycardia, that can predict when a patient will smoke. This information may be used to initiate a prevention protocol for stopping the smoking event. For example, the prevention protocol may include delivering a bolus of nicotine. The nicotine may be delivered via a transdermal patch or a transdermal transfer from a reservoir of nicotine stored in the wearable device, e.g., device 102 or 202. In another example, the prevention protocol may include calling the patient's doctor, a peer group, or another suitable stakeholder. The processor may send an instruction to an automated call system, e.g., resident at server 106 or 204, to initiate the call. FIGS. 22 and 23 provide flow diagrams for predicting a smoking event based on patient vital signs and will be described in more detail below.

FIG. 20 shows an illustrative embodiment of an app screen 1200 implementing such a prevention protocol. For example, if a patient tends to become tachycardic twenty minutes before every cigarette, the processor may detect tachycardia and prompt the patient to administer nicotine via option 1202. The patient may vary the nicotine dose via option 1204. In some embodiments, the nicotine is administered automatically. The amount may be determined based on the patient's current SpCO level or another suitable parameter. The patient may receive a call from a peer group via option 1206, a doctor via 1208, or another suitable stakeholder. The caller may provide the patient encouragement to abstain from smoking and suggest seeking out other activities to divert the patient's attention.

In some embodiments, the smart phone app presents the process for the patient as a game to improve visibility of progress. The app may employ patient engagement strategies by providing small frequent or infrequent rewards for group or individual progress to engage the patient. The app may provide employer rewards, payers, spouse, or peer groups to engage the patient. FIG. 21 shows an illustrative app screen 1300 for such an embodiment. App screen 1300 offers the patient a reward for abstaining from smoking for fifteen days. Prompt 1302 challenges the patient to further abstain for another fifteen days. The patient may select option 1304 to accept the reward and continue monitoring progress while he remains smoke free. However, the patient may be having difficulty abstaining and may select option 1306 to be contacted a peer group, a counselor, a family member, a doctor, or another suitable party.

In some embodiments, the patient is a peer and supporter for others in their group. Groups can track each other's progress and give support. For example, the group members may be part of a social network that allows them to view each other's statistics and provide encouragement to abstain from smoking. In another example, a message, e.g., a tweet, may be sent to group members of the patient's social network, e.g., followers, when it is detected the patient is smoking. The message may inform the group members that the patient needs help. The group may connect to the patient in a variety of ways to offer help. This interaction may enable to the patient to further abstain from smoking that day.

Figure 24:
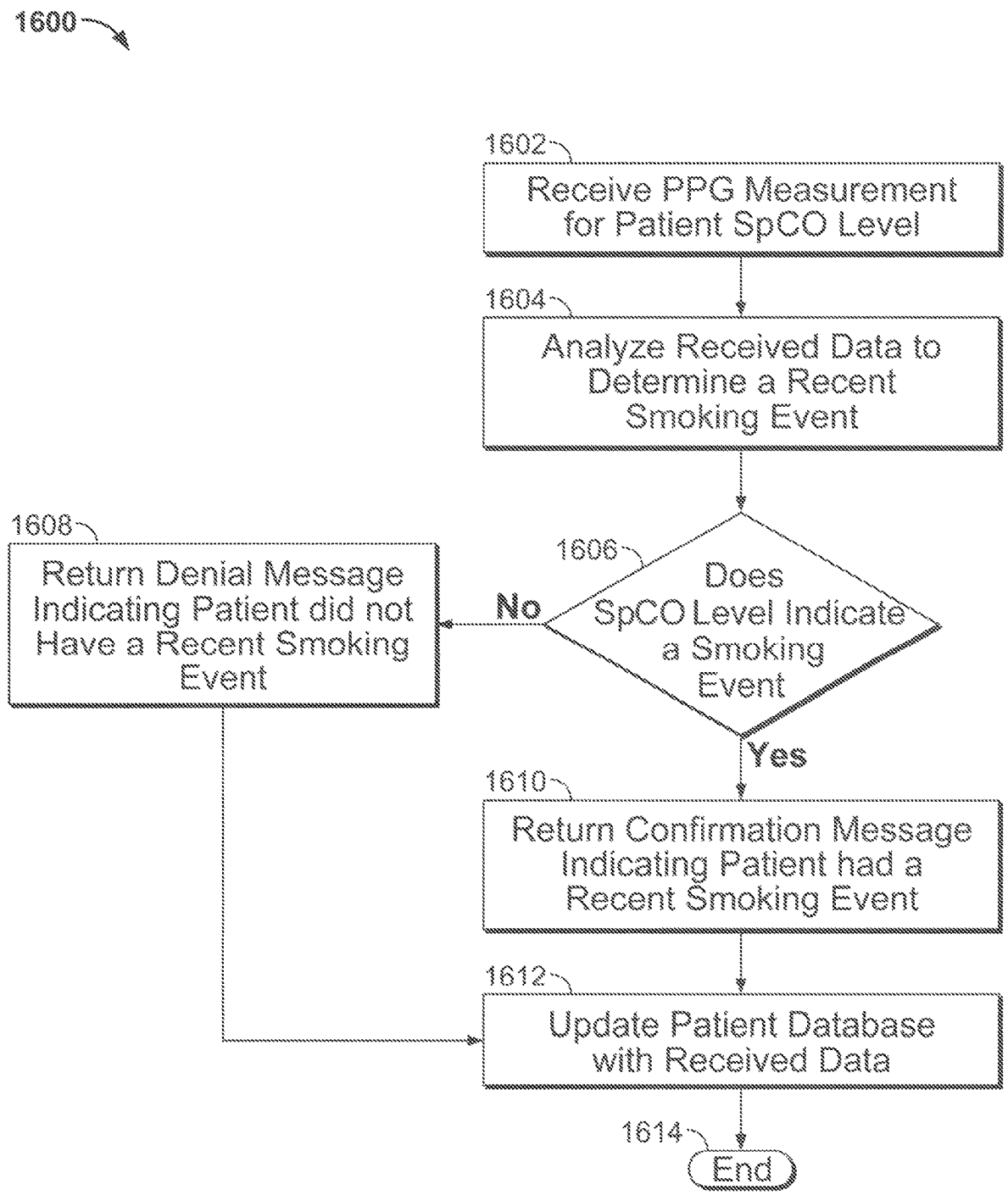
FIG. 24 depicts an illustrative flow diagram for a one-time measurement of the patient's SpCO level using a PPG sensor in accordance with some embodiments of the disclosure.

In some embodiments, at a primary care visit a patient provides a sample and is asked if they smoke. For example, the wearable device, e.g., device 102 or 202, is applied to the patient and receives the sample for a one time on-the-spot measurement of the patient's SpCO level. The SpCO level may exceed a certain threshold which suggests that the patient smokes. FIG. 24 provides a flow diagram for the one-time measurement of the patient's SpCO level. The patient may be provided with the wearable device to wear as an outpatient for a period of time, e.g., one day, one week, or another suitable period of time. Longer wear times may provide more sensitivity in detection of smoking behavior and more accuracy in quantifying the variables related to smoking behavior.

The wearable device, e.g., device 102 or 202, and smart phone app on, e.g., device 104, may continue to monitor the patient's health parameters, such as SpCO level, in real time or near real time and process the data for observation by the patient, the doctor, or any other suitable party. The smart phone app may also offer the data in a digestible form for daily or weekly consumption by the patient and/or the doctor. For example, the smart phone app may generate display similar to FIG. 17 showing daily progress with the option to zoom into a particular day for observing further details. The doctor may log the patient into a healthcare database stored at, e.g., server 106 or 204 in communication with a mobile device running the smart phone app, and continue to receive the data from the smart phone app via the Internet or another suitable communications link. The smart phone app may receive data from the sensors via a wired connection to the mobile device running the app or via a wireless connection such as WI-FI, BLUETOOTH, radio frequency, or another suitable communications link.

The patient and the doctor may set a future quit date and send the patient home without any drugs or with drugs to help the patient quit. The patient may begin working towards the agreed quit date. Feedback from the wearable device and/or the smart phone app may assist the patient to be more prepared at the quit date to actually quit as well as to smoke less at the quit date than when they started at the start. Once the patient starts the quit program, they may get daily or weekly feedback from their spouse, doctor, nurse, counselor, peers, friends, or any other suitable party.

Drug therapy, if prescribed, may be based by the doctor or may be adjusted automatically based on patient performance. For example, the doctor may remotely increase or decrease nicotine dose administration based on the patient's CO, eCO, SpCO level. In another example, a processor in the wearable device, e.g., device 102 or 202, the smart phone, e.g., device 104, or a remote server, e.g., server 106 or 204, may increase or decrease nicotine dose administration based on CO trends from the patient's past measurements. Similarly, the drug therapy may be shortened or lengthened in duration according to collected data.

FIG. 22 depicts an illustrative flow diagram 1400 for predicting a smoking event based on a patient's CO, eCO, SpCO measurements and other suitable factors. The patient may be given a wearable device, e.g., device 102 or 202, and a smart phone app for their mobile phone, e.g., device 104. The wearable device may include a PPG sensor for measuring the patient's SpCO level. At step 1402, a processor in the wearable device or the patient's mobile phone receives a PPG measurement for the patient's SpCO level and associated time and location. The processor may also receive other information such as heart rate, respiration rate, and other suitable factors in predicting a smoking event.

At step 1404, the processor updates a patient database that is stored locally or at a remote location, such as a healthcare database in server 106, with the received patient data. At step 1406, the processor analyzes the current and prior measurements for the patient parameters and determines whether a smoking event is expected. For example, the SpCO trend may be at a local minimum which indicates the user may be reaching for a cigarette to raise their SpCO level. The processor may apply a gradient descent algorithm to determine the local minimum. At step 1408, the processor determines whether the SpCO trend indicates an expected smoking event. If the processor determines a smoking event is not expected, at step 1410, the processor determines if the time and/or location are indicative of an expected smoking event. For example, the processor may determine that the patient typically smokes when they wake up in the morning around 7 a.m. In another example, the processor may determine that the patient typically smokes soon after they arrive at work. In yet another example, the processor may determine that the patient typically smokes in the evening whenever they visit a particular restaurant or bar.

If the processor determines a smoking event is expected from either step 1408 or 1410, at step 1412, the processor initiates a prevention protocol for the patient to prevent the smoking event. Information regarding the prevention protocol may be stored in a memory of device 102, 104, or 202, or server 106 or 204, or a combination thereof. The information for the prevention protocol may include instructions for one or more intervention options to initiate when the patient is about to smoke. For example, the processor may initiate an alarm in the patient's mobile phone and display an app screen similar to FIG. 20. The app screen may offer the patient options to administer nicotine or receive a call from a peer group, a doctor, or another suitable party. Alternatively, the prevention protocol may include automatically administering a bolus of nicotine to the patient from a reservoir of nicotine stored in the patient's wearable device. In another example, the app screen may indicate that a message, e.g., a tweet, will be sent to group members of the patient's social network, e.g., followers, when it is detected the patient has failed to abstain from smoking. The patient may refrain from smoking to prevent the message indicating his failure from being sent out.

In some embodiments, steps 1408 and 1410 are combined into one step or include two or more steps for a processor determining that a smoking event is expected. For example, the processor may determine that a smoking event is expected based on a combination of the SpCO trend, the patient's location, and/or the current time. In another example, the processor may determine that a smoking event is expected based on a series of steps for analyzing one or more of the patient's SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters.

At step 1414, the processor determines whether the prevention protocol was successful. If a smoking event occurred, at step 1418, the processor updates the patient database to indicate that the prevention protocol was not successful. If a smoking event did not occur, at step 1416, the processor updates the patient database to indicate that the prevention protocol was successful. The processor returns to step 1402 to continue receiving the PPG measurement for the patient's SpCO level and associated data. The processor may monitor the patient's vital signs continuously to ensure that the patient does not relapse into a smoking event.

It is contemplated that the steps or descriptions of FIG. 22 may be used with any other embodiment of this disclosure. In addition, the steps and descriptions described in relation to FIG. 22 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 9 (e.g., device 102, 104, or 106) or FIG. 10 (e.g., device 202 or 204) could be used to perform one or more of the steps in FIG. 22.

FIG. 23 depicts an illustrative flow diagram 1500 for determining whether the prevention protocol was successful in relation to step 1414 in FIG. 22. At step 1502, the processor receives patient data for determining whether a smoking event occurred. At step 1504, the processor analyzes currently received patient data and previously received patient data. At step 1506, the processor determines whether a smoking event occurred based on the analysis. For example, if no nicotine was administered but the patient's SpCO levels are currently higher than previous SpCO levels, the processor may determine the patient relapsed and smoked a cigarette. In such a situation, at step 1508, the processor returns a message indicating that the prevention protocol was not successful. In another example, if the patient's vital signs indicate no rise or a drop in SpCO levels, the processor may determine that a smoking event did not occur. In such a situation, at step 1510, the processor returns a message indicating that the prevention protocol was successful.

It is contemplated that the steps or descriptions of FIG. 23 may be used with any other embodiment of this disclosure. In addition, the steps and descriptions described in relation to FIG. 23 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 9 (e.g., device 102, 104, or 106) or FIG. 10 (e.g., device 202 or 204) could be used to perform one or more of the steps in FIG. 23.

FIG. 24 depicts an illustrative flow diagram 1600 for a one-time measurement of the patient's SpCO level using a PPG sensor. For example, the wearable device, e.g., device 102 or 202, is applied to the patient and receives the sample for a one-time measurement of the patient's SpCO level. At step 1602, a processor in the wearable device receives a PPG measurement for the patient's SpCO level and any other suitable data, such as time, location, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. At step 1604, the processor analyzes the received data to determine a recent smoking event. For example, an elevated SpCO level beyond a certain threshold may suggest that the patient has recently smoked a cigarette.

At step 1606, the processor determines whether the patient SpCO level indicates a smoking event has occurred. For example, the SpCO level exceeding a specified threshold may indicate a smoking event. In another example, one or more of shape of the SpCO curve, start point, upstroke, slope, peak, delta, downslope, upslope, time of change, area under curve, and other suitable factors, may indicate a smoking event. One or more of these factors may assist in quantification of the smoking event. For example, the total number of peaks in a given day may indicate the number of cigarettes smoked, while the gradient shape and size and other characteristics of each peak may indicate the intensity and amount of each cigarette smoked. If the processor determines the SpCO level is indicative that a smoking event has not occurred, at step 1608, the processor returns a denial message indicating the patient did not have a recent smoking event. The patient's doctor may find this information useful in evaluating the patient's smoking behavior. If the processor determines the SpCO level is indicative that a smoking event has occurred, at step 1610, the processor returns a confirmation message indicating the patient did have a recent smoking event. In this case, the collected data may be used to set up a quit program for the patient as described above.

After steps 1608 or 1610, at step 1612, the processor updates the patient database to record this information. At step 1614, the processor terminates the SpCO level evaluation for the patient. The patient may be provided with the wearable device to wear as an outpatient for a period of time, e.g., one day, one week, or another suitable period of time. Longer wear times may provide more sensitivity in detection of smoking behavior and more accuracy in quantifying the variables related to smoking behavior.

It is contemplated that the steps or descriptions of FIG. 24 may be used with any other embodiment of this disclosure. In addition, the steps and descriptions described in relation to FIG. 24 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 9 (e.g., device 102, 104, or 106) or FIG. 10 (e.g., device 202 or 204) could be used to perform one or more of the steps in FIG. 24.

In some embodiments, data from one or more devices associated with patients, such as devices 102 and 104 or device 202, are received at a central location, such as server 106 or 204. The patient devices log in real time or near real time multiple biometric and contextual variables. For example, the biometric variables may include CO, eCO, SpCO, SpO2, heart rate, respiratory rate, blood pressure, body temperature, sweating, heart rate variability, electrical rhythm, pulse velocity, galvanic skin response, pupil size, and other suitable biometric variables. For example, the contextual variables may include GPS location, patient activities (e.g., sports, gym, shopping, or another suitable patient activity), patient environment (e.g., at work, at home, in a car, in a bar, or another suitable patient environment), stressors, life events, and other suitable contextual variables. The collected data may also include in-person observation of the patients' smoking behavior. A spouse or friend or buddy may be able to enter data that their patient smoked, correlating that data with the SpCO readings to determine accuracy.

Server 106 includes a processor for receiving data for multiple patients over a period of time and analyzes the data for trends that occur around the time of an actual smoking event. Based on the trends, the processor determines a diagnostic and/or detection test for a smoking event. The test may include one or more algorithms applied to the data as determined by the processor. For example, the processor may analyze a spike in CO level of a patient. Detecting the spike may include determining that the CO level is above a certain specified level. Detecting the spike may include detecting a relative increase in the patient's CO level from a previously measured baseline. The processor may detect a spike as a change in the slope of the patient's CO trend over a period of time. For example, the CO trend moving from a negative slope to a positive slope may indicate a spike in the CO level. In another example, the processor may apply one or more algorithms to changes in heart rate, increasing heart rate variability, changes in blood pressure, or variation in other suitable data in order to detect a smoking event.

Figure 25:
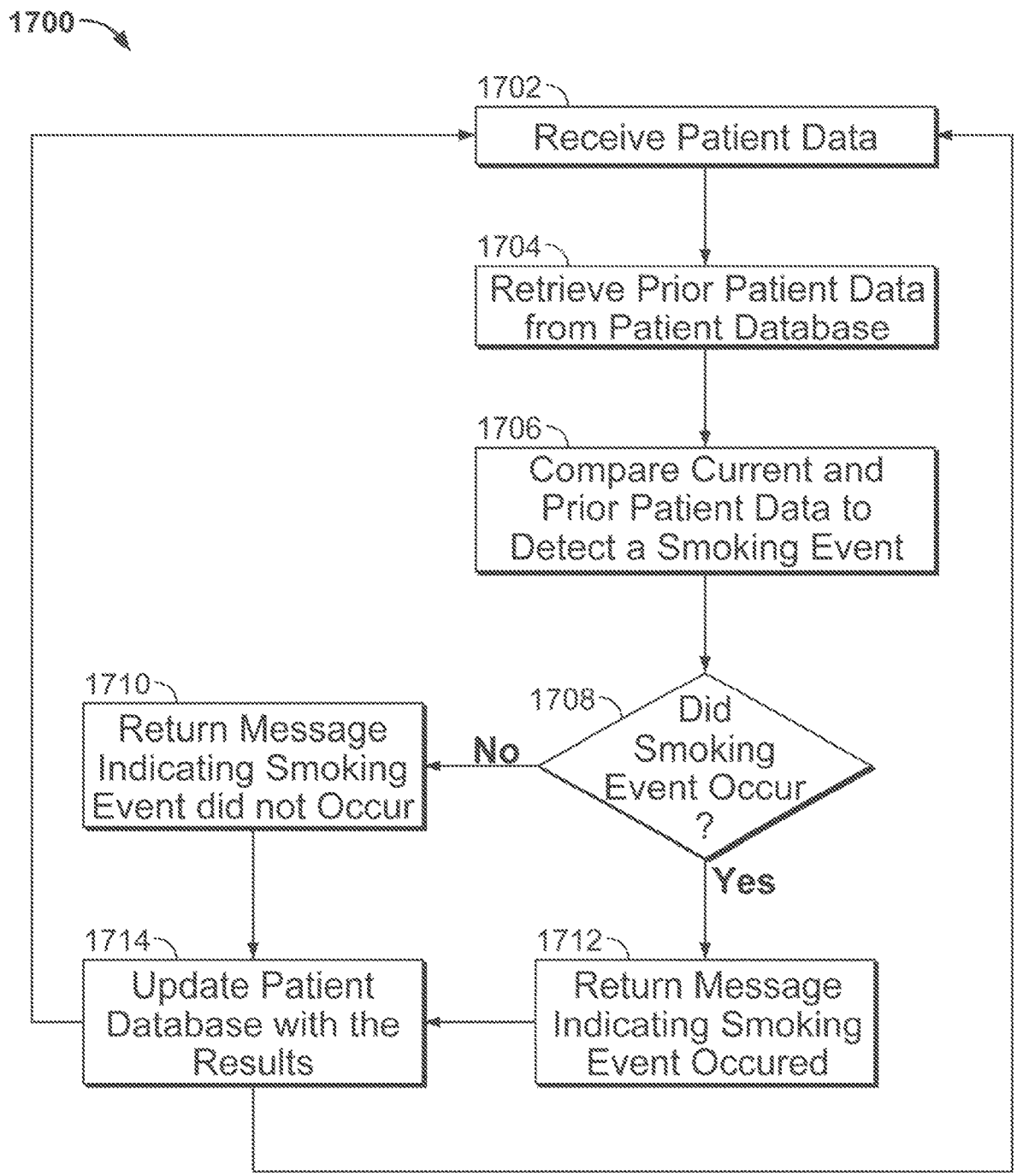
FIG. 25 depicts an illustrative flow diagram for detecting a smoking event in accordance with some embodiments of the disclosure.

FIG. 25 depicts an illustrative flow diagram 1700 for detecting a smoking event as described above. A processor (e.g., in server 106 or 204) may determine a diagnostic and/or detection test for a smoking event according to flow diagram 1700. At step 1702, the processor receives current patient data. At step 1704, the processor retrieves previously stored data for the patient from a database, e.g., a patient database stored at server 106 or 204. At step 1706, the processor compares the current and prior patient data to detect a smoking event. For example, the processor may analyze a spike in CO level of the patient. Detecting the spike may include detecting a relative increase in the patient's CO level from a previously measured baseline. The processor may detect a spike as a change in the slope of the patient's CO trend over a period of time. For example, the CO trend moving from a negative slope to a positive slope may indicate smoking behavior. In another example, the processor may apply one or more algorithms to changes in heart rate, increasing heart rate variability, changes in blood pressure, or variation in other suitable data in order to detect a smoking event. At step 1708, the processor determines whether a smoking event occurred based on, e.g., a spike in CO level of the patient as described. If no smoking event is detected, at step 1710, the processor returns a message indicating that a smoking event did not occur. If a smoking event is detected, at step 1712, the processor returns a message indicating that a smoking event occurred. At step 1714, the processor updates the patient database with the results from either step 1710 or 1712.

It is contemplated that the steps or descriptions of FIG. 25 may be used with any other embodiment of this disclosure. In addition, the steps and descriptions described in relation to FIG. 25 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 9 (e.g., device 102, 104, or 106) or FIG. 10 (e.g., device 202 or 204) could be used to perform one or more of the steps in FIG. 25.

In some embodiments, the processor analyzes initially received data to measure when a person smokes and ties the algorithm to a variable that triggers the algorithm for diagnosing and/or detecting a smoking event. The processor continues to analyze other variables as additional patient data is received. The processor may determine another variable that changes when the patient smokes and instead use that variable to trigger the algorithm. For example, the processor may opt to use the other variable because it is less invasive or easier to measure than the initially selected variable.

In some embodiments, the algorithm for detecting a smoking event has a high sensitivity. Sensitivity is defined as a percentage of the number of actual smoking events detected by the sensor and algorithm. For example, if a patient smokes 20 times in one day, and the algorithm identifies every smoking event, it is 100% sensitive.

In some embodiments, the algorithm for detecting a smoking event has a high specificity. Specificity is defined as the ability of the test to not make false positive calls of a smoking event (i.e., positive test with no smoking event present). If the sensor and algorithm do not make any false positive calls in a day, it has 100% specificity.

In another example, if a patient smokes 20 times and the algorithm identifies 18 of the 20 actual smoking events and indicates 20 other false smoking events, it has 90% sensitivity (i.e., detected 90% of smoking events) and 50% specificity (i.e., over called the number of smoking events by 2×).

In some embodiments, after the processor determines one or more algorithms and applies to SpCO measurements to detect a smoking event with adequate sensitivity and specificity, the processor determines whether there is an association of other biometric variables or contextual variables with the SpCO results that could be used on their own (without SpCO) to detect a smoking event. The processor may determine another variable that changes when the patient smokes and instead use that variable to trigger the algorithm. For example, the processor may opt to use the other variable because it is less invasive or easier to measure or more reliable than the initially selected variable.

In some embodiments, the processor analyzes received patient data to predict a smoking event likelihood before it happens. The processor may analyze received patient data over a period of time, e.g., five minutes, 10 minutes, 15 minutes, 20 minutes, or another suitable time interval, before a smoking event to determine one or more triggers. For example, some smoking events may be preceded by contextual triggers (e.g., at a bar, before, during, or after eating, before, during, or after sex, or another suitable contextual trigger). In another example, some smoking events may be preceded by changes in a biometric variable, e.g., heart rate or another suitable biometric variable. The determined variables may overlap with those selected for diagnosis and detection and therefore may be used for prediction as well. Alternatively, the determined variables may not overlap with those selected for diagnosis.

The processor may inform patients of a smoking event likelihood and trigger a prevention protocol (e.g., as discussed with respect to FIGS. 22 and 23) to prevent smoking change behavior. The processor detects smoking events for a patient entered in, e.g., a quit program, and tracks and analyses trends in received patient data. The processor may determine goals for the patient and reward them when he achieves the set goals (e.g., as discussed with respect to FIG. 21). The processor may predict when a patient is about to smoke and intervene just in time by suggesting a call to a peer group or a physician or by administering a bolus of nicotine (e.g., as discussed with respect to FIG. 20).

In one example, the processor predicts smoking events for the patient based on 75% of the patient's smoking events, during diagnosis, being preceded by increased heart rate (or a suitable change in another variable). During the quit program, the processor may apply one or more algorithms to received patient data to predict smoking events and initiate a prevention protocol. For example, the prevention protocol may engage the patient just in time by putting the patient in contact with supporters, such as a doctor, a counselor, a peer, a team member, a nurse, a spouse, a friend, a robot, or another suitable supporter. In some embodiments, the processor applies algorithms to adjust settings, such as baseline, thresholds, sensitivity, and other suitable settings, for each patient based on their five-day run-in diagnostic period. The processor may then use these customized algorithms for the specific patient's quit program. The described combination of techniques to alter smoking behavior in a patient may be referred to as a digital drug.

In some embodiments, the processor detects smoking in a binary manner with a positive or a negative indication. The processor initially uses observational studies and SpCO measurements from the patient to detect smoking behavior. For example, the processor receives data regarding true positives for smoking events from observational data for the patient's smoking behavior. The processor determines if detection based on SpCO measurements matches true positives for smoking events. If there is a match, the processor applies algorithms to other received patient data including patient's SpCO, SpO2, heart rate, respiratory rate, blood pressure, body temperature, sweating, heart rate variability, electrical rhythm, pulse velocity, galvanic skin response, pupil size, geographic location, environment, ambient temperature, stressors, life events, and other suitable parameters. The processor determines whether any patterns in non-SpCO variable data are also indicative of a smoking event. Such variables may be used in algorithms for non-SpCO devices, such as wearable smart watches or heart rate monitor straps or other devices, to detect smoking events.

The processor may quantify smoking behavior when it is detected based on the received patient data. For example, the processor analyzes SpCO data trends to indicate how intensely the patient smoked each cigarette, how many cigarettes the patient smoked in one day, how much of each cigarette was smoked, and/or how long it took to smoke each cigarette. The processor may use other biometric or contextual variables for the indications as well. The processor uses the received patient data to predict the likelihood for a smoking event to occur in the near future, e.g., in the next 10 minutes. The processor may analyze the received patient data over a preceding period of time, e.g., five minutes, 10 minutes, 15 minutes, 20 minutes, or another suitable time interval, before a smoking event to determine one or more triggers.

In some embodiments, the systems and methods described herein provide for evaluating smoking behavior of a patient. During a five-day testing period, the patient behaves as they normally would. Devices 102, 104, and/or 106 or devices 202 and/or server 204 receive patient data relating to the patient's smoking behavior. There is very little to no engagement of the patient as the purpose of the testing period is to observe the patient's smoking patterns.

The testing period may be extended to a second five-day period if needed. Alternatively, the first and second periods may be shorter, e.g., two or three days, or longer, e.g., a week or more. Before the second testing period, the processor determines a model of how the patient smokes.

In the second testing phase, the processor applies a series of perturbations to the model to see if the smoking behavior changes. There may be several types of perturbations, each with several dimensions. For example, the perturbation may be whether sending a text message before or during a smoking event causes the smoking event to be averted or shortened. Dimensions within the perturbation may be different senders, different timing, and/or different content for the text messages. In another example, the perturbation may be whether a phone call at certain times of the day or before or during a smoking event causes the smoking event to be averted or shortened. Dimensions within the perturbation may be different callers, different timing, and/or different content for the phone calls. In yet another example, the perturbation may be whether alerting the patient to review their smoking behavior at several points in the day averts smoking for a period of time thereafter. Dimensions may include determining whether and when that aversion extinguishes. In other examples, the perturbations may be rewards, team play, or other suitable triggers to avert or shorten the patient's smoking events.

In some embodiments, the processor delivers perturbations to the smoking model for the patient using a machine learning process. The machine learning process delivers perturbations, tests the results, and adjusts the perturbation accordingly. The processor determines what works best to achieve an identified behavior change by trying options via the machine learning process. The machine learning process may be applied during the second testing phase as slight perturbations. The machine learning process may be also be applied with significant perturbations during the patient's quit phase to increase efforts to try to get the patient to quit smoking or to continue to abstain from smoking.

Figure 26:
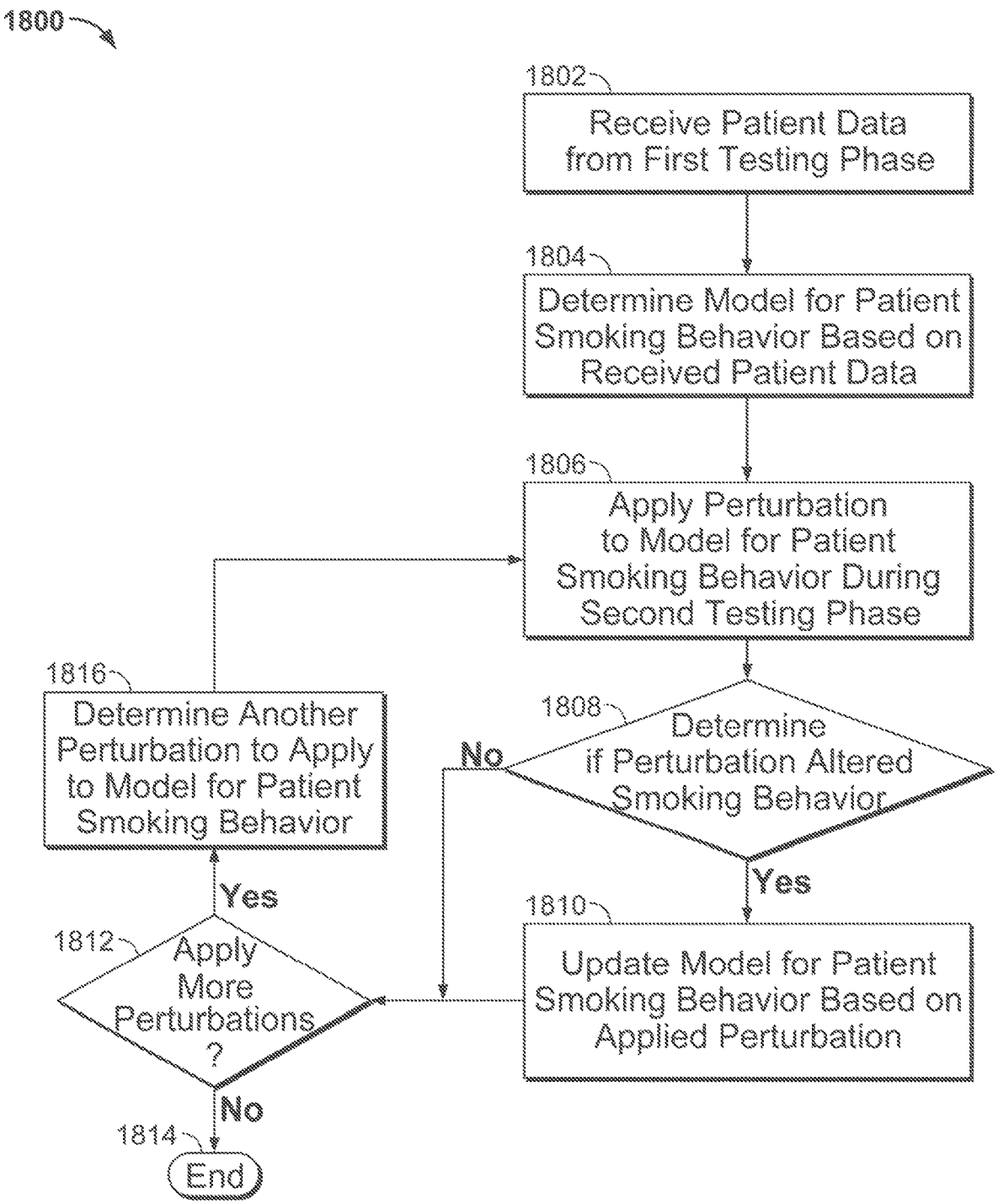
FIG. 26 depicts an illustrative flow diagram for applying one or more perturbations to a model for a patient's smoking behavior in accordance with some embodiments of the disclosure.

FIG. 26 depicts an illustrative flow diagram 1800 for applying one or more perturbations to the smoking model for the patient in the second testing phase. At step 1802, a processor in wearable device 102 or 202, mobile device 104, or server 106 or 204 receives patient data relating to the patient's smoking behavior in the first testing phase. At step 1804, the processor analyzes the received patient data to determine a model for the patient's smoking behavior. At step 1806, the processor applies one or more perturbations to the model to see if the smoking behavior changes. The perturbation may be applied to the model using a machine learning process. There may be several types of perturbations, each with several dimensions. For example, the perturbation may be whether sending a text message before or during a smoking event causes the smoking event to be averted or shortened. Dimensions within the perturbation may be different senders, different timing, and/or different content for the text messages.

At step 1808, the processor determines whether the perturbation altered the patient's smoking behavior. For example, the processor determines whether receiving a text message before or during a smoking event caused the patient to abstain from or shorten his smoking. If the perturbation caused a change in the patient's smoking behavior, at step 1810, the processor updates the model for the patient's smoking behavior to reflect the positive result of the applied perturbation. The processor then proceeds to step 1812. Otherwise, the processor proceeds directly to step 1812 from step 1808 and determines whether to apply another perturbation or a variation in the dimensions of the present perturbation. The processor may use the machine learning process to determine whether to apply additional perturbations to the model. If no more perturbations need to be applied, at step 1814, the processor ends the process of applying perturbations.

If more perturbations need to be applied, at step 1816, the processor determines another perturbation to apply to the model. For example, the processor may adjust the present perturbation to send a text message to the patient at a different time or with different content. In another example, the processor may apply a different perturbation by initiating a phone call to the patient before or during a smoking event. The processor returns to step 1806 to apply the perturbation to the model. The processor may use the machine learning process to deliver a perturbation, test the result, and adjust the perturbation or selected another perturbation accordingly. In this manner, the processor determines what works best to achieve an identified behavior change for the patient by trying different options via the machine learning process.

It is contemplated that the steps or descriptions of FIG. 26 may be used with any other embodiment of this disclosure. In addition, the steps and descriptions described in relation to FIG. 26 may be done in alternative orders or in parallel to further the purposes of this disclosure. For example, each of these steps may be performed in any order as appropriate or in parallel or substantially simultaneously to reduce lag or increase the speed of the system or method. Furthermore, it should be noted that any of the devices or equipment discussed in relation to FIG. 9 (e.g., device 102, 104, or 106) or FIG. 10 (e.g., device 202 or 204) could be used to perform one or more of the steps in FIG. 26.

In an illustrative example, a 52-year old male patient is incentivized by his employer to get screened for smoking behavior. The patient enters an evaluation program on Jun. 1, 2015. The patient reports smoking 20 cigarettes per day. The program coordinator, such as a physician or counselor, loads an app on the patient's smart phone, e.g., mobile device 104, and gives the patient a connected sensor, e.g., wearable device 102 or 202. The coordinator informs the patient to smoke and behave normally for a five-day testing period and respond to prompts from the app as they arise. After the five-day period is over, the coordinator enters the patient into a supplementary testing period where the app prompts a bit more often (e.g., to apply perturbations). The coordinator informs the patient that it is up to him at that point to respond however he wishes. The coordinator establishes a targeted date of Jun. 10, 2015 to include 10 days of testing.

After the five-day testing period, the coordinator receives a report (e.g., a five-day report card as discussed with respect to FIG. 16). The report indicates 150 cigarette smoking events detected using CO as compared to 100 cigarette smoking events based on the patient's estimate. The report indicates that associated contextual variables include alcohol, location, stress, and other suitable data. The report indicates that associated biometric variables include increased heart rate, without exercise, as preceding 50% of smoking events. The report indicates that prompts for stress levels showed increased stress in 20% of smoking events.

During the supplementary five-day test period, a processor in the mobile device, e.g., device 104, the wearable device, e.g., device 102 or 202, or a remote server, e.g., server 106 or 204, applies perturbations via a machine learning process. For example, the mobile device prompts the patient four-time times a day with a display including number of cigarettes smoked, intensity of smoking, and time of day. As the day progresses, the prompts cause the patient to reduce smoking for longer periods of time. The net effect is that the patient smokes fewer cigarettes in the second half of day as compared to the first half. In another example, the mobile device prompts the patient at 10 am every day with a display including number of cigarettes smoked the previous day. The net effect is studied as to how the prompt impacts the patient's smoking behavior for the rest of day. The machine learning process may adjust time and content of the display to alter the dimensions of the perturbation as required.

In another example, the processor applies a perturbation via a machine learning process in the form of a text message sent to the patient during a smoking event. The machine learning process varies the dimensions of the perturbation by having different senders, different timing, sending before or during smoking, different content of message, different images in the message, and/or different rewards for abstaining. In another example, the processor applies a perturbation via a machine learning process in the form of a phone call to the patient during a smoking event. The machine learning process varies the dimensions of the perturbation by having different callers, different timing, calling before or during smoking, different content of call, different tones in the call, and/or different rewards for abstaining.

In another example, the processor applies a perturbation via a machine learning process in the form of a prompt for a particular activity on the patient's mobile device. The prompt indicates that the patient is smoking but should consider smoking only half a cigarette and then get outside. During long times between cigarette events, or when an event is predicted, the machine learning process applies perturbations to attempt to avert the smoking event completely. For example, the mobile device displays a prompt notifying the patient that they are in a high-risk zone and should consider an alternative activity or location or phone a friend.

After the testing period, the coordinator enters the patient into the quit program. During the quit period, the processor receives patient data and applies algorithms to the data as described. The processor uses all data from the first and second testing periods to customize the algorithms and starting regimen and quit program interventions for the specific patient. The diagnostic and detection algorithms may use one or more biometric variables for the patient, such as SpCO, to detect smoking behavior. The quit program includes a nicotine regimen starting on day one as part of the nicotine replacement therapy. The nicotine may be delivered via a transdermal patch or a transdermal transfer from a reservoir of nicotine stored in the wearable device given to the patient. The processor applies algorithms to the received patient data to determine the most effective interventions. The processor applies the interventions and further adjusts them as required. The processor may set goal event counts and determine which method works best for altering the patient's smoking behavior. The processor may invoke multiple personalized interventions from stakeholders as perturbations via the machine learning process and test which works best for altering the patient's smoking behavior. The perturbations with the most impact on the patient's smoking model may be retained, while those with less or no impact may not be used further.

While exemplary embodiments of the systems and methods described above focus on smoking behaviors, examples of which include but are not limited to smoking of tobacco via cigarettes, pipes, cigars, and water pipes, and smoking of illegal products such as marijuana, cocaine, heroin, and alcohol related behaviors, it will be immediately apparent to those skilled in the art that the teachings of the present invention are equally applicable to any number of other undesired behaviors. Such other examples include: oral placement of certain substances, with specific examples including but not limited to placing chewing tobacco and snuff in the oral cavity, transdermal absorption of certain substances, with specific examples including but not limited to application on the skin of certain creams, ointments, gels, patches or other products that contain drugs of abuse, such as narcotics, and LSD, and nasal sniffing of drugs or substances of abuse, which includes but is not limited to sniffing cocaine.

In general, the basic configuration of devices 102 and 104 or device 202, as well as related steps and methods as disclosed herein will be similar as between the different behaviors that are being addressed. The devices may differ somewhat in design to account for different target substances that are required for testing or different testing methodology necessitated by the different markers associated with particular undesired behaviors.

It will also be appreciated by persons of ordinary skill in the art that a patient participating in a formal cessation program may take advantage of the systems and methods disclosed herein as adjuncts to the cessation program. It will be equally appreciated that the patient may be independently self-motivated and thus beneficially utilize the systems and methods for quitting the undesired behavior unilaterally, outside of a formal cessation program.

In further exemplary embodiments, the systems and methods disclosed herein may be readily adapted to data collection and in particular to collection of reliable and verifiable data for studies related to undesired behaviors for which the present invention is well suited to test. Such studies may be accomplished with virtually no modification to the underlying device or methods except that where treatment was not included there would not necessarily be a need for updating of the test protocol or treatment protocol based on user inputs.

Figure 27:
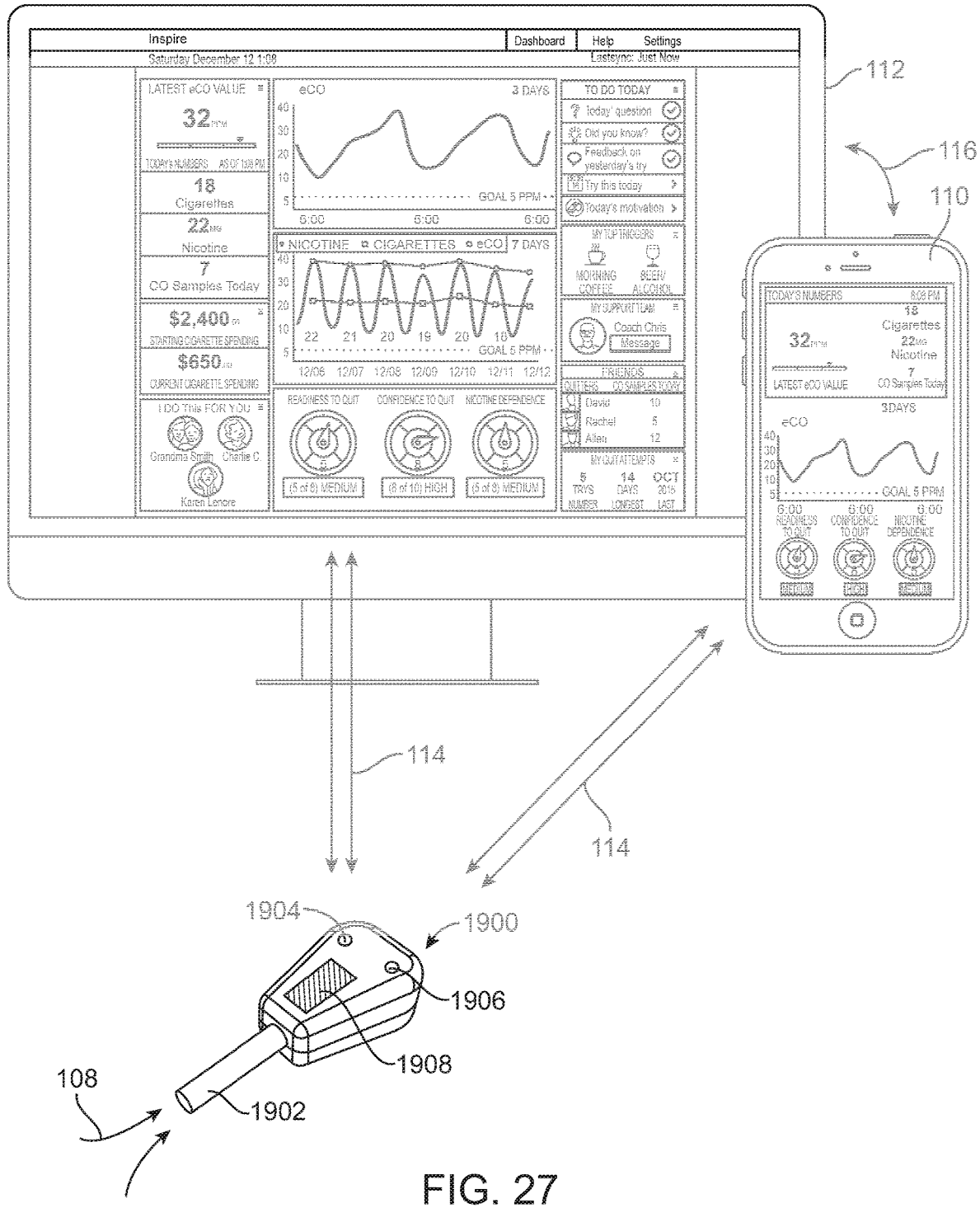
FIG. 27 illustrates another variation of a system and/or method for affecting an individual's smoking behavior using a number of the aspects described herein as well as further quantifying an exposure of the individual to cigarette smoke.

FIG. 27 illustrates another variation of a system and/or method for affecting an individual's smoking behavior using a number of the aspects described herein as well as further quantifying an exposure of the individual to cigarette smoke. In the illustrated example, a plurality of samples of biometric data are obtained from the individual and analyzed to quantify the individual's exposure to cigarette smoke such that the quantified information can be relayed to the individual, a medical caregiver, and/or other parties having a stake in the individual's health. The example discussed below employs a portable device 1900 that obtains a plurality of samples of exhaled air from the individual with commonly available sensors that measure an amount of carbon monoxide within the sample of exhaled air (also referred to as exhaled carbon monoxide or ECO). However, the quantification and information transfer are not limited to exposure of smoking based on exhaled air. As noted above, there are many sampling means to obtain an individual's smoking exposure. The methods and devices described in the present example can be combined or supplemented with such sampling means where possible while still remaining with the scope of the invention. In addition, while the present example discusses the use of a portable sampling unit, the methods and procedures described herein can be used with a dedicated or non-portable sampling unit.

The measurement of exhaled CO level has been known to serve as an immediate, non-invasive method of assessing a smoking status of an individual. See for example, *The*

*Measurement of Exhaled Carbon Monoxide in Healthy Smokers and Non-smokers*, S. Erhan Devecia, et al., Department of Public Health, Medical Faculty of Firat University, Elazig, Turkey 2003 and *Comparison of Tests Used to Distinguish Smokers from Nonsmokers*, M. J. Jarvis et al. American Journal of Public Health, November 1987, V77, No. 11. These articles discuss that exhaled CO ("eCO") levels for non-smokers can range between 3.61 ppm and 5.6 ppm. In one example, the cutoff level for eCO was above 8-10 ppm to identify a smoker.

Turning back to FIG. 27, as shown a portable or personal sampling unit 1900 communicates with either a personal electronic device 110 or a computer 112. Where the personal electronic device 110 includes, but is not limited to a smart phone, ordinary phone, cellular phone, or other personal transmitting device exclusively designed for receiving data from the personal sampling unit 1900). Likewise, the computer 112 is intended to include a personal computer, local server, or a remote server. Data transmission 114 from the personal sampling unit 1900 can occur to both or either the personal electronic device 110 and/or the computer 112. Furthermore, synchronization 116 between the personal electronic device 110 and the computer 112 is optional. Either the personal electronic device 110, the computer 112, and/or the personal sampling unit 1900 can transmit data to a remote server for data analysis as described herein. Alternatively, data analysis can occur, fully or partially, in a local device (such as the computer or personal electronic device). In any case, the personal electronic device 110 and/or computer 112 can provide information to the individual, caretaker, or other individual as shown in FIG. 27.

In the depicted example of FIG. 27, the personal sampling unit 1900 receives a sample of exhaled air 108 from the individual via a collection tube 1902. Hardware within the personal sampling unit 1900 includes any commercially available electrochemical gas sensor that detects carbon monoxide (CO) gas within the breath sample, commercially available transmission hardware that transmits data 114 (e.g., via Bluetooth, cellular, or other radio waves to provide transmission of data). The transmitted data and associated measurements and quantification are then displayed on either (or both) a computer display 112 or a personal electronic device 110. Alternatively, or in combination, any of the information can be selectively displayed on the portable sampling unit 1900.

The personal sampling unit (or personal breathing unit) can also employ standard ports to allow direct-wired communication with the respective devices 110 and 112. In certain variations, the personal sampling unit 1900 can also include memory storage, either detachable or built-in, such the memory permits recording of data and separate transmission of data. Alternatively, the personal sampling unit can allow simultaneous storage and transmission of data. Additional variations of the device 1900 do not require memory storage. In addition, the unit 1900 can employ any number of GPS components, inertial sensors (to track movement), and/or other sensors that provide additional information regarding the patient's behavior.

The personal sampling unit 1900 can also include any number of input trigger (such as a switch or sensors) 1904, 1906. As described below, the input trigger 1904, 1906 allow the individual to prime the device 1900 for delivery of a breath sample 108 or to record other information regarding the cigarette such as quantity of cigarette smoked, the intensity, etc. In addition, variations of the personal sampling unit 1900 also associate a timestamp of any inputs to the device 1900. For example, the personal sampling unit 1900 can associate the time at which the sample is provided and provide the measured or inputted data along with the time of the measurement when transmitting data 114. Alternatively, the personal sampling device 1900 can use alternate means to identify the time that the sample is obtained. For example, given a series of samples rather than recording a timestamp for each sample, the time periods between each of the samples in the series can be recorded. Therefore, identification of a timestamp of any one sample allows determination of the time stamp for each of the samples in the series.

In certain variations, the personal sampling unit 1900 is designed such that it has a minimal profile and can be easily carried by the individual with minimal effort. Therefore, the input triggers 1904 can comprise low profile tactile switches, optical switches, capacitive touch switches, or any commonly used switch or sensor. The portable sampling unit 1900 can also provide feedback or information to the user using any number of commonly known techniques. For example, as shown, the portable sampling unit 1900 can include a screen 1908 that shows select information as discussed below. Alternatively, or in addition, the feedback can be in the form of a vibrational element, an audible element, and a visual element (e.g., an illumination source of one or more colors). Any of the feedback components can be configured to provide an alarm to the individual, which can serve as a reminder to provide a sample and/or to provide feedback related to the measurement of smoking behavior. In addition, the feedback components can provide an alert to the individual on a repeating basis in an effort to remind the individual to provide periodic samples of exhaled air to extend the period of time for which the system captures biometric (such as eCO, CO levels, etc.) and other behavioral data (such as location either entered manually or via a GPS component coupled to the unit, number of cigarettes, or other triggers). In certain cases, the reminders can be triggered at higher frequency during the initial program or data capture. Once sufficient data is obtained, the reminder frequency can be reduced.

Figure 28A:
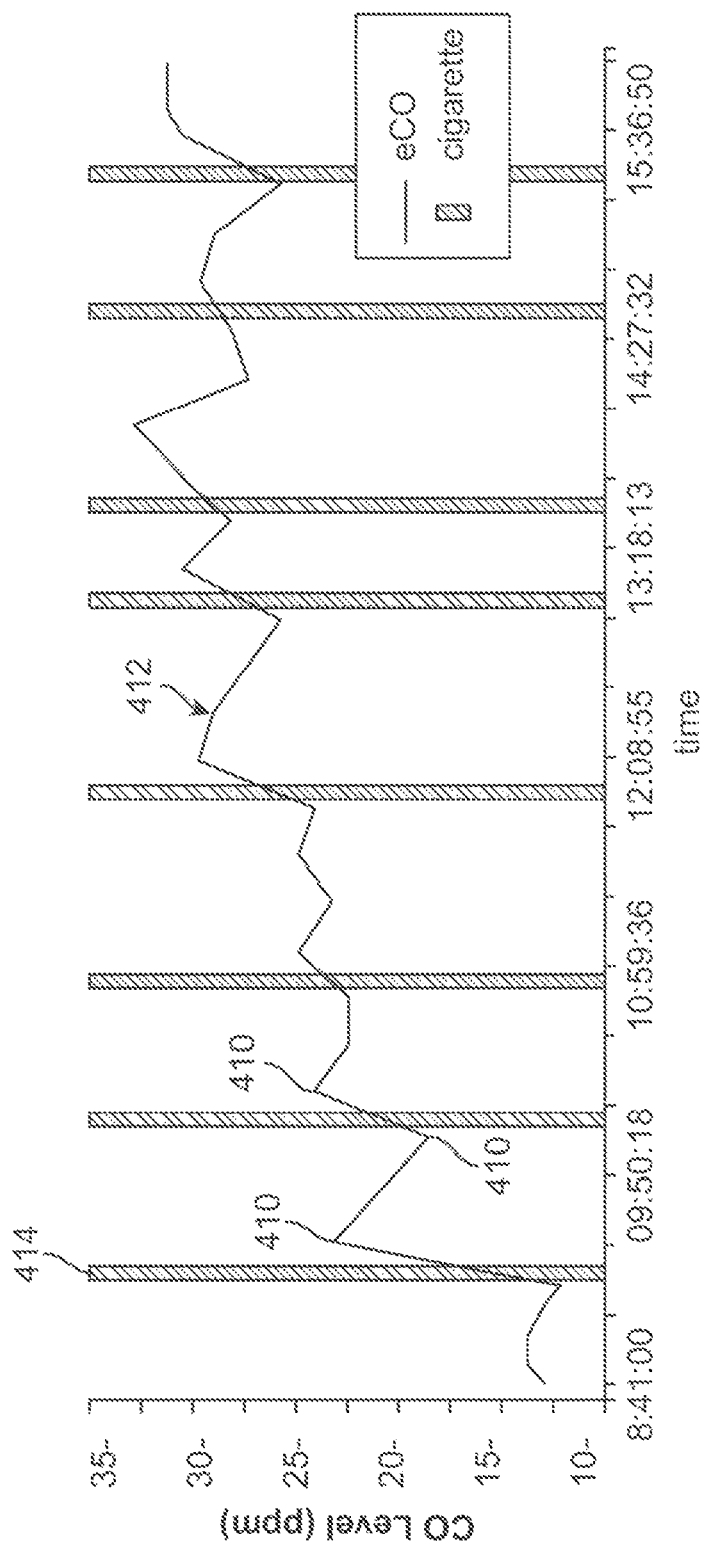
FIG. 28A illustrates a visual representation of data that can be collected with variations of the system shown in FIG. 27.

FIG. 28A illustrates a visual representation of data that can be collected with variations of the system shown in FIG. 27. As discussed above, an individual provides breath samples using the portable sampling unit. The individual can be reminded at a regular interval or at random intervals depending upon the nature of the treatment or intervention program. Each sample is evaluated by one or more sensors within the portable sampling unit to measure an amount of CO. The CO measurements typically correspond to the inflection points 410 on the graph of FIG. 28A. Each CO measurement 410 corresponds to a timestamp as shown in the horizontal axis. The data accumulated via the portable sampling unit allows for the collection of a dataset comprising at least the CO measurement and time of the sample which can be graphed to obtain an eCO curve which is indicative of the amount of CO attributable to the smoking behavior of the individual over the course of the time period.

As noted herein, the individual can further track additional information such as smoking of a cigarette. The smoking of the cigarette can be associated with its own time stamp as shown by bar 414. In one variation of the method and system under the present disclosure, the individual can use the input triggers on the portable sampling unit to enter the number of cigarettes smoked or a fraction thereof. For example, each actuation of the input trigger can be associated with a fractional amount of a cigarette (e.g., ½, ⅓, ¼, etc).

Figure 28B:
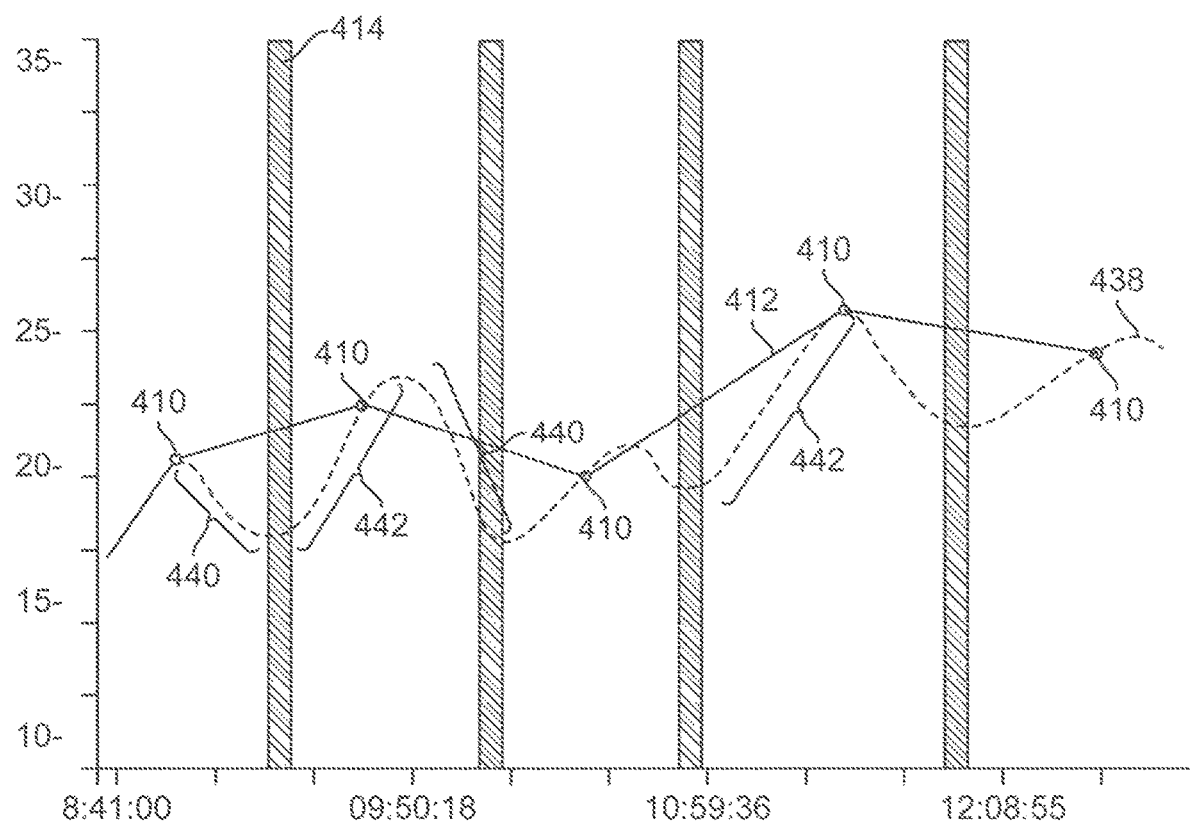
FIG. 28B illustrates a visual representation of data that can be collected with variations of the system shown in FIG. 27.

FIG. 28B illustrates a portion of a graphic representation of data collected as described above. However, in this variation, the quantification of an individual's smoking behavior can use behavioral data to better approximate the CO value between eCO readings. For example, in some variations, eCO measurements between any two points 410 can be approximated using a linear approximation between the two points. However, it is known that, in the absence of being exposed to new CO, the CO level decay within the bloodstream. This decay can be approximated using a standard rate, a rate based on the biometric information of the patient (weight, heartbeat, activity, etc.) As shown in FIG. 28B, when the patient is between cigarettes 414, the calculated CO level can follow a decay rate 440. Once the individual records a cigarette 414, the CO increase 442 can again be approximated, either by using a standard rate or one that is calculated using biometric data as discussed above, or based on the intensity, duration, and amount of cigarettes smoked. Accordingly, the methods and system described herein can optionally use an improved (or approximated) eCO curve 438 using the behavioral data discussed above. Such an improved eCO rate can also be used to determine an improved eCO curve 438 while the individual sleeps. This improved eCO curve can then provide an improved eCO load as described herein. The biometric information used to determine decay rate can be measured by the portable sampling device or by external biometric measuring devices that communicate with the system.

This approximated or improved eCO curve 438 can be displayed to the individual (or to a third party) as a means to help change behavior as the individual can view a real time approximated CO level (i.e., the rate of decrease when not smoking and the rate of increase when smoking). Additional information can also be displayed, for example, the system can also calculate the amount of CO increase with each cigarette based on their starting CO value.

Figure 29:
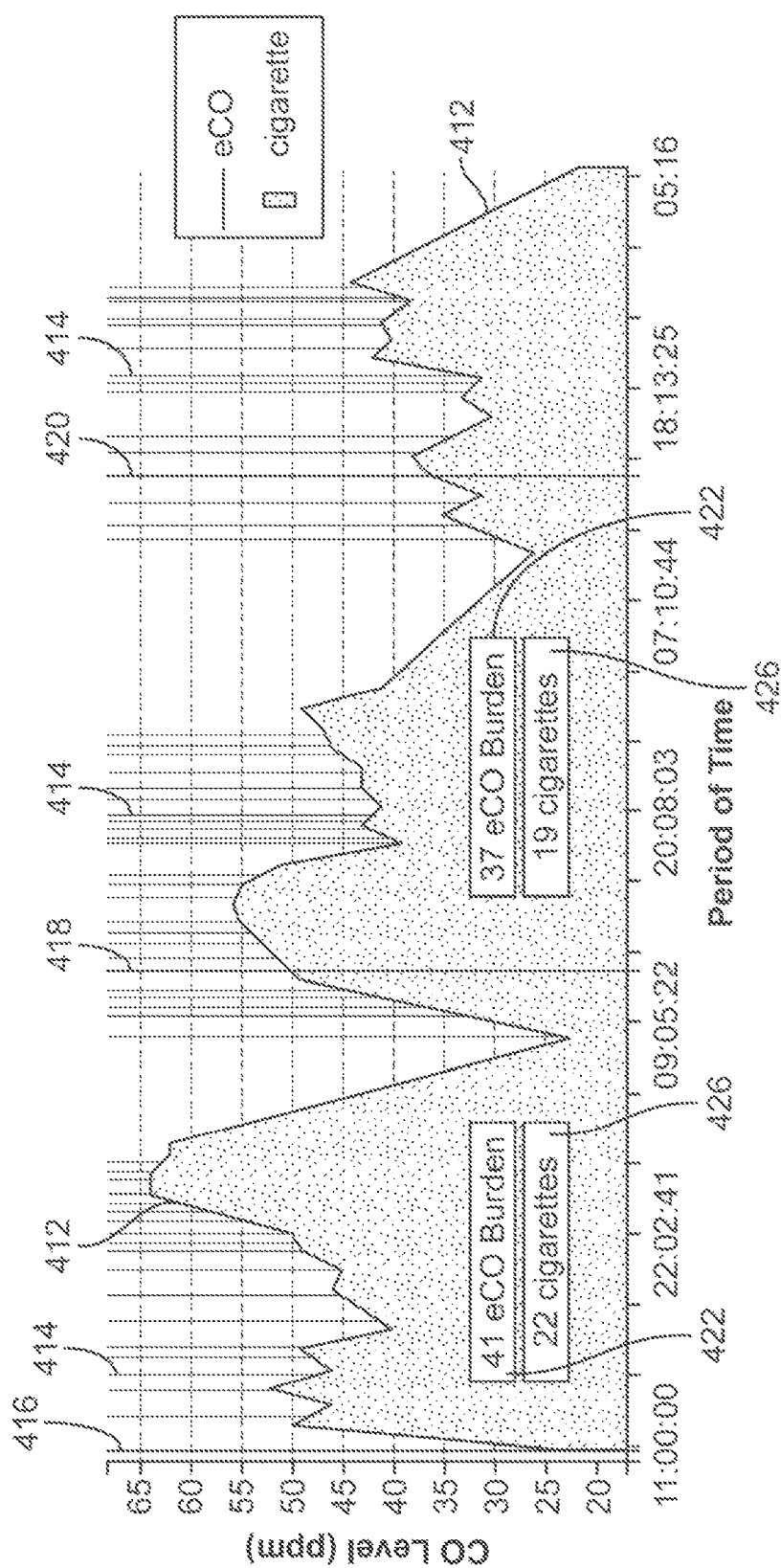
FIG. 29 illustrates an example of a dataset used to determine the eCO curve over a period of time where the eCO attributable to the smoking behavior of the individual can be quantified over various intervals of time to determine an eCO Burden or eCO Load for each interval.

FIG. 29 illustrates an example of a dataset used to determine the eCO curve 412 over a period of time where the eCO attributable to the smoking behavior of the individual can be quantified over various intervals of time to determine an eCO Burden or eCO Load for each interval. As shown, the period of time extends along the horizontal axis and comprises historical and ongoing data captured/transmitted by the portable sampling unit. In order to provide more effective feedback to the individual regarding their smoking behavior, the eCO curve 412 during a certain time interval can be quantified. In the illustrated example, the interval of time between times 416 and 418 comprises a 24-hour interval of time. A subsequent 24-hour interval is defined between times 418 and 420. The interval of time or time interval can comprise any time between two points within the period of time spanned by the dataset. In most cases, the interval of time will be compared to other intervals of time having the same time duration (i.e., where each interval can comprise M minutes, H hours, D days, etc.).

One way of quantifying the eCO Burden/Load over the interval of time is to obtain the area defined by or underneath the eCO curve 412 between a given interval of time (e.g., 416 to 418, 418 to 420, etc.) using the dataset as shown in the graph of FIG. 29. In the illustrated example, the eCO Burden/Load 422 for the first interval (416 to 418) comprises 41 (measured in COppm*t), while the eCO Burden 422 for the second interval (418 to 420) comprises 37. As noted above, along with the eCO Burden/Load 422, the dataset can include the number of cigarettes smoked 414 along with the timestamp of each cigarette. This cigarette data can also be summarized 426 along with the eCO Burden/Load 422 for any given interval of time. In the illustrated example, the eCO Burden/Load is a daily load, which allows the individual to track their CO exposure. Determining a CO Load is a more accurate reflection of total smoke exposure compared to simply counting cigarettes because smokers smoke differently. One smoker may smoke the entire cigarette fully and deeply and intensely, while another smokes less deeply and intensely. While both individuals may smoke one pack per day, the former will have a much higher Daily CO Load due to the intensity that the smoke is inhaled. CO Load is also important as when an individual becomes a patient in a quit-smoking program. In such a case, the quantification allows a caregiver or counselor to follow the patient along during as the patient reduces their smoking activity. For example, the patient may reduce from 20 cigs per day to 18 to 16 and so on. However, at 10 cigs per day, the patient may still have a Daily CO Load that has not lowered because they are compensating when the smoke the reduced number of cigarette (i.e., the patient smokes harder and deeper and more intensely). The patient's reduced smoking exposure only occurs when their CO load decreases.

The data shown in FIG. 29 is intended for illustration purposes only and the duration of the period of time for a given dataset depends on the amount of time the individual uses the portable sampling unit to capture the biometric and behavioral data. Quantifying the exposure of exhaled carbon monoxide comprises correlating a function of exhaled carbon monoxide versus time over the period of time using the dataset and obtaining the area under the eCO curve 412. In variations of the method and system, the eCO curve can be calculated or approximated.

Figure 30:
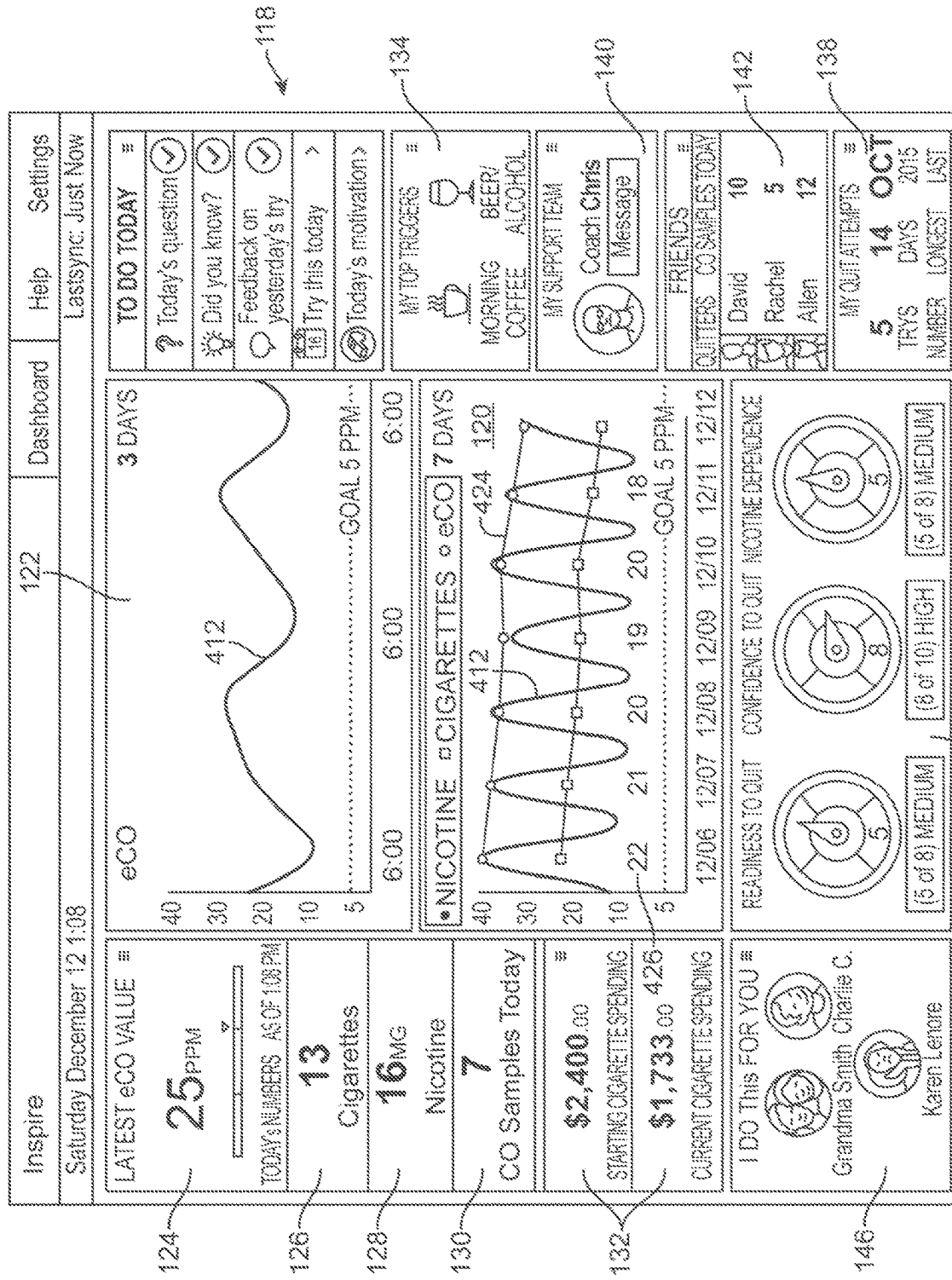
FIG. 30 illustrates an example of displaying the biometric data as well as various other information for assessing the smoking behavior of the individual.

FIG. 30 illustrates an example of displaying the biometric data as well as various other information for the benefit of the user, caregiver, or other party having an interest in assessing the smoking behavior of the individual. The data illustrated in FIG. 30 is for purposes of illustration and can be displayed on the portable electronic device (e.g., see 110 in FIG. 27) or on one or more computers. In addition, any of the biometric data or other data can be displayed on the portable sampling unit 1900.

FIG. 30 illustrates a "dashboard" view 118 of the individual's smoking behavioral data including a graphical output 120 of the eCO curve 412 over a period of time as well as the cigarette count for any given interval of time within the period of time. Graphical output 120 can also provide a measured or calculated nicotine trend 424. This nicotine trend 424 can be determined from the number of cigarettes smoked 426 rather than being a direct measurement of nicotine.

FIG. 30 also illustrates a second graphical output display 122 of an eCO curve 412 over an alternate time period. In this example, the first graphical display 120 shows the eCO curve 412 over 7 days while the second display 122 shows the data over 3 days. The dashboard view 118 can also include additional information including the latest eCO Burden/Load 124 (or the latest eCO reading from the latest sample), the number of cigarettes 126 over a defined period such as the current day, as well as the amount of nicotine 128. In addition, the dashboard 118 can also include a count of the number of samples 130 provided by the individual over a defined period (such as a daily through monthly count).

The dashboard 118 can also display information that can assist the individual in the reduction or cessation of smoking. For example, FIG. 30 also shows a cost of cigarettes 132 using the count of the portion of cigarettes smoked by the individual 126 or 426. The dashboard can also display social connections 146, 142, 140 to assist in cessation of smoking. For example, the dashboard can display a medical practitioner or counselor 140 that can be directly messaged. In addition, information can be displayed on social acquaintances 142 that are also trying to reduce their own smoking behavior.

The dashboard 118 can also display information regarding smoking triggers 134 as discussed above, for the individual as a reminder to avoid the triggers. The dashboard can also provide the user with additional behavioral information, including but not limited to the results of behavioral questionnaires 136 that the individual previously completed with his/her medical practitioner or counselor.

The dashboard 118 can also selectively display any of the information discussed herein based on an analysis of the individual. For example, it may be possible to characterize the individual's smoking behaviors and associate such behaviors with certain means that are effective in assisting the individual in reducing or ceasing smoking. In these cases, where the individual's behaviors allow for classifying in one or more phenotypes (where the individual's observable traits allow classifying within one or more groups, the dashboard can display information that is found to be effective for that phenotype. Furthermore, the information on the dashboard can be selectively adjusted by the user to allow for customization that the individual finds to be effective as a non-smoking motivator.

Figure 31:
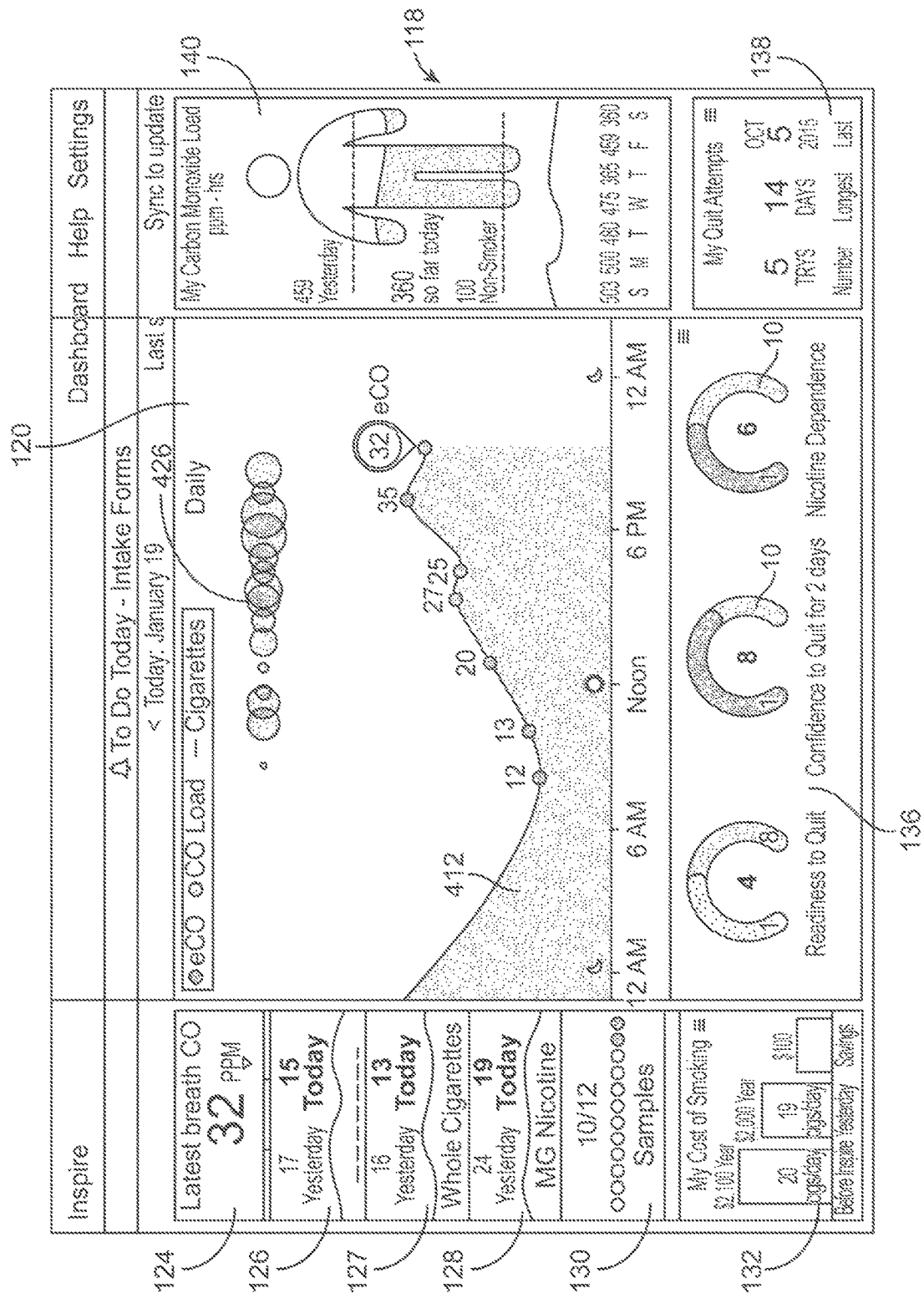
FIG. 31 shows another variation of a dashboard displaying similar information to that shown in FIG. 30.

FIG. 31 shows another variation of a dashboard 118 displaying similar information to that shown in FIG. 30. As noted above, the displayed information is customizable. For example, this variation illustrates the eCO load 140 in a graphical display that shows historical data (yesterday's load), current eCO Burden or load, as well as a target level for that of non-smokers. As shown in FIGS. 30 and 31, the individual's previous attempts at quitting smoking 138 can be displayed. In addition, the graphical representation 120 of the eCO trend 412 can be illustrated with individual eCO readings (of the respective sample) can be displayed with information regarding the smoking times 426 as well as a graphic showing the time or duration of smoking (as shown by the circles of varying diameter). As noted above, such information can be entered by the portable sampling unit and displayed in additional forms as shown in 126 and 127, which respectively show historical and current data regarding the number of times smoked and the number of whole cigarettes smoked.

Figure 32A:
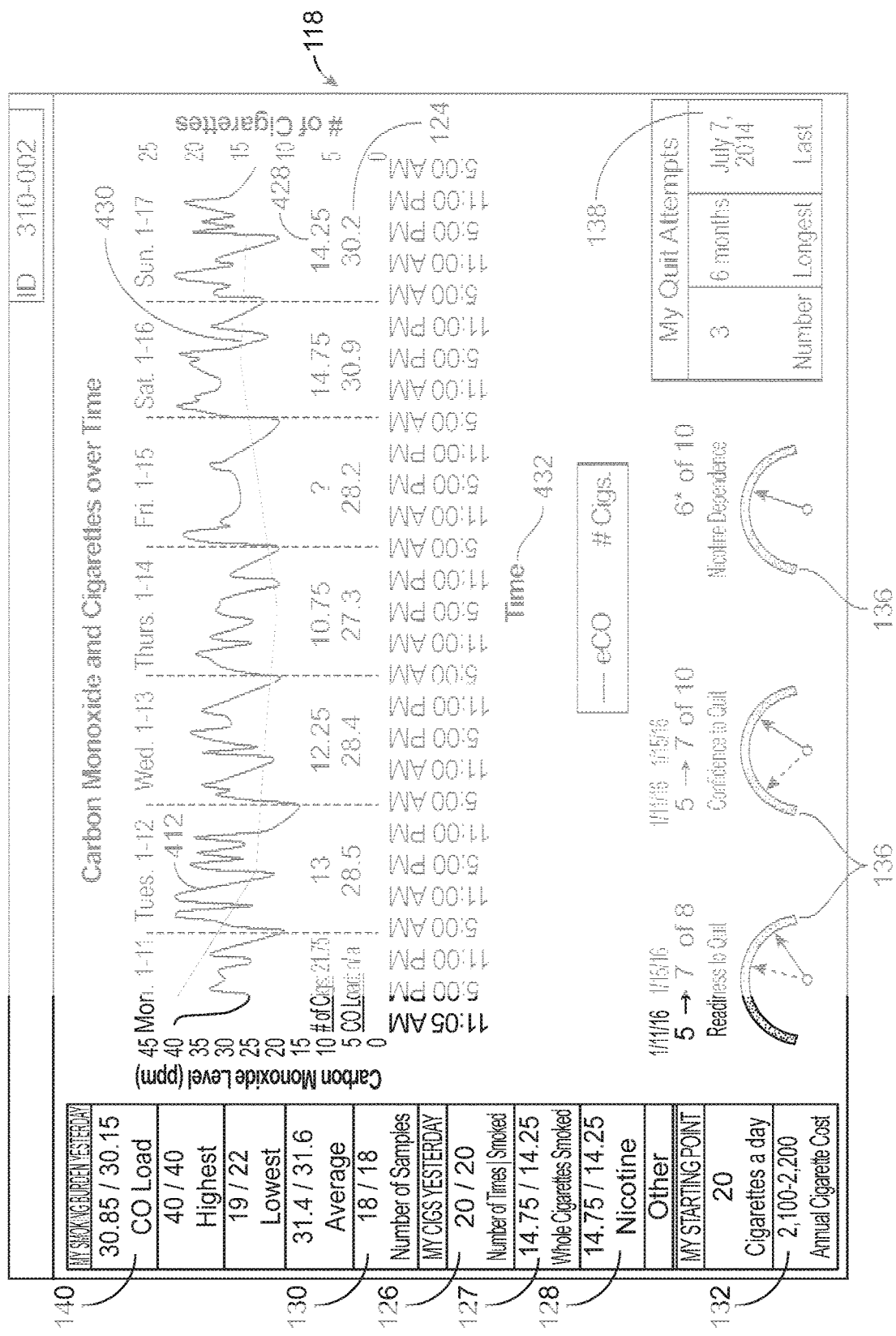
FIGS. 32A to 32C illustrate another variation of a dataset comprising exhaled carbon monoxide, collection time, and cigarette data quantified and displayed to benefit the individual attempting to understand their smoking behavior.
Figure 32B:
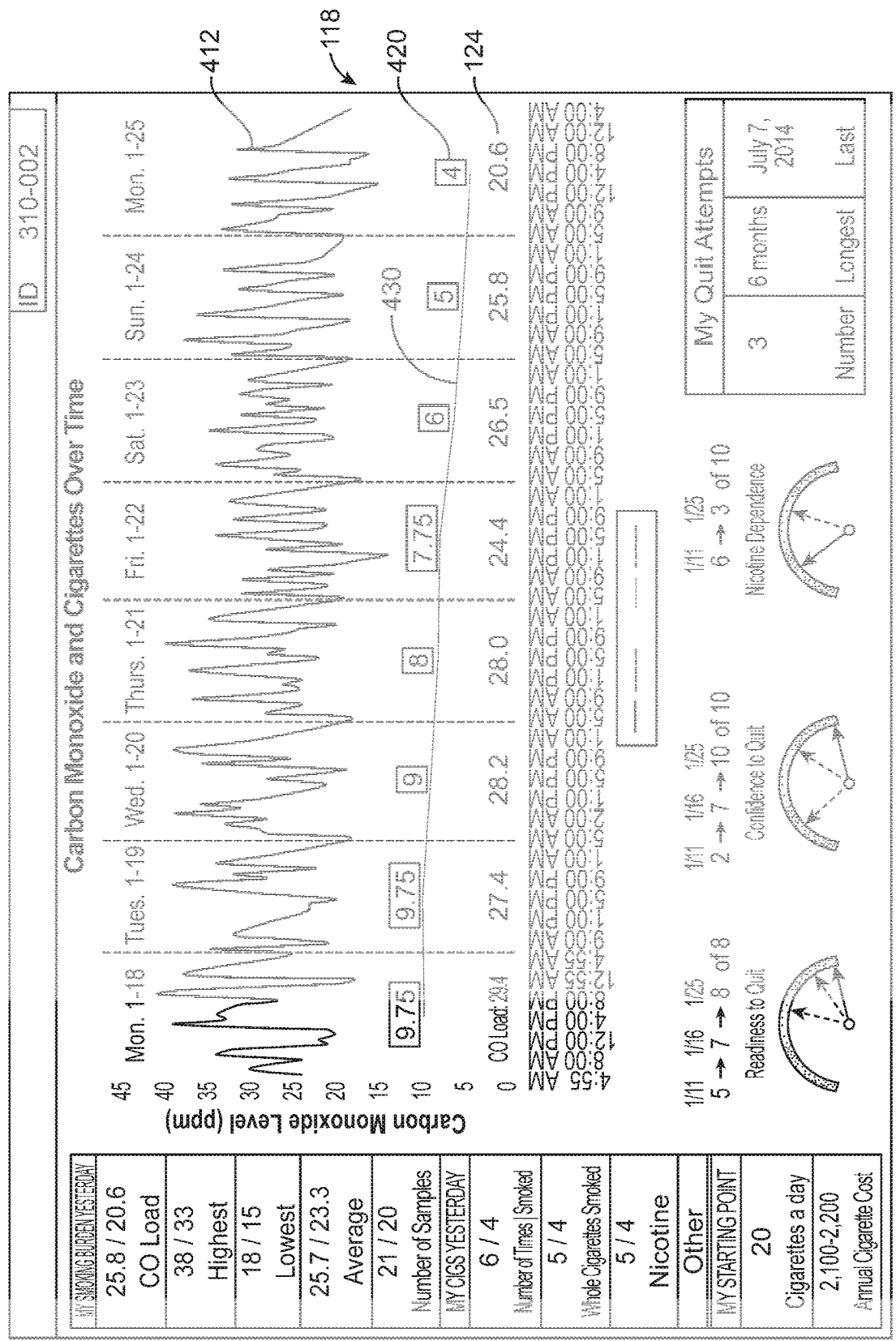
Figure 32C:
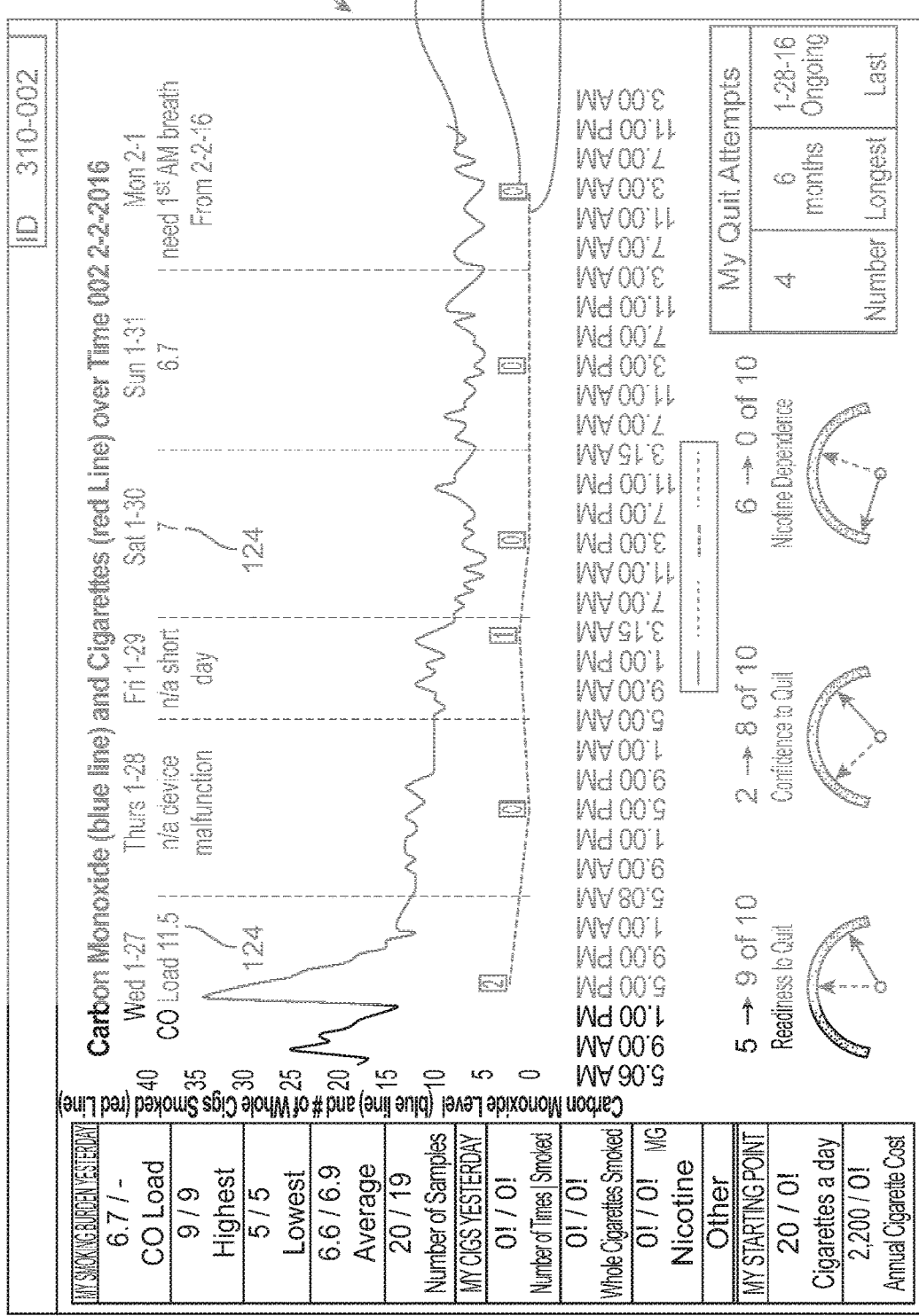

FIGS. 32A to 32C illustrate another variation of a dataset comprising exhaled carbon monoxide, collection time, and cigarette data quantified and displayed to benefit the individual attempting to understand their smoking behavior. FIG. 32A illustrates an example where a patient collected breath samples over the course of a number of days. The example data shown in FIGS. 32A to 32C demonstrate data shown over 21 days, but any time range is within the scope of the systems and methods described herein.

As illustrated in FIG. 32A, the period of time 432 is illustrated along the horizontal axis with the time intervals being each day within the time period. Although not shown, during the early stages of sample collection, the time period itself can comprise one or more days with the time interval being a multiple of hours or minutes. Clearly, the longer the time period the greater the ability of the program to select meaningful time intervals within the time period.

FIG. 32A illustrates a variation of a dashboard 118 where smoking data (comprising the total number of cigarettes 428 and an associated curve 430) are superimposed on a graph showing an eCO curve 412. As noted above, the individual provides breath samples on a regular or random basis. In certain variations, the portable sampling unit (not shown) prompts the individual to provide samples for measurement of CO. The portable sampling unit allows the samples to be associated with a time stamp and transmits other user generated data as discussed above. The CO data is then quantified to provide a value for the exposure of CO (eCO for exhaled CO) over an interval of time (e.g., per day as shown in FIG. 32A).

FIG. 32A also demonstrates the ability to show historical data simultaneously with present data. For example, the CO load data 140 illustrates the previous day's CO load as well as the highest CO reading, lowest CO reading, and average CO reading. Similar historical is shown regarding the cigarette data as well as the smoking cessation questionnaire results 136.

FIGS. 32B and 32C illustrate the dataset in graphical form as the individual decreases his/her smoking behavior. AS shown in FIG. 32C, as the individual continues to provide samples for measurement of CO, the graphical representation of the dataset shows the individual's self-reporting of smoking fewer cigarettes, which is verified through the reduced values of the CO load 124.

The systems and methods described herein, namely quantification and display of smoking behavior as well as other behavioral data provide a base for which healthcare professionals can leverage into effective programs designed to reduce the effects of cigarette smoke. For example, the system and methods described herein can be used to simply identify a population of smokers from within a general population. Once this population is identified, building the dataset on the individual's specific smoking behavior can be performed prior to attempting to enroll that individual in a smoking cessation program. As noted above, the quantification of the smoking burden (or CO burden) along with the time data of the smoking activity can be combined with other behavioral data to identify smoking triggers unique to that individual. Accordingly, the individual's smoking behavior can be well understood by the healthcare professional prior to selecting a smoking cessation program. In addition, the systems and methods described herein are easily adapted to monitor an individual's behavior once that individual enters a smoking cessation program and can monitor the individual, once they stop smoking, to ensure that the smoking cessation program remains effective and that the individual refrains from smoking.

In addition, the systems and methods described above regarding quantification of smoking behavior can be used to build, update and improve the model for smoking behavior discussed above as well as to provide perturbations to assist in ultimately reducing the individual's smoking behavior.

FIGS. 33A-33H illustrate another variation of the systems and methods described above used to implement a treatment plan for identifying a smoking behavior of an individual for ultimately assisting the individual with smoking cessation and maintaining the individual's status as a non-smoker.

Figure 33A:
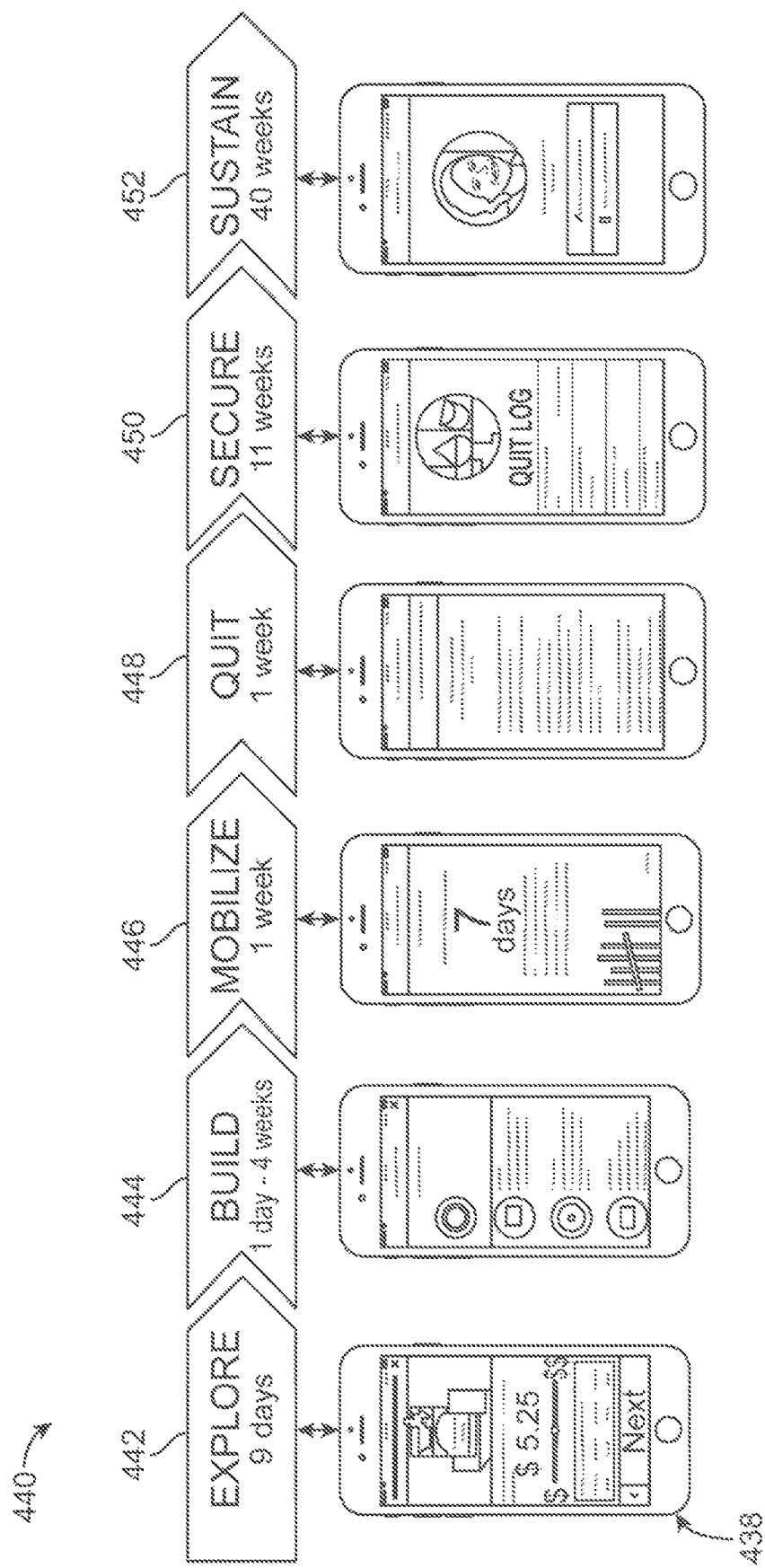

For example, FIG. 33A illustrates an outline of an exemplary outline that incorporates the teachings found herein to provide a multi-phased regime/program 440 intended to ultimately assist the individual in reducing and/or ceasing the smoking behavior. As shown, each phase 442, 444, 446, 448, 450, 452 of the program can be associated with a display 438. The illustrated display 438 represents a portable device (e.g., a smartphone, tablet, computer), however, the display can comprise any display, or dedicated electronic device where the user can receive and/or interact with the user interface and subject matter provided by the program. The subject matter provided by the program can be smoking-related subject matter that is intended to inform the individual about the effects of smoking and/or can be subject matter based on the smoking behavior. In addition, the subject matter can change based on the tracked behavior of the individual or the subject matter can change based on other factors that are unrelated to the tracked behavior of the individual.

The smoking related subject matter can also include information and/or warnings regarding proper use of devices and systems used to compile the smoking behavior. For example, the warnings can include warnings against using the device/system in those cases, including but not limited to use as a measurement of potential carbon monoxide poisoning, measurement of non-cigarette smoke inhalation (e.g., from a fire or chemical release). In some cases, the system can instruct the individual to call emergency medical services (e.g., 911) in the event non-cigarette CO exposure occurs. The system can also provide system specific warnings such as a warning against sharing of a breath sensor among different individuals.

Furthermore, the subject matter relayed to the individual can include a general reminder that no amount of smoking behavior is safe. Such a warning is intended to prevent an individual attempting to use the system to reduce or maintain his/her smoking behavior at a relative level that the individual might falsely perceive as being a safe level of smoking. For instance, such a warning can be triggered at a particular level of exhaled CO, e.g., 0-6 ppm. The warning would state that the low levels of CO in the exhaled breath do not indicate that it is safe to initiate or increase smoking, or that the current level is safe. The warning could further state that smoking is harmful to one's health and any amount of smoking is unsafe.

In the illustrated example, the phases 442, 444, 446, 448, 450, 452 of the program 440 can be broken into separate time spans or periods, where each phase offers a different goal that allows the individual to build and make progress in attempting to moderate their smoking behavior. For instance, in an example of the method/system, an initial phase 442 allows the user to explore their smoking behavior with little or no attempt at trying to enforce an immediate change in smoking behavior. Such an exploration phase 442 offers information to the individual that allows the individual to identify their smoking behavior. In the illustrated example shown in FIG. 33A, the program phases are separated as follows with exemplary time periods: Explore 442 (9 days), Build 444 (1 day to 4 weeks), Mobilize 446 (1 week), Quit 448 (1 week), Secure 450 (11 weeks), and Sustain 552 (40 weeks). Clearly, any variation of time period can be associated with each phase.

Explore 442 can be used to raise behavior about smoking behavior and spark an interest in the individual to quit. Build 444 can be used to build skills to encourage the individual to decide to quit. Mobilize 446 can be used to prepare the individual to quit. Quit 448 can be used to assist the individual in quitting. For example, this phase can be used to provide support to the individual during smoking cessation where the support includes facilitating interactive communication with the counselor, facilitating a peer support interactive communication, displaying informational subject matter to support smoking cessation, or a combination thereof. Secure 450 can be used to provide the individual with skills to continue to quit smoking. Sustain 452 can be used to provide support to the individual to prevent relapse and solidify their non-smoking behavior.

For example, as discussed above, such a first phase 442 can include recording a plurality of behavioral data from the individual, where such behavioral data can include number of cigarettes smoked, the time(s) a cigarette is smoked, the location of the individual, the location of the individual while smoking, moods, as well as any other data indicative of a behavior of the individual. In association with the behavioral data, the method can allow the individual to submit a plurality of biologic data from the individual. For instance, the biologic data can include exhaled air samples submitted to the electronic devices discussed above. Alternatively, or in combination, the submission of biologic data can occur passively through any number of sensors that actively measure biologic information of the individual (e.g., via blood, exhaled air, temperature, etc.).

The biologic information is then quantified, which allows the individual to understand the impact of the smoking exposure. As noted above, in those cases where the biologic data comprises exhaled carbon monoxide, the quantification of smoking exposure can comprise the exhaled carbon monoxide load.

Figure 33B:
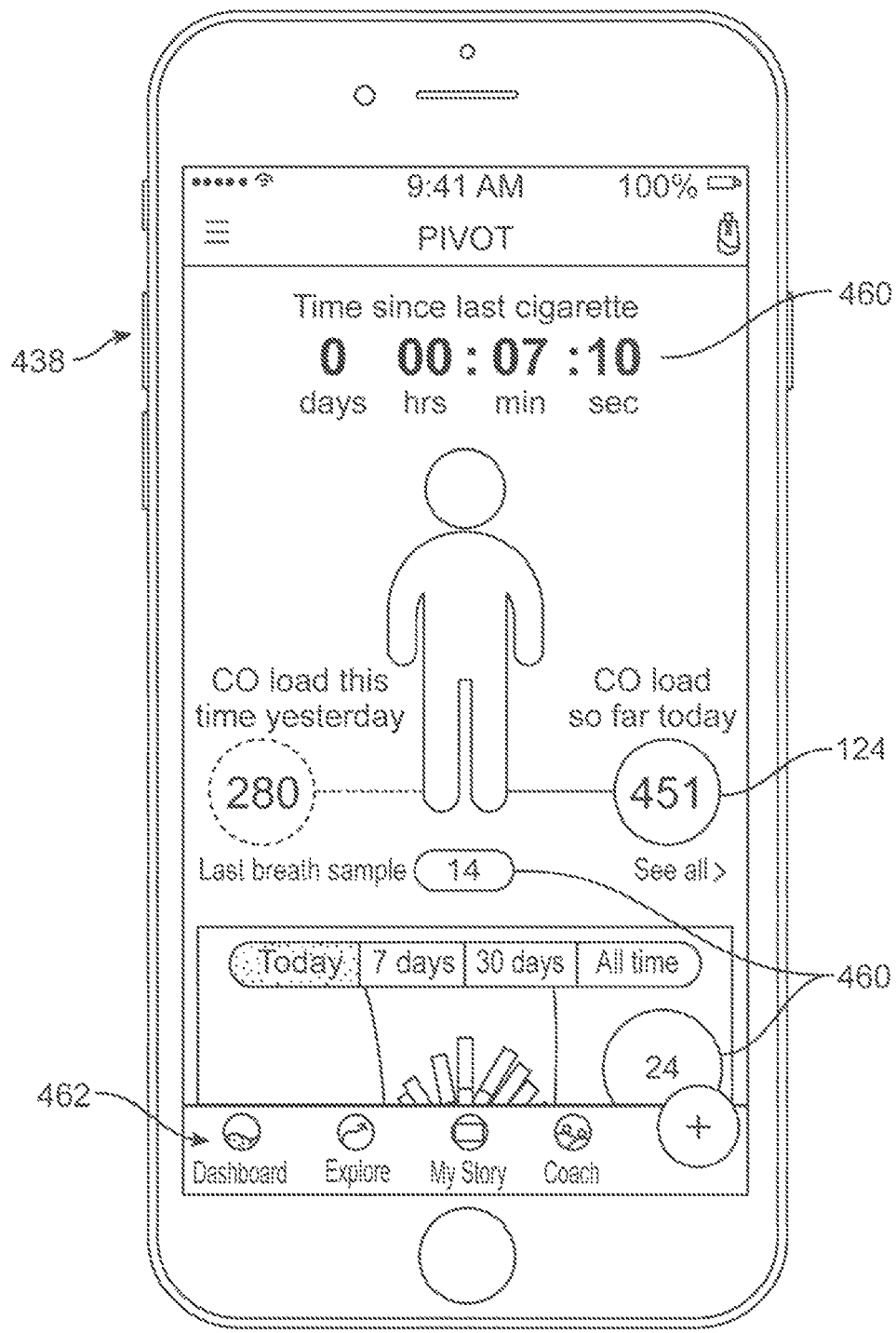

Next, the method comprises compiling a behavior summary that combines at least some of the behavioral data and the smoking exposure. FIG. 33B illustrates a display of an example of a behavior summary that illustrates smoking exposure/exhaled CO load 124 as well as a number of behavioral data, including but not limited to number of cigarettes smoked, estimated cost of smoking, and time since last cigarette smoked. The visual display can also provide various menu options 462 to allow an individual to interact between various subject matter items related to smoking behavior as well as a counselor. The display 438 can also allow the individual to view a behavior summary based on daily values, or over a set period of time (e.g., 7 days, 30 days, full history, etc.)

It is noted that the system can also assess the submitted data (either biologic and/or behavioral) to ensure accuracy of the data. For example, the system can assess the time span between submitted samples and provide a warning if the samples are submitted at undesirable intervals. For instance, the system can provide a warning to the individual if obtaining the plurality of biologic data from the individual occurs within a pre-determined time of a previous submission of biologic data. In some cases, especially for biologic data, submission of samples without allowing a sufficient time between samples can lower the effectiveness of the measurement. In additional variations, the warning to the individual can further comprise rejecting at least one of the plurality of biologic data from the individual in addition to providing the warning. Such a warning can be provided visually, audibly, sensory, and/or through the visual display of subject matter discussed herein.

FIG. 33C illustrates an additional example of a behavior summary comprising behavioral data 460 in conjunction with biologic data 124. In this example, the user is able to choose between a display of biologic data (e.g., exhaled carbon monoxide load) and the number of cigarettes smoked. In addition, the display 438 allows for the user to interact with the data by selecting specific information such as a smoking map that shows behavioral data in the form of smoking locations 464. The present disclosure includes any number of variations of displaying either all or at least a portion of the behavior summary to the individual to inform the individual about the smoking behavior.

FIG. 33D illustrates another example of the method disclosed herein using one or more interactive activities to engage the individual during the program. In this variation, the interactive activities can be spread through a first phase of the program. For example, while the first phase of the program can comprise any time span, in the illustrated variation, the first phase is separated into 9 days with each day having a marker 468, 470, 474 that represents that day's activities. The markers can be interactive, meaning that they allow the individual to access an activity, or the markers can be on-directional in providing the user with information. Regardless, the activities can provide subject matter to the individual regarding smoking behavior. For instance, as shown in FIG. 33D, the initial activity 468 can serve as a reminder or trigger the individual to begin the submission of biologic and/or behavioral data as described above and the method can produce subject matter that incorporates any of the data to provide feedback to the user. In FIG. 33D, the first activity 468 provides subject matter feedback to the user regarding the need for biologic samples (e.g., breath samples) and can provide any information related to the biologic or behavioral samples, such as a current count, a minimum number of required samples, or a countdown until the minimum number of samples are met.

Figure 33E:
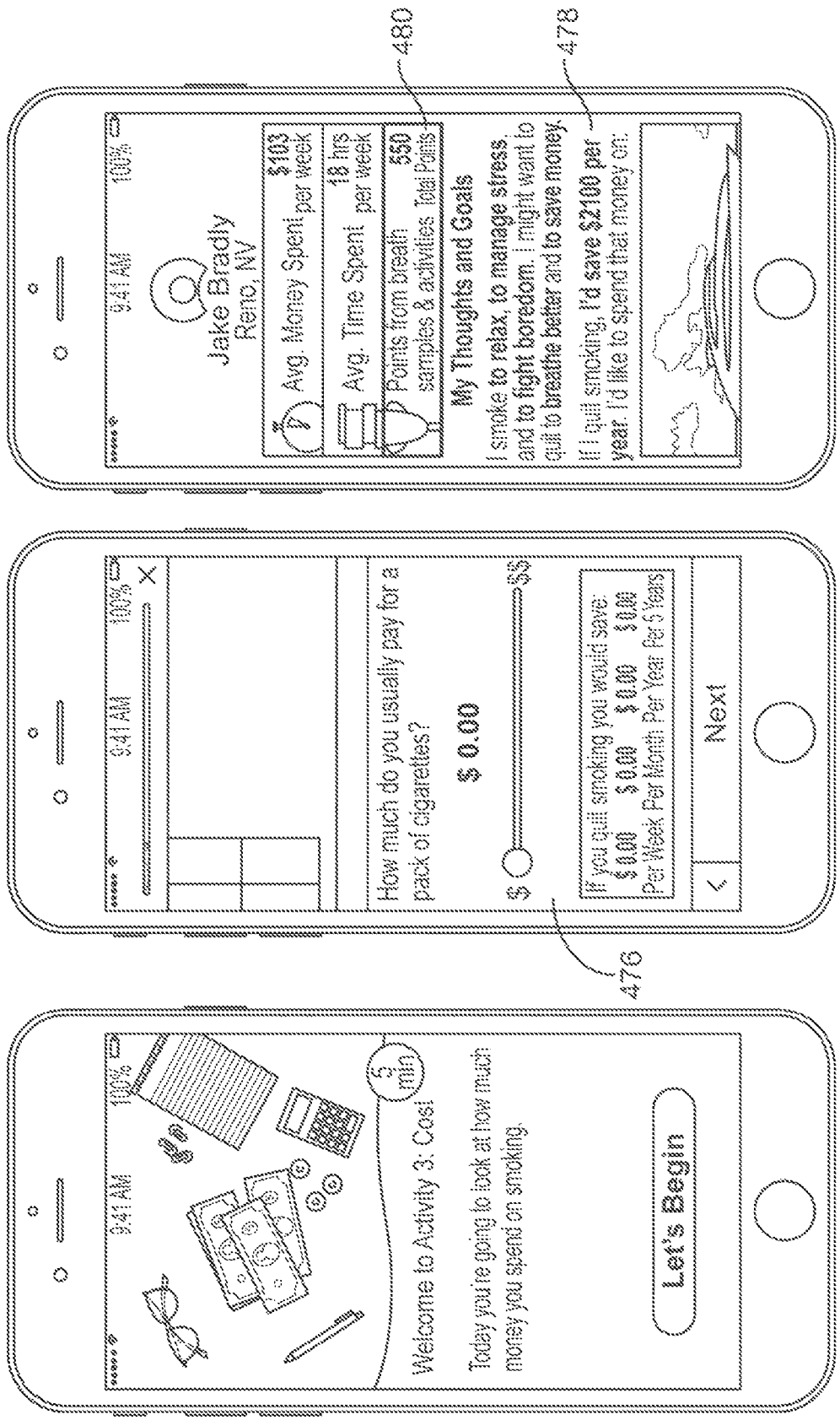

FIG. 33D also illustrates additional markers 468, 474 that represent additional activities and/or days of the first phase of the program. As shown in FIG. 33D, the subject matter 472 can be purely informational such as providing information on how measured CO is a useful indicator of the individual's exposure to toxins in cigarettes. In other variations, as shown in FIG. 33E, the subject matter can comprise interactive activities. For example, as shown in FIG. 25E the middle screen image prompts an individual for the cost associated with cigarettes or smoking and can calculate the information as shown. The activity can then combine the prompted information, as shown in the right screen, to provide additional information indicative of the individual's smoking behavior 478. For instance, in this example, the information comprises the estimated cost of smoking, the reasons for smoking, and an estimated extrapolated savings upon quitting smoking. The interactive activity can also provide a reward 480 to the individual for providing biologic and/or behavioral data.

FIG. 33F illustrates additional markers 482, 486, 488, 490, and 496 representing subjects such as reasons for smoking 482, addition 486, household 488, time (spent smoking) 490, and confidence 496. As shown, the displayed subject matter can be purely informational (e.g., displaying reasons for smoking 484) or can be combined with data entered during the program (e.g., displaying the amount of time spent smoking per week 492).

Figure 33G:
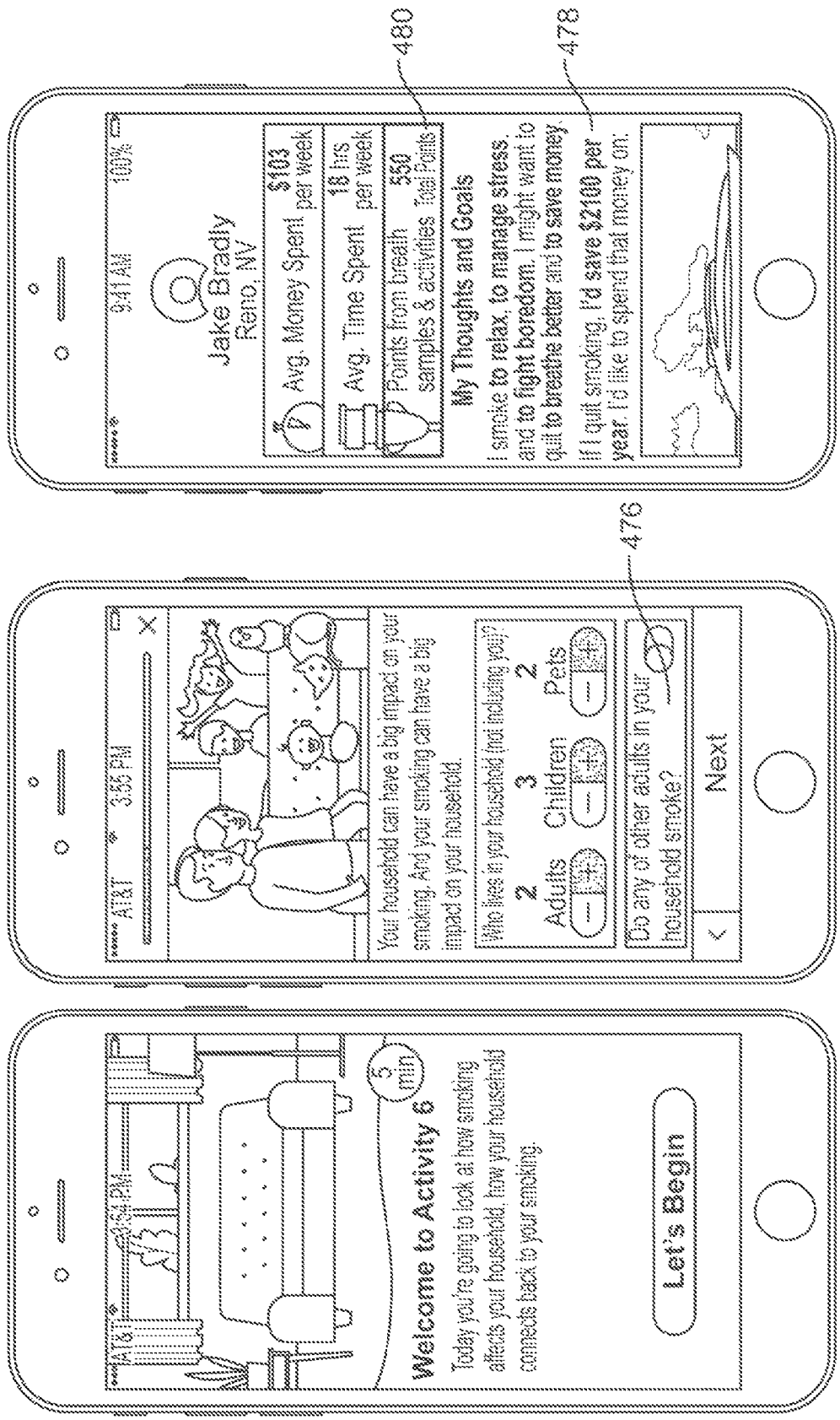

FIG. 33G illustrates another activity (associated with activity six 488 of FIG. 33F), in this example, as shown in the middle screen, the interactive data prompted by the program relates to environmental factors associated with the individual (e.g., household information). Once the individual enters the environmental information, the program can then combine the prompted environmental information, as shown in the right screen, to provide additional information indicative of the individual's smoking behavior 478 using the environmental data.

FIG. 33H represents activities or days seven through nine 490, 496, 498. As the first program phase approaches an end, the individual can be prompted for their confidence in their ability to quit smoking 494 which can be affected given that the program will have provided the individual with the above metrics regarding his/her smoking behavior. Once the initial program phase ends, as denoted by a completion marker 498, the individual will have a personalized smoking behavior profile compiled using metrics specific to that individual. The interactive activities can then prompt the individual to enter the next phase of the program (as outlined in FIG. 33A).

A number of embodiments of the invention have been described. Nevertheless, it will be understood that various modifications may be made without departing from the spirit and scope of the invention. Combination of the aspect of the variations discussed above as well combinations of the variations themselves are intended to be within the scope of this disclosure.

Various changes may be made to the invention described and equivalents (whether recited herein or not included for the sake of some brevity) may be substituted without departing from the true spirit and scope of the invention. Also, any optional feature of the inventive variations may be set forth and claimed independently, or in combination with any one or more of the features described herein. Accordingly, the invention contemplates combinations of various aspects of the embodiments or combinations of the embodiments themselves, where possible. Reference to a singular item, includes the possibility that there are plural of the same items present. More specifically, as used herein and in the appended claims, the singular forms "a," "an," "said," and "the" include plural references unless the context clearly dictates otherwise.

What is claimed is:

1. A method of enhancing an electronic interaction between a coach-counselor assisting an individual-user participating in a behavioral-modification program, the method comprising:
   providing electronic access to a database of information to the coach-counselor during the electronic interaction between the coach-counselor and the individual-user, where the database of information includes a plurality of user-specific input data specific to the individual-user, where the plurality of user-specific input data includes a subset of individual-user biological input data and at least one of a subset of individual-user psychographic information and a subset of individual-user personal information, where at least a portion of the plurality of user-specific input data is previously collected;
   electronically displaying a background data to the coach-counselor during the electronic interaction;
   electronically supplying the coach-counselor with at least one prompt of a communication topic from a database of generic information applicable to the behavioral-modification program, wherein the at least one prompt is customizable by the coach-counselor; and
   electronically transmitting the at least one prompt to the individual-user as a coach-message.

2. The method of claim 1, where electronically transmitting the at least one prompt occurs automatically without input from the coach-counselor.

3. The method of claim 1, where electronically transmitting the at least one prompt occurs requires an input from the coach-counselor.

4. The method of claim 1, further comprising establishing an electronic reporting interface for the coach-counselor, where the electronic reporting interface allows the coach-counselor to electronically access a database of batch data that includes information from a plurality of users who participated in the behavioral-modification program.

5. The method of claim 1, wherein the database of information further includes a behavior summary of the individual-user, where the behavior summary comprises an association of the individual-user biological input data from the individual-user with at least one of a plurality of behavioral data supplied by the individual-user where the plurality of behavioral data is non-biologic.

6. The method of claim 1, further comprising allowing the coach-counselor to update the database of information about the individual-user.

7. The method of claim 1, wherein the subset of individual-user personal information in the database of information includes information from a group consisting of background, traits, demographics, and previous notes about the individual-user.

8. The method of claim 1, wherein the subset of individual-user psychographic information in the database of information includes milestones and targets.

9. The method of claim 1, where electronically displaying the background data includes displaying a conversation history between the individual-user and the coach-counselor.

10. The method of claim 1, wherein the at least one prompt comprises a reusable prompt that is applicable to multiple alternate users.

11. The method of claim 1, wherein the at least one prompt requires selection by the coach-counselor, and wherein the at least one prompt comprises encoded variables that are pre-filled when the at least one prompt is selected by the coach-counselor.

12. The method of claim 1, wherein the at least one prompt includes placeholders and the method further comprising preventing electronically transmitting the at least one prompt until coach-counselor replaces the placeholders with text.

13. The method of claim 1, further comprising tagging the coach-message to assign a relevant category.

14. The method of claim 13, wherein the relevant category includes a trigger or a behavior.

15. The method of claim 1, wherein the coach-message is added to the database of information about the individual-user.

16. The method of claim 15, further comprising assigning the coach-message as either private or public.

17. The method of claim 1, wherein enabling the coach-counselor to select data from the database of information comprises enabling the coach-counselor to search by content of the at least one prompt.

18. The method of claim 1, further comprising altering the at least one prompt to maintain stylistic similarity to the coach-counselor.

19. The method of claim 1, wherein the behavioral-modification program comprises preventing a behavior selected from a group consisting of smoking cigarettes, vaping, consuming alcohol, use of tobacco, use of narcotics.

20. A method of enhancing an electronic interaction between a coach-counselor assisting an individual-user participating in a behavioral-modification program, the method comprising:
providing electronic access to a database of information during the electronic interaction between the coach-counselor and the individual-user, where the database of information includes a plurality of user-specific input data specific to the individual-user, where the plurality of user-specific input data includes a subset of individual-user biological input data and at least one of a subset of individual-user psychographic information and a subset of individual-user personal information, where at least a portion of the plurality of user-specific input data is previously collected;
electronically supplying the coach-counselor with at least one prompt of a communication topic from a database of generic information applicable to the behavioral-modification program;
wherein the at least one prompt comprises a partially written statement, wherein the coach-counselor must complete the partially written statement into a completed statement prior to sending the completed statement to the individual-user; and
electronically transmitting the at least one prompt to the individual-user as a coach-message.

\* \* \* \* \*